US012593974B2

(12) United States Patent
Grossberg

(10) Patent No.: US 12,593,974 B2
(45) Date of Patent: Apr. 7, 2026

(54) SYSTEMS AND METHODS FOR AUTOMATED SUBJECTIVE REFRACTIONS

(71) Applicant: Lombart Brothers, Inc., Jacksonville, FL (US)

(72) Inventor: Matthew Grossberg, Atlantic Beach, FL (US)

(73) Assignee: Lombart Brothers, Inc., Jacksonville, FL (US)

( * ) Notice: Subject to any disclaimer, the term of this patent is extended or adjusted under 35 U.S.C. 154(b) by 0 days.

(21) Appl. No.: 18/239,579

(22) Filed: Aug. 29, 2023

(65) Prior Publication Data

US 2023/0397808 A1 Dec. 14, 2023

Related U.S. Application Data

(63) Continuation of application No. 17/022,539, filed on Sep. 16, 2020, now Pat. No. 11,779,202.

(Continued)

(51) Int. Cl.
*A61B 3/028* (2006.01)
*A61B 3/032* (2006.01)
*A61B 3/12* (2006.01)

(52) U.S. Cl.
CPC ............ *A61B 3/0285* (2013.01); *A61B 3/032* (2013.01); *A61B 3/12* (2013.01)

(58) Field of Classification Search
CPC .................................................. A16B 3/0285

(Continued)

(56) References Cited

U.S. PATENT DOCUMENTS

D297,243 S     8/1988   Wells-Papanek et al.
4,869,589 A *  9/1989   Blair ........................ A61B 3/02
                                                351/243

(Continued)

FOREIGN PATENT DOCUMENTS

CN          1227559 C       11/2005
EP        2 477 533 A1       7/2012

(Continued)

OTHER PUBLICATIONS

Phoroptor VRx Digital Refraction System User's Guide, Reichert, Inc., Depew, NY, 2018 (Year: 2018).*

(Continued)

*Primary Examiner* — Zachary W Wilkes
(74) *Attorney, Agent, or Firm* — Foley & Lardner LLP

(57) ABSTRACT

A system for administering a subjective refraction comprising a phoropter, a display, and a computing device configured to generate a first set of conditions for a first test; receive a first input indicative of the patient's vision under the first set of conditions; automatically display, based on the first input, an updated first visual reference; iteratively update, based on the first input, a second combination of the plurality of lenses and receive feedback from the patient until a predefined number of responses are received to determine an endpoint for the first test; automatically generate and display a second set of conditions for a second test and a second plurality of response fields; receive an updated input indicative of the patient's vision under the second set of conditions; and determine an endpoint for the second test based on a determined a visual acuity matching a predefined visual acuity value.

20 Claims, 28 Drawing Sheets

Related U.S. Application Data

(60) Provisional application No. 62/901,691, filed on Sep. 17, 2019.

(58) Field of Classification Search
USPC ........................................................ 351/233
See application file for complete search history.

(56)                    References Cited

U.S. PATENT DOCUMENTS

| | | | |
|---|---|---|---|
| 5,568,209 A | 10/1996 | Priester et al. | |
| D396,488 S | 7/1998 | Kunkler | |
| 5,805,268 A | 9/1998 | Hosoi et al. | |
| 5,914,772 A | 6/1999 | Dyer | |
| D412,323 S | 7/1999 | Kahn et al. | |
| 5,929,972 A * | 7/1999 | Hutchinson | A61B 3/032 |
| | | | 351/200 |
| D420,995 S | 2/2000 | Imamura et al. | |
| D436,580 S | 1/2001 | Navano et al. | |
| D439,584 S | 3/2001 | Wang et al. | |
| D473,236 S | 4/2003 | Robbin et al. | |
| 6,761,453 B2 | 7/2004 | Wilson | |
| D508,248 S | 8/2005 | Ording | |
| 6,952,221 B1 | 10/2005 | Holtz et al. | |
| 7,232,220 B2 | 6/2007 | Franz et al. | |
| D551,243 S | 9/2007 | Young | |
| D557,268 S | 12/2007 | Fletcher | |
| D559,262 S | 1/2008 | Young | |
| 7,520,611 B2 | 4/2009 | Franz et al. | |
| D594,467 S | 6/2009 | Kase | |
| D596,193 S | 7/2009 | Shotel | |
| D637,201 S | 5/2011 | Wasko et al. | |
| 7,954,950 B2 | 6/2011 | Dreher et al. | |
| D649,154 S | 11/2011 | Vance et al. | |
| D649,557 S | 11/2011 | Duchâ¿Ne | |
| 8,167,429 B1 | 5/2012 | Butler et al. | |
| 8,182,091 B2 | 5/2012 | Foster | |
| D665,422 S | 8/2012 | Morrow et al. | |
| 8,444,270 B2 | 5/2013 | Nordstrom | |
| 8,632,184 B2 | 1/2014 | Lai | |
| 8,636,363 B2 | 1/2014 | Roser | |
| D698,806 S | 2/2014 | Funabashi et al. | |
| D706,792 S | 6/2014 | Kavett | |
| 8,740,386 B2 | 6/2014 | Foster | |
| 8,888,288 B2 * | 11/2014 | Iravani | A61B 3/032 |
| | | | 351/223 |
| 8,888,289 B2 | 11/2014 | Thompson et al. | |
| D723,058 S | 2/2015 | Matsuda | |
| D725,138 S | 3/2015 | Brotman et al. | |
| 8,967,801 B2 | 3/2015 | Lai | |
| D728,610 S | 5/2015 | Lee et al. | |
| D731,536 S | 6/2015 | Jeong et al. | |
| 9,046,683 B2 | 6/2015 | Caldeira et al. | |
| 9,173,565 B2 | 11/2015 | Foster | |
| 9,230,062 B2 | 1/2016 | Seriani | |
| 9,237,842 B2 | 1/2016 | Lee et al. | |
| 9,241,621 B2 * | 1/2016 | Park | A61B 3/032 |
| D749,621 S | 2/2016 | Gerhan et al. | |
| D759,042 S | 6/2016 | Heeter et al. | |
| 9,408,533 B2 | 8/2016 | Lai | |
| D770,519 S | 11/2016 | Kobetz et al. | |
| 9,492,074 B1 | 11/2016 | Lee et al. | |
| 9,504,378 B2 | 11/2016 | Lee et al. | |
| D774,520 S | 12/2016 | Kim et al. | |
| D777,182 S | 1/2017 | Holm et al. | |
| D778,284 S | 2/2017 | Dahlen | |
| D778,314 S | 2/2017 | Li et al. | |
| 9,635,091 B1 | 4/2017 | Laukkanen et al. | |
| 9,730,578 B2 | 8/2017 | Lai | |
| D808,995 S | 1/2018 | Weaver et al. | |
| 9,888,847 B2 | 2/2018 | Sakurada et al. | |
| 9,980,644 B2 | 5/2018 | Fried et al. | |
| D819,666 S | 6/2018 | Porter et al. | |
| D822,052 S | 7/2018 | Rickes et al. | |
| D825,605 S | 8/2018 | Jann et al. | |
| D825,609 S | 8/2018 | Andrizzi et al. | |
| D826,255 S | 8/2018 | Andrizzi et al. | |
| 10,083,279 B2 | 9/2018 | Seriani | |
| D838,277 S | 1/2019 | Asai | |
| 10,194,794 B2 | 2/2019 | Lai | |
| 10,194,799 B2 | 2/2019 | Gerrans | |
| D846,583 S | 4/2019 | Martin et al. | |
| 10,299,672 B2 | 5/2019 | Shibata et al. | |
| 10,362,934 B2 | 7/2019 | Greivenkamp et al. | |
| 10,398,304 B2 | 9/2019 | Lee | |
| 10,405,741 B2 | 9/2019 | Sugiura et al. | |
| 10,413,172 B2 | 9/2019 | Jensen et al. | |
| D870,765 S | 12/2019 | Georg et al. | |
| D879,117 S | 3/2020 | Dellinger et al. | |
| D894,950 S | 9/2020 | Shuttleworth et al. | |
| D895,661 S | 9/2020 | Lei | |
| D903,708 S | 12/2020 | Poueriet | |
| D910,692 S | 2/2021 | Coverstone et al. | |
| D918,937 S | 5/2021 | Walsh et al. | |
| 10,996,838 B2 | 5/2021 | Gervais et al. | |
| D938,485 S | 12/2021 | Grossberg | |
| D938,984 S | 12/2021 | Grubbs et al. | |
| D938,986 S | 12/2021 | Grossberg | |
| 11,202,565 B2 * | 12/2021 | Pichereau-Basle | A61B 3/103 |
| D970,527 S | 11/2022 | Kandula et al. | |
| D973,092 S | 12/2022 | Kennedy et al. | |
| 11,582,338 B2 | 2/2023 | Grajales | |
| D986,277 S | 5/2023 | Grossberg | |
| D986,278 S | 5/2023 | Grossberg | |
| D986,922 S | 5/2023 | Grossberg | |
| D989,109 S | 6/2023 | Bayliss et al. | |
| D993,982 S | 8/2023 | Wang et al. | |
| D993,983 S | 8/2023 | Farlow et al. | |
| 11,779,202 B2 * | 10/2023 | Grossberg | A61B 3/032 |
| | | | 351/216 |
| D1,042,472 S | 9/2024 | Matsuda et al. | |
| 2005/0127064 A1 | 6/2005 | Garcia et al. | |
| 2006/0023163 A1 | 2/2006 | Foster | |
| 2008/0198328 A1 | 8/2008 | Seriani et al. | |
| 2009/0249400 A1 | 10/2009 | Carlberg et al. | |
| 2011/0082704 A1 | 4/2011 | Blum | |
| 2011/0119079 A1 | 5/2011 | Schoenberg | |
| 2012/0057007 A1 | 3/2012 | Ishiguro | |
| 2012/0120369 A1 * | 5/2012 | Lai | A61B 3/0285 |
| | | | 351/239 |
| 2012/0212706 A1 * | 8/2012 | Chou | A61B 3/036 |
| | | | 351/246 |
| 2013/0141694 A1 | 6/2013 | Seriani | |
| 2015/0070650 A1 | 3/2015 | Seriani | |
| 2015/0150446 A1 * | 6/2015 | Park | A61B 3/0285 |
| | | | 351/246 |
| 2015/0190047 A1 | 7/2015 | Sugiura et al. | |
| 2015/0342459 A1 | 12/2015 | Robert et al. | |
| 2015/0374233 A1 | 12/2015 | Zhang et al. | |
| 2016/0029885 A1 | 2/2016 | Hoof et al. | |
| 2016/0310000 A1 | 10/2016 | Meneghini | |
| 2017/0027436 A1 | 2/2017 | Lee et al. | |
| 2017/0188810 A1 * | 7/2017 | Kim | A61B 3/028 |
| 2017/0188811 A1 | 7/2017 | Lee | |
| 2017/0215723 A1 | 8/2017 | Sakurada et al. | |
| 2017/0245758 A1 | 8/2017 | Liang | |
| 2017/0329154 A1 | 11/2017 | Liang | |
| 2018/0136486 A1 | 5/2018 | Macnamara et al. | |
| 2018/0192868 A1 | 7/2018 | Sakurada et al. | |
| 2018/0192872 A1 | 7/2018 | Fried et al. | |
| 2018/0301226 A1 | 10/2018 | Seriani | |
| 2019/0014981 A1 | 1/2019 | Hooriani et al. | |
| 2019/0082951 A1 | 3/2019 | Merriam et al. | |
| 2019/0133441 A1 | 5/2019 | Verdooner et al. | |
| 2019/0148016 A1 | 5/2019 | Seriani | |
| 2019/0148017 A1 | 5/2019 | Seriani | |
| 2019/0380575 A1 * | 12/2019 | Pichereau-Basle | |
| | | | A61B 3/0041 |
| 2020/0196863 A1 | 6/2020 | Anderson et al. | |
| 2021/0076928 A1 | 3/2021 | Grossberg | |
| 2021/0106216 A1 * | 4/2021 | Longo | A61B 3/032 |

(56) References Cited

U.S. PATENT DOCUMENTS

| | | |
|---|---|---|
| 2021/0290051 A1 | 9/2021 | Tang et al. |
| 2021/0290056 A1 | 9/2021 | Karandikar et al. |

FOREIGN PATENT DOCUMENTS

| | | | |
|---|---|---|---|
| WO | WO-9802083 A2 * | 1/1998 | ............. G06V 40/19 |
| WO | WO-02/098290 A2 | 12/2002 | |
| WO | WO-2010/009450 A1 | 1/2010 | |
| WO | WO-2011/043922 A1 | 4/2011 | |
| WO | WO-2013/049778 A1 | 4/2013 | |
| WO | WO-2013/155002 A1 | 10/2013 | |
| WO | WO-2014/074157 A1 | 5/2014 | |
| WO | WO-2017/218539 A1 | 12/2017 | |
| WO | WO-2018/013923 A1 | 1/2018 | |
| WO | WO-2018/163166 A2 | 9/2018 | |
| WO | WO-2019/099952 A1 | 5/2019 | |

OTHER PUBLICATIONS

Christiaan123joubert, Topcon EyeCare Videos CV5000, Sep. 14, 2012, youtube.com, retrieved Apr. 7, 2022, available at https://www.youtube.com/watch?v=bCy009eYvpU (Year: 2012).

Chubarovy, Blue Buttons, dated Aug. 2, 2017, retrieved Aug. 3, 2023 from https://www.istockphoto.com/vector/blue-buttons-round-square-and-oval-shiny-icons-gm825855404-134007343, 1 page.

Kirkner, Richard, Refraction Revisited, Nov. 16, 2015, visionmonday.com (online), accessed Jan. 7, 2021, available at https://www.visionmonday.com/CMSDocuments/2015/11/coverstory_VM111615.pdf (Year 2015).

Nidek Co., Ltd., Nidek Refractor Model RT-900 Operator's Manual, Mar. 2009, 104 pages.

Tampoya, Jeremiah, Topcon CV-5000 Auto Phoropter Tutorial with RevolutionEHR Integration, Jan. 26, 2018, https://www.youtube.com/watch?v=jCxnG-Q_eg0, 3 pages.

Thomson Software Solutions, Test Chart 2016, Changing Sphere Cyl and Axis, 2016, thomson-software-solutions.com (online), accessed Jan. 7, 2021, available at https://www.thomson-software-solutions.com/OnlineResources/Test%20Chart%202016/Help/Test%20Chart%202016.html?ChangingSphereCylandAxis.html (Year: 2016).

Topcon Corporation, Instruction Manual CV 1Dial Controller KB-50, Apr. 1, 2008, 90 pages.

Topcon Corporation, User Manual Compu-Vision CV-5000, Mar. 1, 2013, 220 pages.

Topcon Europe Medical, Topcon CV-5000 Automated Phoropter, Jul. 30, 2012, https://www.youtube.com/watch?v=tTzh0167XSM, 2 pages.

Topcon Healthcare, Chronos Brochure, believed to be available as of Oct. 2020, 5 pages.

* cited by examiner

2500

Action: Import the LM data from the Control Box, if necessary.

Press the appropriate button.

| Skip | Import |

2600

Read the smallest line you can see clearly on the chart.

```
K O R D H  30
N V D O K  25
O N R K D  20
```

Select the smallest line from which the patient can read 3 or more letters.

| 30 | 25 | 20 | None |

710

SYSTEMS AND METHODS FOR AUTOMATED SUBJECTIVE REFRACTIONS

CROSS-REFERENCE TO RELATED APPLICATIONS

This application is a continuation of U.S. patent application Ser. No. 17/022,539, filed Sep. 16, 2020, which claims the benefit of and priority to U.S. Patent Application No. 62/901,691, filed Sep. 17, 2019, entitled "SYSTEMS AND METHODS FOR AUTOMATED SUBJECTIVE REFRACTIONS," which are incorporated herein by reference in their entireties.

TECHNICAL FIELD

The present disclosure relates generally to systems and methods for assessing vision. More specifically, the present disclosure relates to systems and methods for administering subjective refraction tests to patients.

BACKGROUND

Refraction tests are commonly administered as part of a routine eye examination and are intended to identify the prescription that a patient requires in corrective lenses in order to achieve optimum vision, which is typically considered to be twenty-twenty (20/20). Patients that do not have 20/20 vision have a condition known as a refractive error. A refractive error indicates that light is not properly refracted as it passes through the lens of the patient's eye, thus requiring a corrective lens in order to correct the refraction of the light. It has been determined that corrective lenses that allow a patient to achieve vision greater than 20/20, for example 20/15, strain various muscles and components of the eye which may cause distress to the patient. Accordingly, refraction tests are commonly administered to determine which strength of corrective lenses a patient requires in order for the patient to achieve 20/20 vision. At the conclusion of a refraction test, a medical professional (e.g., a Doctor of Optometry or O.D.) will review the results of the test. The medical professional will then guide the patient toward the proper corrective lenses relative to patient's results of the refraction test.

SUMMARY

At least one embodiment relates to a system for administering a subjective refraction test on a patient. The system includes a phoropter having a plurality of lenses that are adjustable to affect the vision of the patient to administer a plurality of sub-tests of the subjective refraction test, a display device configured to display a plurality of visual references viewable by the patient through the plurality of lenses of the phoropter, and a computing device coupled to the phoropter and the display device. The computing device is configured to generate and display a script corresponding to a first set of conditions for a first sub-test of the plurality of sub-tests, the first set of conditions corresponding to a first visual reference viewed by the patient through a first combination of the plurality of lenses of the phoropter, the script being displayed for reading by a technician to the patient, receive an input indicative of the patient's vision under the first set of conditions, determine an endpoint for the first sub-test of the plurality of sub-tests based on the input, communicate a signal to the phoropter and the display device causing the patient to be presented with a second set of conditions to administer a second sub-test of the plurality of sub-tests in response to the input, the second set of conditions including a second visual reference viewed by the patient and a second combination of the plurality of lenses of the phoropter, generate and display an updated script corresponding to the second set of conditions, wherein the updated script provides a prompt for updated patient feedback under the second set of conditions, and receive an updated input corresponding to the updated patient feedback.

In certain embodiments, the computing device is configured to determine an endpoint for the second sub-test based on the updated input, and to subsequently administer a third sub-test of the plurality of sub-tests.

In certain embodiments, the first set of conditions and the second set of conditions include a combination of subjective lenses and auxiliary lenses of the phoropter.

In certain embodiments, the computing device is configured to display the script and the updated script on a user interface, wherein the script and the updated script are configured to be understandable by a technician who is not a medical professional.

In certain embodiments, the first set of conditions includes a first combination of auxiliary lenses, a first combination of subjective lenses, and the first visual reference, and the second set of conditions includes one of a second combination of auxiliary lenses different from the first combination of auxiliary lenses, a second combination of subjective lenses different from the first combination of subjective lenses, or the second visual reference different from the first visual reference.

In certain embodiments, the system further includes a control box configured to enable wireless communication between one or more of the computing device, the display device, and the phoropter.

In certain embodiments, the determination of an endpoint for a given sub-test of the plurality of sub-tests corresponds to a determination that additional patient input is not required for the given sub-test.

In certain embodiments, the determination of an endpoint for third sub-test of the plurality of sub-tests corresponds to receiving a predetermined number of replies from the patient based on a set of conditions for the third sub-test.

In certain embodiments, at least one of the plurality of sub-tests includes a non-optimum endpoint indicating a visual acuity of the patient not meeting or reaching a predefined value.

In certain embodiments, the first set of conditions and the second set of conditions include various combinations of subjective lenses and auxiliary lenses of the phoropter as well as various visual references displayed by the display device.

Another example embodiments relates to a method of administering a subjective refraction test to a patient. The method includes providing, by a computing device, a script for administering a sub-test of a plurality of sub-tests of the subjective refraction test, the script corresponding to a first set of conditions include a first visual reference viewed by the patient through a first combination of a plurality of lenses of a phoropter, displaying, via a display device based on a signal from the computing device, the first visual reference for viewing by the patient as part of administering the sub-test of the plurality of sub-tests, adjusting, via the phoropter based on a signal from the computing device, the plurality of lenses to implement the first combination of the plurality of lenses as part of the sub-test of the plurality of sub-tests, receiving, by the computing device, an input corresponding to patient feedback indicative of the patient's vision under the first set of conditions, determining, by the computing device, a second set of conditions in response to the patient feedback as part of the sub-test, the second set of conditions including a second visual reference, a change to at least one lens in the first combination of the plurality of lenses, and an updated script, controlling, by the computing device, the phoropter in accordance with the change to the at least one lens in the first combination of the plurality of lenses, controlling, by the computing device, the display device to provide the second visual reference, and displaying, by the computing device, the updated script.

In certain embodiments, the method further includes concluding that the subjective refraction test is complete once an endpoint has been determined for the sub-test.

In certain embodiments, the method further includes displaying, via the computing device, one or more user interfaces including the script and the updated script.

In certain embodiments, the plurality of lenses of at least one of the first and second sets of conditions include a combination of subjective lenses and auxiliary lenses of the phoropter.

In certain embodiments, the first combination of the plurality of lenses includes a first set of auxiliary lenses or a first set of subjective lenses, wherein the second combination of lenses includes a second set of auxiliary lenses or a second set of subjective lenses, and wherein the at least one of the first set of auxiliary lenses differs from the second set of auxiliary lenses or the first set of subjective lenses differs from the second set of subjective lenses.

In certain embodiments, the method further includes determining an endpoint for the sub-test based on determining a visual acuity value matching a predefined value.

In certain embodiments, the predefined value is twenty-twenty.

In certain embodiments, the method further includes determining an endpoint for the sub-test based on receiving a predefined number of patient answers to questions provided in the script and updated script.

Another example embodiment relates to a system for administering an automated subjective refraction test to a patient. The system includes a processing circuit coupled to a phoropter having a plurality of lenses that are adjustable and a display device configured to display a plurality of visual references viewable through lenses of the phoropter. The processing circuit is configured to generate a script to display for reading by a technician as part of a first sub-test of the automated subjective refraction test, the script corresponding to a first set of test conditions corresponding to a first combination of the lenses and a first visual reference, controlling the phoropter to implement the first combination of the lenses, controlling the display device to display the first visual reference, receiving a first input corresponding to patient feedback regarding the patient's vision under the first set of test conditions, determining a second set of conditions regarding a second sub-test of the automated subjective refraction test, the second set of conditions including either a second combination of the lenses or a second visual reference based on the first input, generating an updated script to display corresponding to the second set of conditions, and at least one of controlling the phoropter to implement the second combination of lenses or controlling the display device to display the second visual reference.

In certain embodiments, the processing circuit is further configured to determine an endpoint for the first sub-test of the automated subjective refraction test based on receiving a predefined number of responses regarding the patient's vision under the first set of test conditions or determining a preset visual acuity value for the patient for the first sub-test.

This summary is illustrative only and is not intended to be in any way limiting. Other aspects, inventive features, and advantages of the devices or processes described herein will become apparent in the detailed description set forth herein, taken in conjunction with the accompanying figures, wherein like reference numerals refer to like elements.

DETAILED DESCRIPTION

Figure 1:
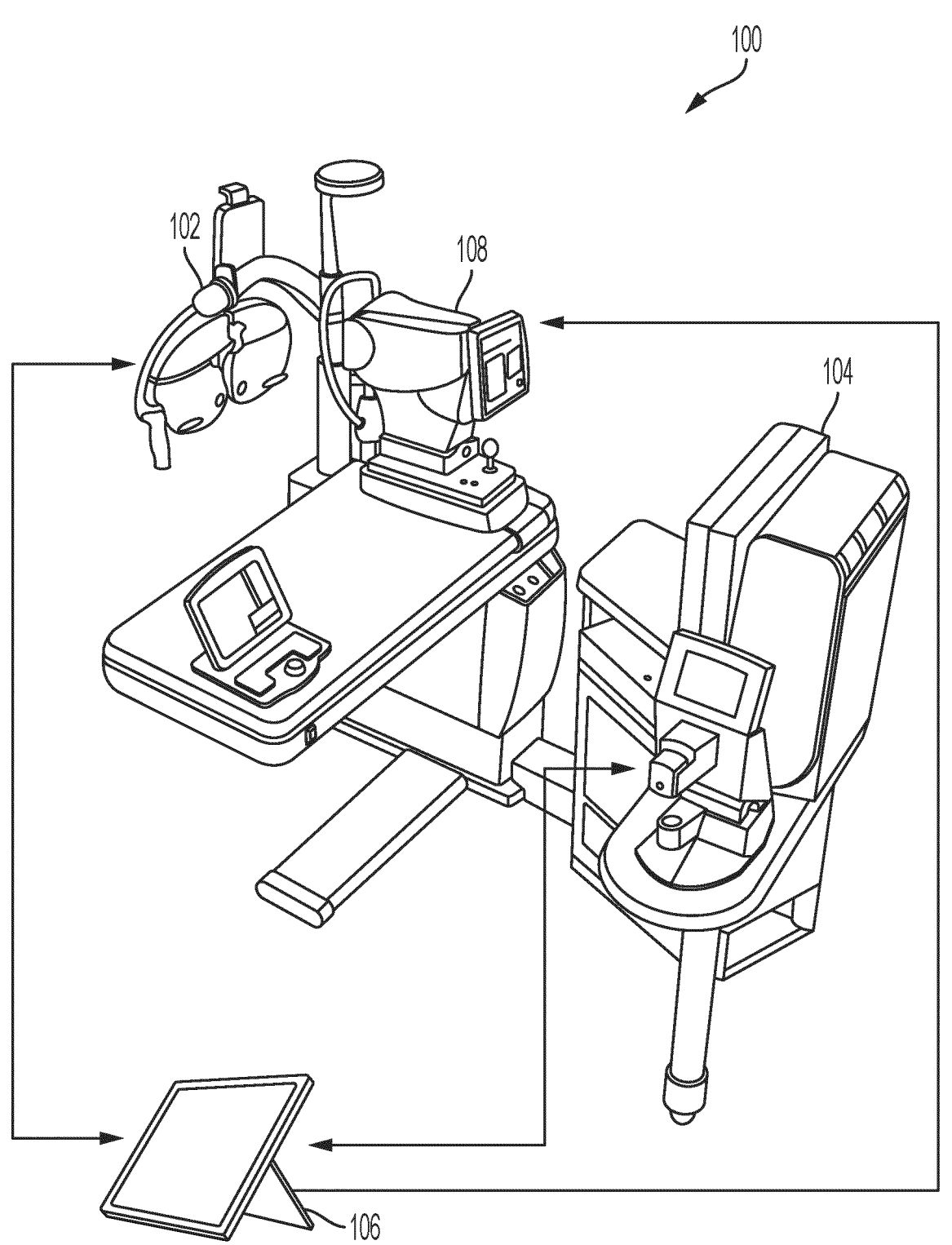
FIG. 1 is an illustration of a system for administering subjective refraction tests to a patient, according to an exemplary embodiment.

Before turning to the figures, which illustrate certain exemplary embodiments in detail, it should be understood that the present disclosure is not limited to the details or methodology set forth in the description or illustrated in the figures. It should also be understood that the terminology used herein is for the purpose of description only and should not be regarded as limiting. The construction and arrangement of the system for administering automated subjective refraction tests as shown in the various exemplary embodiments is illustrative only. Additionally, any element disclosed in one embodiment may be incorporated or utilized with any other embodiment disclosed herein.

Refraction tests can also be used to diagnose various conditions of the eye in addition to determining an appropriate strength corrective lens for a patient. For example, a refraction test can be used to diagnose conditions such as astigmatism, hyperopia, myopia, and presbyopia. Additionally, the results of a refraction test can also be a factor in the diagnosis of other conditions such as macular degeneration, retinal vessel occlusion, retinitis pigmentosa, and retinal detachment. As described previously, a patient's results of a refraction test are reviewed by a medical professional for a diagnosis, prescription, or further evaluation that patient may require.

A refraction test may include a variety of sub-tests intended to assess different aspects of the patient's vision. These sub-tests that may be administered as part of a refraction test, and include (but are not limited to) tests for far visual acuity, sphere refinement tests, axis tests, and cylinder power tests. Some of the aforementioned tests may be administered to the patient for one eye prior to being administered to a second eye (e.g., one eye is tested at a time). Additionally, other sub-tests may include a binocular balance test, phoria test, near visual acuity test, and glare tests, where such sub-tests may be administered to both eyes simultaneously. Additionally, a refraction test may also include subjective comparisons, for example showing a patient a lens corresponding to the patient's current corrective lens prescription followed by a stronger corrective lens.

A system for administering a refraction test may include a phoropter (also known as a refractor) and one or more visual references provided by a projector. The phoropter includes a pair of openings that the patient may look through, as well as lenses that may be individually placed within the pair of openings so as to affect the vision of the patient. These lenses, typically known as subjective lenses, are disposed within the phoropter and may be adjusted from the exterior of the phoropter by a mechanism such as a switch or lever (or in some applications, by remote control via a control box). The phoropter can also include additional lenses, commonly referred to as auxiliary lenses that may be positioned over top of the openings to further affect the vision of the patient. The visual references are typically configured a set distance from the phoropter, and are often of various sizes, shapes, and colors so as to facilitate the administration of various sub-tests of the refraction test. For example, the visual references may include a Snellen chart or LogMAR chart, both of which are commonly associated with eye examinations. In some refraction tests, the visual references may be displayed using physical charts, such as a Snellen chart, or may be displayed using the projector configured to display various visual references corresponding to each of the different sub-tests as they are administered.

In administering a refraction test, the patient is positioned (typically seated) adjacent the phoropter. The phoropter is arranged such that the patient may comfortably look through the openings of the phoropter at the visual reference. The visual reference is positioned such that the visual reference may be within a line of sight from the phoropter and may be viewed by the patient through the openings of the phoropter. An administrator of the refraction test, which may be a technician (e.g., non-skilled employee), a test conductor (e.g., an employee skilled in administering refraction tests), or a medical professional (e.g., a DO) will then begin the refraction test of the patient. The administrator of the test may conduct the numerous sub-tests of the refraction test firstly for a single eye. This may include closing off one of the openings of the phoropter and positioning various subjective lenses within the unclosed opening while asking the patient to identify various features of the visual references.

In some sub-tests, auxiliary lenses may be positioned on top of the subjective lenses to further affect the vision of the patient. This process may be repeated until all the sub-tests are administered for each eye individually. The test administrator may then begin conducting tests that are administered to both eyes at the same time, with the patient asked to view the visual reference through both openings of the phoropter simultaneously. The test administrator will then adjust the phoropter to individually position various subjective lenses within the openings and ask the patient to identify the visual references viewed through the subjective lenses as the various sub-tests of the refraction test are conducted.

The test administrator may ask the patient various questions in order to evaluate the patient's vision. For example, the test administrator may position a first set of subjective lenses within the openings of the phoropter, and ask the patient to view a visual reference. The test administrator may then replace the first set of subjective lenses with a second set of subjective lenses and ask the patient to again view the visual reference. The test administrator may then ask the patient if the visual reference appeared clearer when looking through the first set of subjective lenses or the second set of subjective lenses. This process and/or other similar processes may be repeated for each of the sub-tests until sufficient data has been collected for each of the sub-tests, or until a point has been reached at which no additional data can be collected from repeating the steps of a given sub-test. At that point, the test administrator will begin administering the next sub-test. This process can be repeated until each sub-test has been administered and completed.

Referring to the Figures generally, systems, apparatuses, and methods for automated subjective refraction tests are shown according to various embodiments herein. According to the present disclosure, a controller of an input device (e.g., a tablet computer) is structured to facilitate administering an automated subjective refraction test to a patient. The automated subjective refraction test may include a plurality of sub-tests as described above. The controller is configured to determine conditions to be provided by a phoropter and a display device to the patient (e.g., that depict a visual reference that the patient observes through the phoropter) and adjust the phoropter and the display device according to patient feedback. For example, the controller can communicate signals to a control box to adjust the subjective lenses of the phoropter as well as a visual reference displayed by the display device. The controller is configured to analyze inputs provided by the test administrator indicative of the vision of the patient under the various sets of conditions in order to administer the various sub-tests of the automated subjective refraction test. Based on the inputs provided by the test administrator, the controller is configured to utilize pre-determined endpoints for each of the sub-tests of the automated subjective refraction test in order to determine when to stop one sub-test and move on to the next sub-test within an overall refractions test. The automated subjective refraction test is concluded upon the determination of a pre-determined endpoint for each of the sub-tests, and the conclusion of each sub-test corresponding to each pre-determined endpoint is communicated to a medical professional. Advantageously, the controller allows for a test administrator inexperienced in refraction testing to administer the automated subjective refraction test.

Referring now to the exemplary embodiment of FIG. 1, a system 100 for administering refraction tests to patients is shown. The system 100 and the components thereof can be implemented to administer automated subjection refraction tests to patients. In some embodiments, the system 100 may be operated at least in part by a test administrator. For example, the test administrator may provide basic instructions to a patient in order to properly position the patient. The test administrator may also perform various tasks, such as ensuring that power is supplied to the necessary components of the system 100 such that all components may function correctly. The test administrator may not have expertise with the equipment of the system 100 or in-depth knowledge of refraction testing or automated subjective refraction testing.

Figure 2:
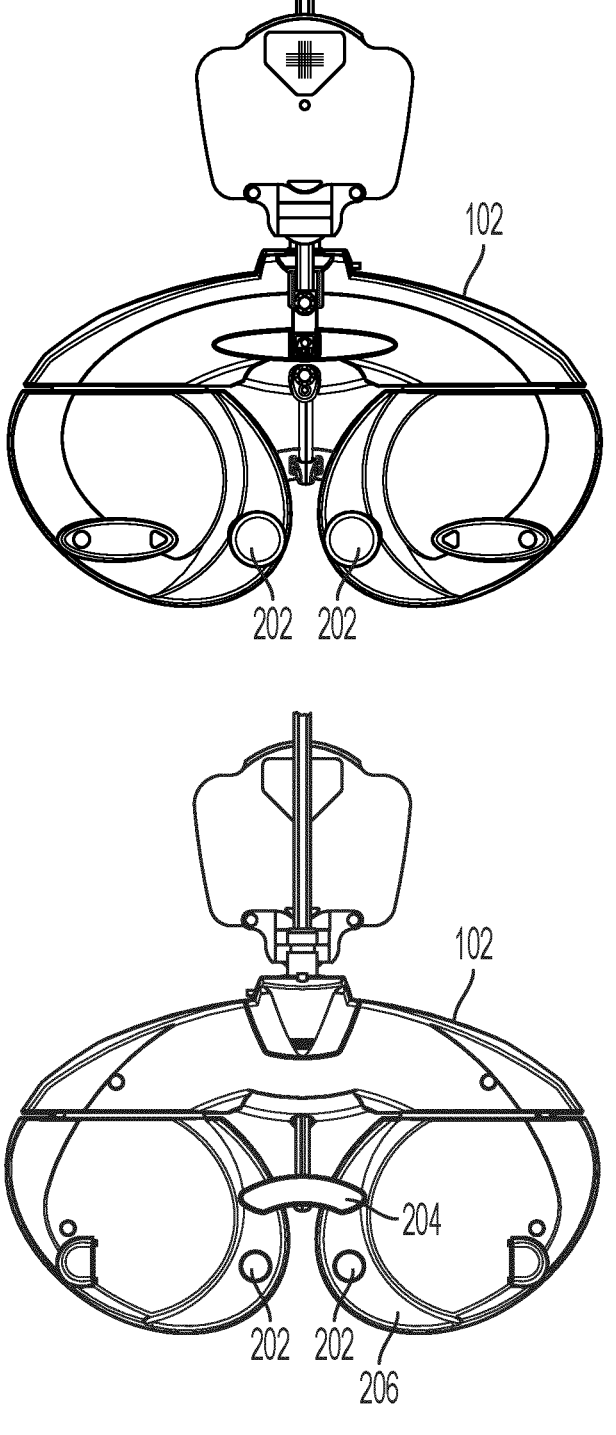
FIG. 2 is an illustration of a phoropter, also known as a refractor, of FIG. 1, according to an exemplary embodiment.
Figure 3:
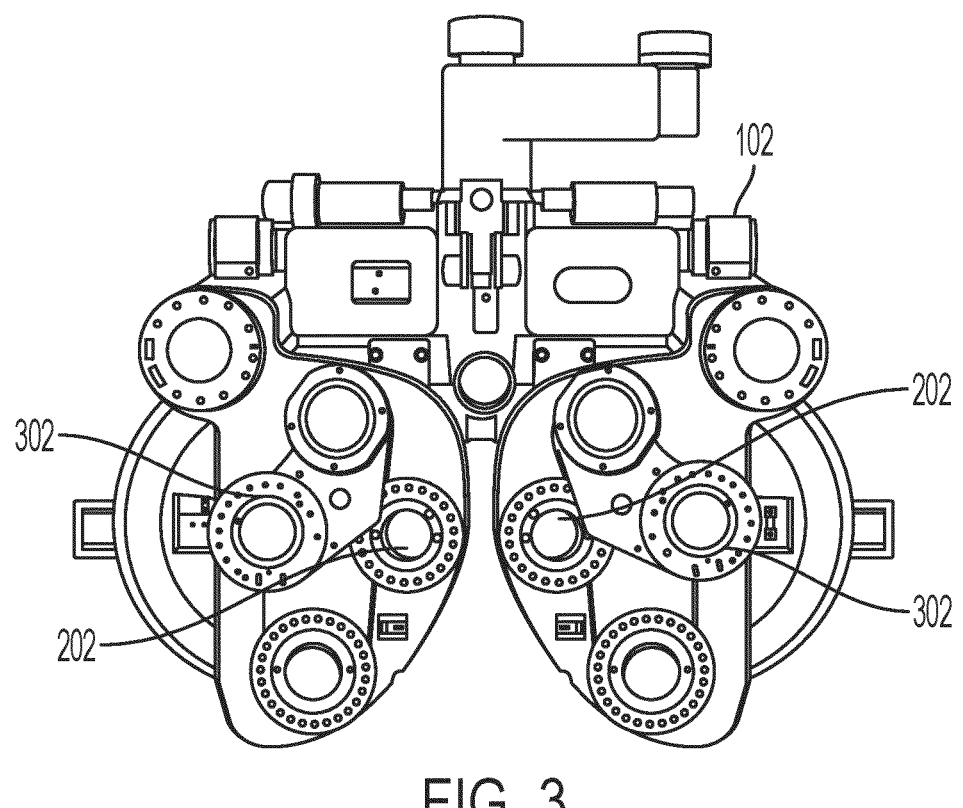
FIG. 3 is an additional illustration of the phoropter of FIG. 1, according to an exemplary embodiment.

With reference to FIGS. 1-3, the system 100 is shown to include a phoropter 102, a display device 104, an input/output device 106 (referred to as input device for brevity herein), and a control box 108, as shown in the exemplary embodiment of FIG. 1. The phoropter 102 is coupled to the control box 108. The control box 108 may be configured to adjust, change, or otherwise control the phoropter 102. In particular, the control box 108 is structured to manipulate or change the subjective lenses (not shown) of the phoropter 102 positioned within openings 202 as shown in the exemplary embodiment of FIG. 2. The control box 108 is structured to rotate, move, or otherwise control the subjective lens disposed or positioned within each opening 202 of the phoropter 102. The phoropter 102 also includes auxiliary lenses 302, as shown in the exemplary embodiment of FIG. 3. The auxiliary lenses 302 may be also be adjusted, change, moved, or otherwise manipulated by the control box 108. Additionally, in some embodiments, the auxiliary lenses 302 may be configured to be manually adjusted by a test administrator, or by a medical professional.

The phoropter 102 is also shown to include a forehead rest 204 and a face shield 206, as shown in the exemplary embodiment of FIG. 2. Prior to beginning the automated subjective refraction test, the test administrator may provide basic instructions to the patient and/or help the patient be seated adjacent the phoropter 102. The test administrator may then adjust the phoropter 102 and/or components thereof such that the forehead rest 204 is properly positioned contacting the forehead of the patient. Additionally, the test administrator may ensure that the position of the patient allows the patient to view the display device 104 through the openings 202 of the phoropter 102. This may include adjusting the height of the phoropter 102 and/or adjusting other components, such as the position of the forehead rest 204 of the phoropter 102 or the height of a chair in which the patient is seated. The test administrator may also ask the patient if s/he can view a visual reference used, which may be used to establish proper position of the phoropter 102 and the components thereof. The steps taken by the test administrator as described previously may be communicated to the test administrator via instructions provided on the input device 106. For example, the test administrator may be instructed to ensure the patient is properly positioned and then to provide a confirmation input to the input device 106. In response to the confirmation input provided to the input device 106 by the test administrator, the input device 106 may then present additional instructions to the test administrator corresponding to preparation and administration of the automated subjective refraction test described herein (e.g., obtaining and entering basic information from the patient, determining if the patient currently wears corrective lenses, etc.).

The display device 104 is a component of the system 100 and can be coupled to one or more of the other components of the system 100 such as the control box 108, for example. The display device 104 is configured to display a visual reference to the patient on a screen thereof, with the screen positioned such that the patient may view the screen and the corresponding visual reference displayed while positioned before the phoropter 102 and looking through the openings 202 of the phoropter 102. The display device 104 is configured to be in communication with one or more of the devices of the system 100, for example the input device 106 and the control box 108 such that the display device 104 may receive signals or other data causing the display device 104 to display different visual references to the patient. For example, the patient may provide feedback to the test administrator indicating the patient's vision relative to a visual reference displayed by the display device 104. In response to the patient's feedback, the test administrator may provide an input to the input device 106, which may communicate a signal to the display device 104 causing the display device 104 to update the visual reference displayed to the patient. For example, if the patient was presented a line of text on the display device 104 and was able to read the line of text, the display device 104 may then display a smaller line of text. However, if the patient was unable to read the line of text, the display device 104 may display a larger line of text. Generally, in administering the automated subjective refraction test the display device 104 is configured to display visual references for viewing by the patient and update said visual references based on feedback provided by the patient to the test administrator (and subsequently the system 100) indicating the patient's vision relative to visual references displayed.

The control box 108 is coupled to the phoropter 102 such that the control box may manipulate or otherwise control the subjective lenses disposed within the phoropter 102. The control box 108 may include one or more processing components (e.g., processing circuits including one or more memory devices and processors along with any additional components, such as a communications interface) that enable the control box 108 to couple to the phoropter 102 and the input device 106, and further enable the control box 108 to at least partly control the phoropter 102. Beneficially, the control box 108 is shown to include a display screen and an input device (shown as a joystick) that enables a technician to control the phoropter and, particular, the changing in and out of lenses. Mechanical phoropters require a user to physical rotate a wheel or a like device to change in and out the lenses. This control box enables a technician to keep their arms below their shoulder to control the phoropter, which may promote long-term health of the technician.

The control box 108 is also coupled to the input device 106, such that the control box 108 may receive signals (e.g., information, data, instructions, etc.) from the input device 106. In this regard, the input device 106 (described herein below) is structured to at least partly control the phoropter 102. In this embodiment, control of the phoropter is via the control box 108 (an instruction is sent to the control box which then controls the phoropter). In other embodiments, the input device 106 may directly couple to the phoropter 102 for directly controlling the phoropter 102.

In operation, a test administrator may provide an input to the input device regarding a patient's vision given a set of conditions (e.g., a first pair of subjective lenses positioned within the openings 202 of the phoropter 102). The input device 106 may then communicate the information corresponding to the input provided by the test administrator to the control box 108. The control box 108 can be configured to receive and analyze the data communicated by the input device, and in response to said data, adjust the subjective lenses of the phoropter such that a second pair of subjective lenses are positioned within the openings 202 of the phoropter 102, which replace the first pair of subjective lenses. This process may be repeated in order to provide various different sets of conditions for the patient using various different pairs of subjective lenses positioned within the openings 202 of the phoropter 102 by the control box 108.

The auxiliary lenses 302 of the phoropter 102 are configured on a side of the phoropter 102 opposite the forehead rest 204. Additionally, the auxiliary lenses 302 may be configured such that they may be positioned between the subjective lenses disposed in the openings 202 of the phoropter 102 and the visual reference displayed by the display device 104. Accordingly, various portions of the automated subjective refraction test may include the patient viewing the visual reference through the subjective lenses, and may also include the patient viewing the visual reference through the subjective lenses and the auxiliary lenses 302. In order to provide conditions as required by portions of the automated subjective refraction test, the control box 108 may be configured to actuate the auxiliary lenses 302 such that the auxiliary lenses 302 are disposed adjacent the subjective lenses.

Figure 4:
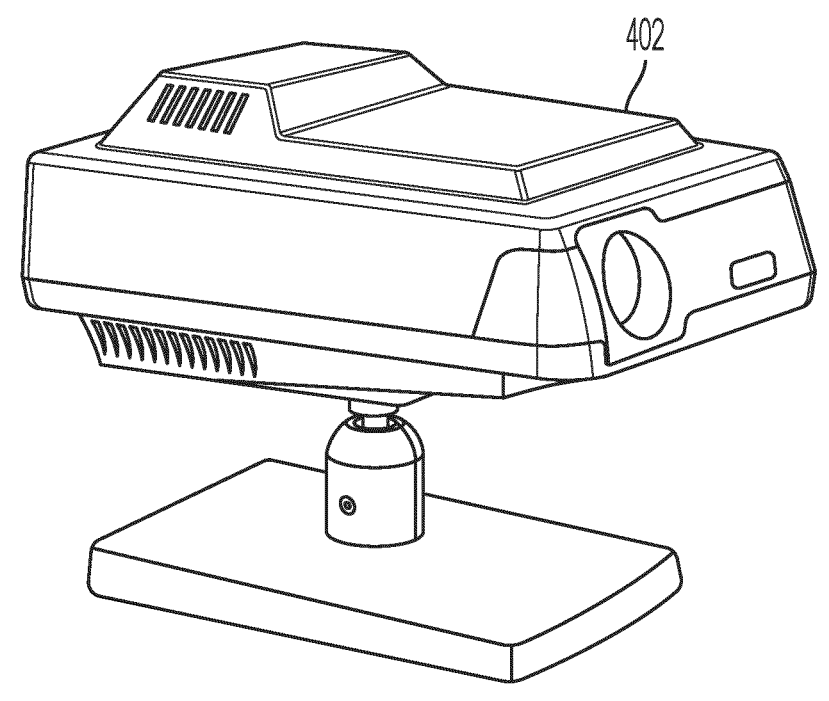
FIG. 4 is an illustration of a projector that can be used with the system of FIG. 1, according to an exemplary embodiment.
Figure 5:
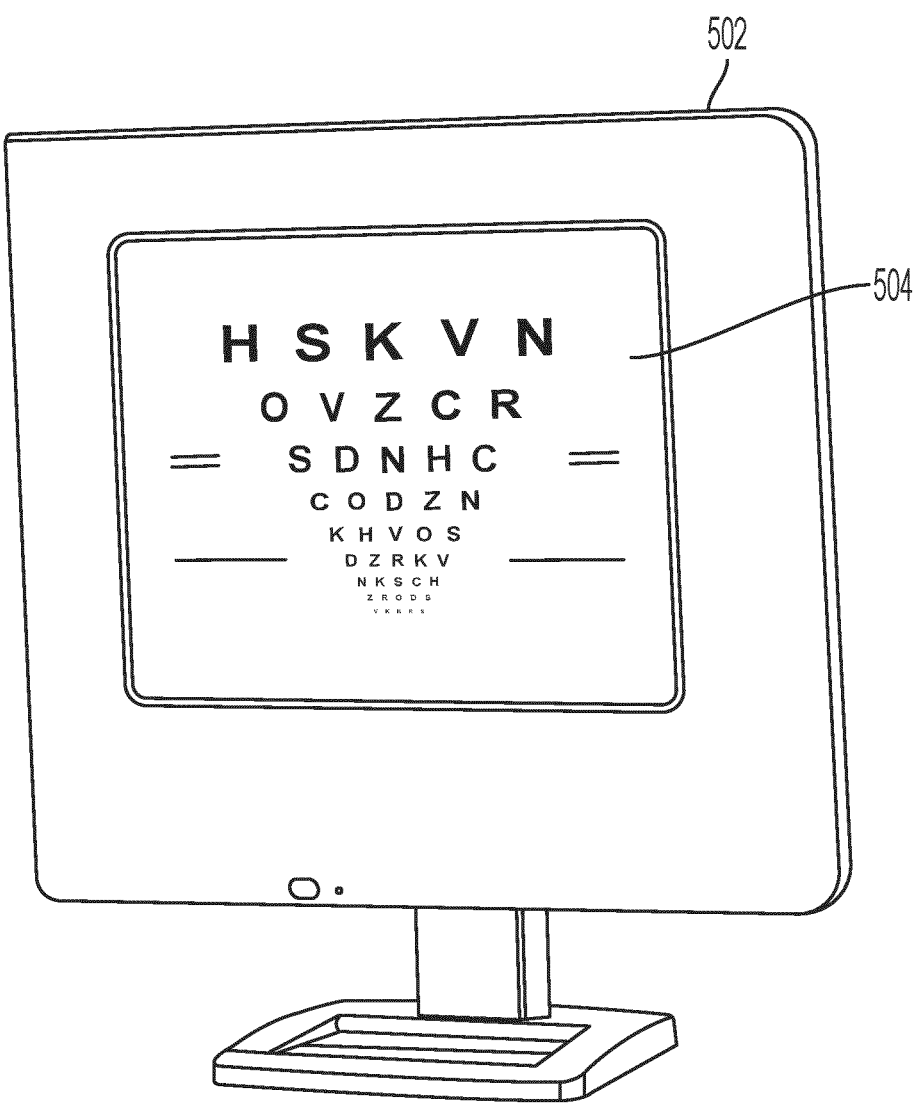
FIG. 5 is an illustration of a visual reference that can be displayed by the projector of FIG. 1, according to an exemplary embodiment.
Figure 6:
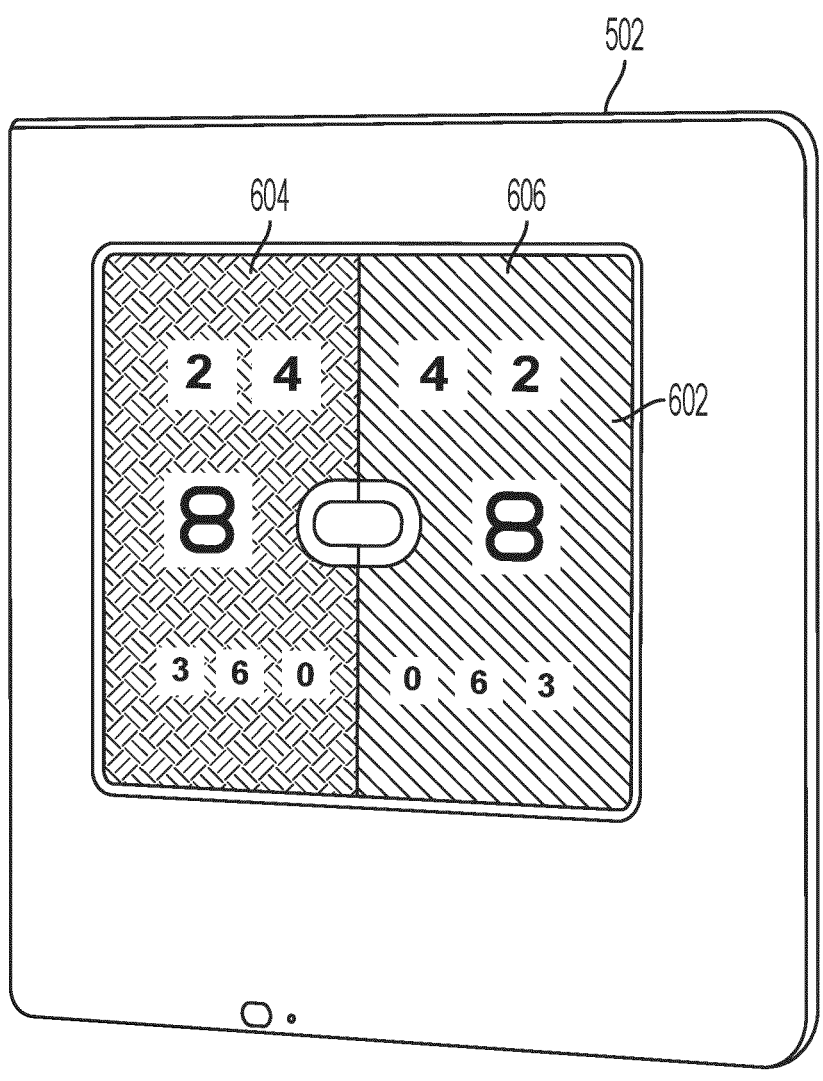
FIG. 6 is an additional illustration of a visual reference that can be displayed by the projector of FIG. 1, according to an exemplary embodiment.

When the patient is in contact or near contact with the phoropter 102 and is viewing the visual reference, the visual reference may be provided by a variety of structures. In FIGS. 1-3, a built-in projecting and display device for the visual reference is shown. This all-in-one device displays the visual reference. This all-in-one device is used with the refraction workstation of FIGS. 1-3. In contrast, FIG. 4 depicts a projector 402 where the visual reference is projected onto a screen (e.g., a metal screen) (i.e., not an all-in-one device). Further, FIGS. 5-6 depict a monitor that shows the visual reference. Thus, those of ordinary skill in the art will recognize and appreciate the different type of visual reference display and providing devices that may be implemented with the present disclosure.

Referring now to FIG. 4, a projector 402 is shown, according to an exemplary embodiment. The projector 402 is configured to display a visual reference that is viewed by the patient through the openings 202 of the phoropter 102 (and, accordingly, through the subjective lenses and/or the auxiliary lenses 302). For example, the projector 402 may be configured in a fixed location relative to the phoropter 102 and other components of the system 100. From the fixed location, the projector may display various visual references to the patient, such as a Snellen chart. Based on the patient's ability to identify the visual reference and any features thereof, the test administrator may provide an input to the input device 106. The input device 106 may then communicate a signal to the projector 402 (and/or the display device 104) causing the projector 402 to either continue to display the same visual reference or to display an updated visual reference for viewing by the patient. The projector 402 may be implemented in conjunction with the system 100 and be configured to conjunction cooperatively with the display device 104, or may be implemented in conjunction with the system 100 instead of the display device 104.

Referring now to FIGS. 5-6, a monitor 502 is shown displaying multiple visual references, according to an exemplary embodiment. As show in FIG. 5, the monitor 502 is displaying a visual reference 504 that may be viewed by a patient through the openings 202 of the phoropter 102. The visual reference 504 as shown in FIG. 5 is the same as or similar to a Snellen chart. One or more sub-tests of the automated subjective refraction test described herein may include the test administrator asking the patient to identify characters such as those shown on the monitor 502 in FIG.

5. The visual reference 504 of the monitor 502 may then be updated in response to an input provided to the input device 106 indicating if the patient identified the visual reference 504 correctly. For example, if a patient didn't correctly identify the visual reference 504 shown in FIG. 5, the test administrator may provide an input to the input device 106 indicating as such. The input device 106 may then communicate a signal to the monitor 502 (and/or other components of a system such as the system 100) causing the monitor 502 to display an updated version of the visual reference 504. Further to the previous example, the updated visual reference may include a different or changed Snellen chart. In some embodiments, while the monitor 502 is displaying a new visual reference for viewing by the patient, other devices of a system such as the system 100 may also receive signals from the input device. For example, the control box may receive a signal causing it to manipulate the subjective lenses of the phoropter 102 such that any subjective lenses that were positioned within the openings 202 are replaced by a new set of subjective lenses. The monitor 502 may be implemented in conjunction with a projector, such as the projector 402 of FIG. 4, or may be implemented independently with a system such as the system 700 of FIG. 1.

Referring now to FIG. 6, the monitor 502 as shown in FIG. 5 is shown to display another visual reference, which is shown as visual reference 602. The visual reference 602 is shown to include a first portion 604 and a second portion 606. The first portion 604 is shown to have a different background than the second portion 606. The different background of the first portion 604 and the second portion 606 may correspond to different colors (e.g., for a sub-test in which a patient is asked to identify one or more colors) or may correspond to patterns serving as background for the characters superimposed on the first portion 604 and the second portion 606. For example, the patient may be asked to identify the characters superimposed on the first portion 604 and/or the second portion 606, with the first portion 604 and the second portion 606 having different background colors on which the characters are superimposed upon. In the example shown, the first portion 604 has a green background while the second portion 606 has a red background. Similar to the previous example discussed with reference to FIG. 5, the visual reference 602 may also be updated in response to inputs provided by a test administrator to the input device 106, which may subsequently communicate a signal to various components of a system (such as the system 100 of FIG. 1).

The visual references displayed by the display device 104 of the system 100, the projector 402, and/or the monitor 502 may vary according to the various sub-tests of a refraction test or an automated subjective refraction test. For example, as shown in FIG. 6, the visual references may include various colors or patterns and may have characters display adjacent to or superimposed on said colors or patterns. Thus, the visual reference may include any one or more of numbers, letters, symbols, and so on. Additionally, for other sub-tests as described previously, the visual reference displayed may be adapted, for example to a Snellen chart as shown in the exemplary embodiment of FIG. 5. In some embodiments, only the display device 104 is utilized. In other embodiments, only the projector 402 or only the monitor 502 are utilized. In still other embodiments, the projector 402 and monitor 502 may be utilized together. In any configuration, a visual reference that is viewable through the phoropter by the patient is provided on or by these components.

Generally, the components shown and described with reference to FIGS. 1-6 may be implemented to function cooperatively within a system. According, all of said components may also be configured to communicate with one another. For example, the test administrator may provide an input to the input device 106 indicating the patient's vision when presented with a first set of conditions including a pair of subjective lenses positioned in the openings 202 of the phoropter 102 (and possibly auxiliary lenses 302 positioned adjacently) and a visual reference displayed by the display device 104. The input device 106 may then communicate a signal to other devices including the control box 108 and the display device 104. The control box 108 may then manipulate or otherwise adjust the subjective lenses of the phoropter 102 such that the subjective lenses previously positioned in the openings 202 are replaced by a different set of subjective lenses. Additionally, the display device 104 may adjust the visual reference displayed as part of the first set of conditions, or may display a different visual reference entirely. The patient may then be presented a second set of conditions including different subjective lenses and/or a different visual reference, for which the patient may provide to the test administrator an indication of his/her vision and the test administrator may subsequently provide an input to the input device 106 corresponding to the indication of the patient. This process may then be repeated for one or more sub-tests of a refraction test or an automated subjective refraction test until each of the sub-tests has been completed, and accordingly, the refraction test or automated subjective refraction test is complete.

The test administrator may provide minor assistance to the patient in using the system 100 or other devices shown and described in FIGS. 1-6. For example, the test administrator may assist the patient in adjusting a seat to a proper height so that the patient may view the visual references through the openings 202 of the phoropter 102. Additionally, the test administrator may adjust the phoropter 102 and/or components thereof, such as the forehead rest 204 so as to ensure that the patient is properly positioned for a refraction test or an automated subjective refraction test. Additionally, the test administrator may receive various instructions corresponding to preparing and positioned the patient and the various equipment for a refraction test or automated subjective refraction test. For example, via the input device 106, the test administrator may receive instructions for positioning the phoropter 102 for a patient (e.g., the forehead rest 204 may be adjusted using a specific knob). The test administrator may also provide inputs to the input device 106 indicating that the patient has been positioned properly. Such inputs to the input device 106 may cause the input device 106 to communicate signals to other components of FIGS. 1-6, thus beginning the sub-tests of the automated subjective refraction test.

Figure 7:
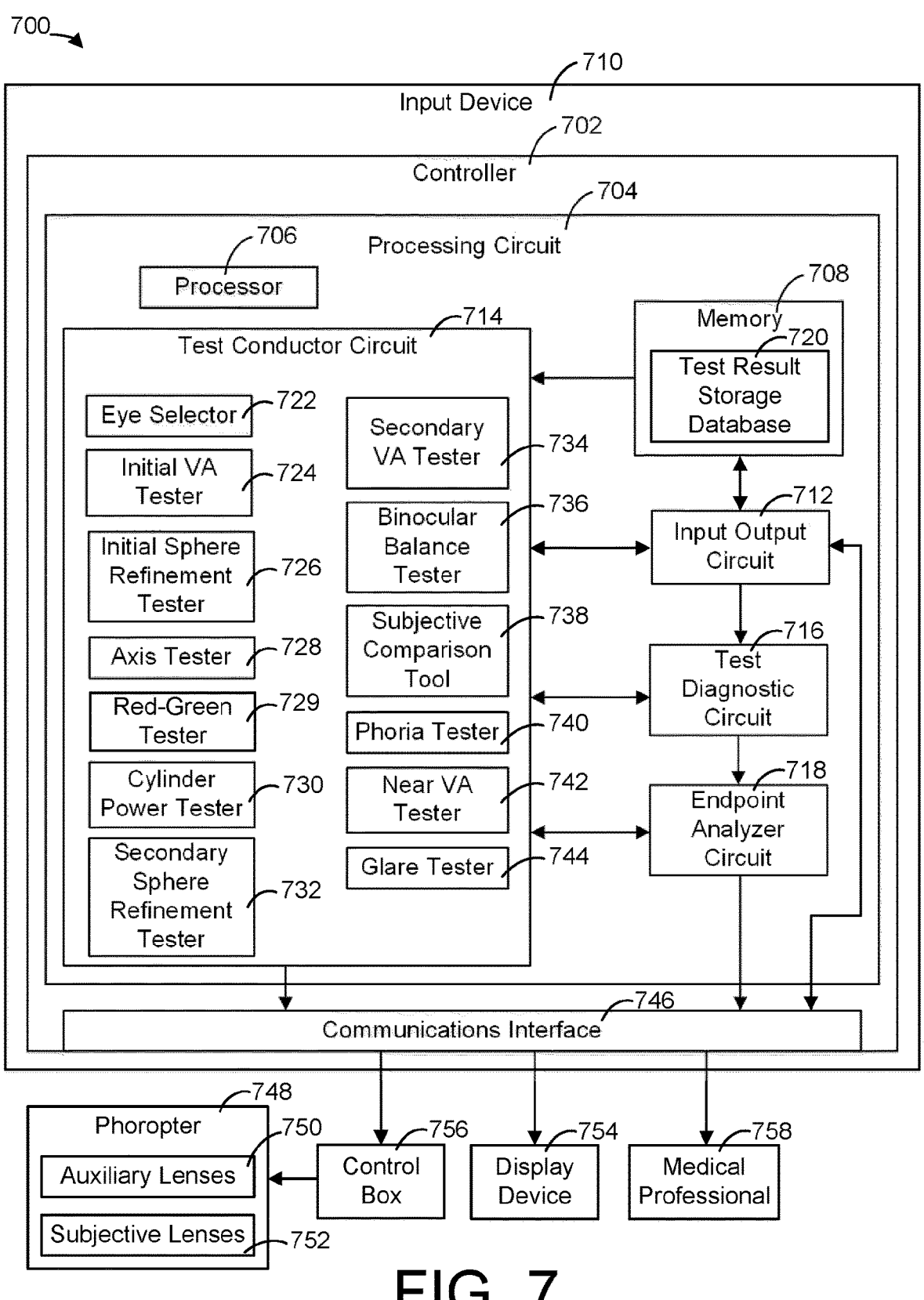
FIG. 7 is a block diagram of a system for administering automated subjective refraction testing, according to an exemplary embodiment.

Referring now to FIG. 7, a system 700 is shown for administering automated subjective refraction tests on patients. The system 700 may include some components that are the same as and/or similar to those of the system 100 as shown in FIG. 1. For example, the system 700 is shown to include a phoropter 748, which may be the same as and/or similar to the phoropter 102 of the system 100 as shown and described with reference to FIG. 1. In the example shown, the phoropter 748 is the same as the phoropter 102. The system 700 is also shown to include a display device 754 configured to provide a visual reference to the patient. The display device 754 may be the same as and/or similar to the display device 104 as shown in FIG. 1, or may include other devices/components configured to display a visual reference to the patient (e.g., a projector, a monitor, or a screen). In this example, the display device 754 is the same as display device 104. The system 700 includes a control box 756, which can be configured to actuate one or more components of the phoropter 748, and may be the same as or similar to the control box 108 as shown and described in FIG. 1. In the example shown, the control box 756 is the same as the control box 108. The system 700 is shown to include an input output device 710, referred to for brevity as input device 710, which may be the same as and/or similar to the input device 106 of the system 100 as shown and described with reference to FIG. 1

Typically, on one hand, administering refraction tests is an extremely skillful art requiring substantial sums of training. On the other hand, optometrists and ophthalmologists are often considered over-skilled for performing a refraction test. Beneficially, the system 700 may be configured to accommodate test administrators having various levels of expertise in optometry and ophthalmology (from zero experience to a skilled optometrist). In this regard and advantageously, the system 700 is structured such that an unskilled technician lacking expertise in optometry or ophthalmology may administer a test to a patient. However, the system 700 is also structured to accommodate administration of the test by medical professionals, such as a Doctor of Optometry (O.D.).

The input device 710 is shown to include a controller 702 including a processing circuit 704 and a communications interface 746. The processing circuit 704 is shown to include a processor 706 and a memory 708. The processor 706 can be implemented as a general-purpose processor, an application specific integrated circuit (ASIC), one or more field programmable gate arrays (FPGAs), a group of processing components, or other suitable electronic processing components. The processing circuit 704 is also shown to include a test conductor circuit 714 (and various testers thereof), an input output circuit 712, a test diagnostic circuit 716, and an endpoint analyzer circuit 718. The input device 710 and particularly, the controller 702, is shown and structured to manipulate multiple parameters of the automated subjective refraction test including a script provided to the test administrator by the input device 710 (e.g., via a GUI), the subjective lenses 752 and/or auxiliary lenses 750 of the phoropter 748, and the visual reference displayed by the display device 754. Over the course of the various sub-tests of the automated subjective refraction test as described previously, said parameters may be repeatedly updated and/or manipulated by the controller 702.

In one configuration, the test conductor circuit 714 (and various testers thereof), the input/output circuit 712, the test diagnostic circuit 716, and the endpoint analyzer circuit 718 are embodied as machine or computer-readable media storing instructions that are executable by a processor, such as processor 706. As described herein and amongst other uses, the machine-readable media facilitates performance of certain operations to enable reception and transmission of data. For example, the machine-readable media may provide an instruction (e.g., command) to, e.g., acquire data. In this regard, the machine-readable media may include programmable logic that defines the frequency of acquisition of the data (or, transmission of the data). The computer readable media may include code, which may be written in any programming language including, but not limited to, Java or the like and any conventional procedural programming languages, such as the "C" programming language or similar programming languages. The computer readable program code may be executed on one processor or multiple remote processors. In the latter scenario, the remote processors may be connected to each other through any type of network (e.g., CAN bus).

In another configuration, the test conductor circuit 714 (and various testers thereof), the input output circuit 712, the test diagnostic circuit 716, and the endpoint analyzer circuit 718 may be embodied as one or more circuitry components including, but not limited to, processing circuitry, network interfaces, peripheral devices, input devices, output devices, sensors, etc. In some embodiments, the test conductor circuit 714 (and various testers thereof), the input output circuit 712, the test diagnostic circuit 716, and the endpoint analyzer circuit 718 may take the form of one or more analog circuits, electronic circuits (e.g., integrated circuits (IC), discrete circuits, system on a chip (SOCs) circuits, microcontrollers), telecommunication circuits, hybrid circuits, and any other type of "circuit." In this regard, the test conductor circuit 714 (and various testers thereof), the input output circuit 712, the test diagnostic circuit 716, and the endpoint analyzer circuit 718 may include any type of component for accomplishing or facilitating achievement of the operations described herein. For example, a circuit as described herein may include one or more transistors, logic gates (e.g., NAND, AND, NOR, OR, XOR, NOT, XNOR), resistors, multiplexers, registers, capacitors, inductors, diodes, wiring, and so on). The test conductor circuit 714 (and various testers thereof), the input output circuit 712, the test diagnostic circuit 716, and the endpoint analyzer circuit 718 may also include programmable hardware devices such as field programmable gate arrays, programmable array logic, programmable logic devices or the like. The test conductor circuit 714 (and various testers thereof), the input output circuit 712, the test diagnostic circuit 716, and the endpoint analyzer circuit 718 may include one or more memory devices for storing instructions that are executable by the processor(s) of the test conductor circuit 714 (and various testers thereof), the input output circuit 712, the test diagnostic circuit 716, and the endpoint analyzer circuit 718. The one or more memory devices and processor(s) may have the same definition as provided below with respect to the memory 708 and processor 706. In some hardware unit configurations, the test conductor circuit 714 (and various testers thereof), the input output circuit 712, the test diagnostic circuit 716, and the endpoint analyzer circuit 718 may be geographically dispersed throughout the input device 710 and/or other components of the system 700. Alternatively and as shown, the test conductor circuit 714 (and various testers thereof), the input output circuit 712, the test diagnostic circuit 716, and the endpoint analyzer circuit 718 may be embodied in or within a single unit/housing, which is shown as the controller 702.

In the example shown, the controller 702 includes the processing circuit 704 having the processor 706 and the memory 708. The processing circuit 704 may be structured or configured to execute or implement the instructions, commands, and/or control processes described herein with respect to the test conductor circuit 714 (and various testers thereof), the input output circuit 712, the test diagnostic circuit 716, and the endpoint analyzer circuit 718. The depicted configuration represents the test conductor circuit 714 (and various testers thereof), the input output circuit 712, the test diagnostic circuit 716, and the endpoint analyzer circuit 718 as machine or computer-readable media. However, as mentioned above, this illustration is not meant to be limiting as the present disclosure contemplates other embodiments where the test conductor circuit 714 (and various testers thereof), the input output circuit 712, the test diagnostic circuit 716, and the endpoint analyzer circuit 718 or at least one circuit of the test conductor circuit 714 (and various testers thereof), the input output circuit 712, the test diagnostic circuit 716, and the endpoint analyzer circuit 718 is configured as a hardware unit. All such combinations and variations are intended to fall within the scope of the present disclosure.

The memory 708 (e.g., memory, memory unit, storage device, etc.) can include one or more devices (e.g., RAM, ROM, Flash memory, hard disk storage, etc.) for storing data and/or computer code for completing or facilitating the various processes, layers and modules described in the present application. The memory 708 can be or include volatile memory or non-volatile memory. The memory 708 can include database components, object code components, script components, or any other type of information structure for supporting the various activities and information structures described in the present application. According to some embodiments, the memory 708 is coupled to the processor 706 and includes computer code for executing one or more processes described herein.

As shown, the input device 710 is the same as the input device 106. The input device 710 is configured to receive inputs from a test administrator and communicate the received inputs to other components of the system 700 (e.g., to the phoropter 102 directly or via the control box 108, to the display device or projector, etc.). In some embodiments, the input device 710 may include a touch screen so as to allow the test administrator to directly interact with a user interface displayed on the input device 710. The input device 710 is also configured to display various instructions to the test administrator for administering the automated subjective refraction test to a patient (e.g., a script that the test administrator reads aloud to the patient while administering the refractions test). In some embodiments, the input device 710 may be configured as an all-in-one device configured to include one or more components of the system 700 and perform the corresponding functions and operations.

Figure 30:
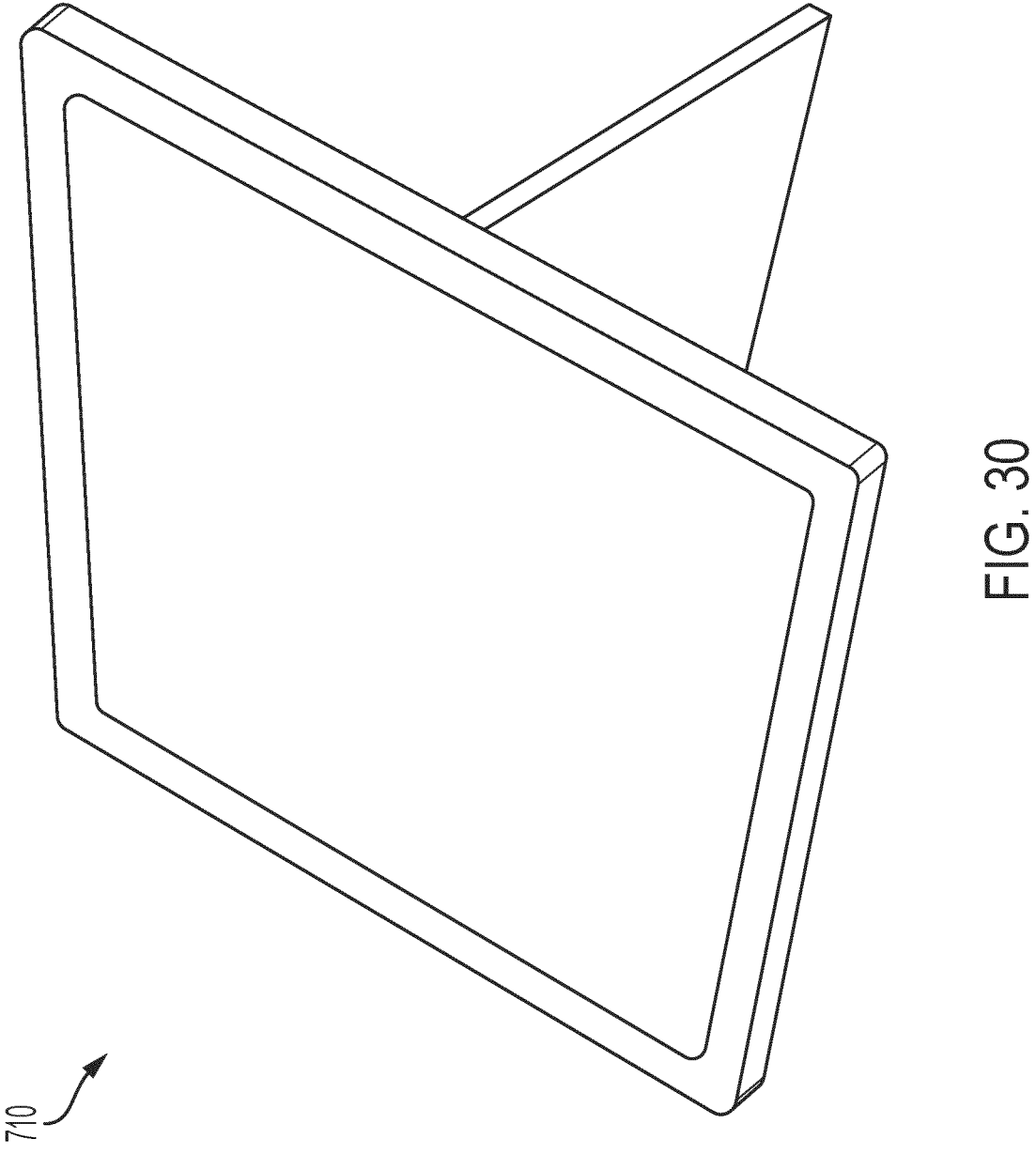
FIG. 30 is an illustration of an input output device that can be implemented in conjunction with the system of FIG. 7, according to an exemplary embodiment.

In the example shown, the input device 710 is structured as a tablet computer. FIG. 30 depicts an example input device 710, shown as the tablet computer. However, the input device 710 may also be a smartphone, laptop computer, or other computing device such as a desktop computer. The input device 710 is structured to communicate via any wired or wireless connection with one or more components of the system 700. For example, a wired connection may include a serial cable, a fiber optic cable, a CAT5 cable, or any other form of wired connection. In the example shown, the input device 710 is wirelessly coupled with one or more other components of the system 700 and, in particular, the control box 756. The wireless connection may be Bluetooth, Wi-Fi, or any other type of wireless connection. In other embodiments, a combination of wired and wireless connections may be used. For example, in another embodiment, the input device 710 may be wired to a relay box of the phoropter 102. The relay box (not shown) refers to the brains/control feature of the phoropter. This configuration may be utilized when a control box is not utilized in the refraction set up.

The input device 710 is structured to receive, transmit, and otherwise exchange data, information, and the like with various components. For example, the input device 710 may receive a graphic user interface (GUI) from the controller 702, which may include instructions for the test administrator. For example, the input device 710 may receive data from the controller 702 to display a GUI instructing the test administrator to select the location that the test is being administrated (i.e., the location of the test equipment to be used). In this example, the input device 710 may be configured to remotely control multiple sets of testing equipment (e.g., a phoropter 748, a monitor 502, etc.) located at various locations (e.g., in different cities, states, countries or even in different rooms within a same building). The input device 710 may then display a GUI that allows the operator to input (e.g., select from a drop down list, type in, select from a map, etc.) the location of the testing equipment. Once the location is input into the input device 710, the controller 702 may control some or all of the testing equipment at the chosen location. Further, the input device 710 may receive data from the controller 702 to display a GUI instructing the test administrator to position the patient in front of the phoropter 748 and ensure that the patient is able to see through the two openings of the phoropter 748 in the direction of the visual reference, as described previously in administering a refraction test to a patient. Once the test administrator confirms that the patient is positioned properly and the test may begin, the test administrator may provide an input to the input device 710 indicating that the patient is positioned correctly, with that data communicated back to the controller 702. Additionally, as the test administrator begins the refraction test, the input device 710 can receive updated GUIs that correspond to various steps that must be taken to administer the sub-tests of the refraction test. For example, the input device 710 may receive a GUI from the controller 702 instructing the test administrator to ask the patient to identify a visual reference through the openings of the phoropter 748, which may be occupied by one or more subjective lenses. The GUI may include a script including a string of text corresponding to the visual reference and the subjective and/or auxiliary lenses, with the script configured to be read by the test administrator to the patient. The script can be generated and configured such that the patient is given a limited number of response options rather than asked for open-ended feedback (e.g., "what does the top line of text say?" or "which option looks better, option 1 or option 2?"). Once the patient attempts to identify the visual reference to the test administrator, the test administrator may provide an input to the input device 710 indicating that the patient either did or did not identify the visual reference correctly. The input provided to the input device 710 by the test administrator may be communicated to the controller 702 for processing and analysis, and an updated GUI may be communicated to the input device 710 including instructions for the test administrator. The updated GUI may instruct the test administrator to ask the patient to identify another visual reference through the lenses of the phoropter 748, for example, and provide an input to the input device 710 indicative of the patient's ability to identify the visual reference. This process may be repeated for multiple sub-tests of the refraction test until the refraction test is completed.

In FIG. 7, the controller 702 is shown as a separate component relative to the input device 710. This depiction is shown for clarity. In operation and in the example shown, the controller 702 is included with the input device 710. Accordingly, the components of the controller 702 may be dedicated components of the controller 702 or shared with the input device 710 (e.g., the processing circuit 704 may also execute other operations on the input device rather than the refraction test described herein below). Due to being included with the input device 710, actions of the controller 702 may also be described herein with respect to the input device 710. With the above in mind, the controller 702 is shown to include various components described in detail below.

The processing circuit 704 is shown to include an input/output circuit 712 (or input output circuit 712). The input output circuit may be configured to communicate with a user (e.g., a test administrator/technician) of the input device 710 and/or other components of the system 700. The input output circuit 712 may be configured to receive data from an operator (e.g., test administer) of the input device 710. For example, the input output circuit 712 may receive data corresponding to the feedback provided by the patient regarding the patient's vision given a set of conditions (e.g., a combination of a set of the subjective lenses 752 of the phoropter 748 and a specific visual reference). The input output circuit 712 is structured to process said data. For example, the test administrator may provide an input to the input device 710 indicating that the patient correctly identified the visual reference given a set of conditions. The input output circuit 712 may process the data received by the input device 710 indicating the patient's correct identification of the visual reference as well as the corresponding conditions, and communicate said data to a test conductor circuit 714. The test conductor circuit 714 is shown to include a variety of test logic/routines (e.g., modules, instruction sets, etc.) configured to conduct various sub-tests of the automated subjective refraction test described herein.

The input output circuit 712 is structured to determine if the test administrator has not correctly administered a portion of an overall automated subjective refraction test. For example, if the test administrator fails to provide an input to the input device 710 displaying a GUI associated with the sub-refraction test, the input output circuit 712 may communicate a signal to the test conductor circuit 714 indicating that an input has not been received from the test administrator. Accordingly, the controller 702 may generate an updated GUI to be displayed to the test administrator via the input device 710 providing further instructions for administering the sub-test of the automated subjective refraction test. In another example, the test administrator may receive, from the controller 702, a GUI instructing the test administrator to position the patient in front of the phoropter 748 such that the patient can view the visual reference through the openings of the phoropter 748. However, if the controller 702 does not receive a confirmation from the test administrator that the patient is positioned correctly, the input output circuit 712 may be configured to cause the controller 702 to communicate a second GUI provided on the input device 710 including further instructions for positioning the patient properly in front of the phoropter 748.

The input output circuit 712 is structured to sort or otherwise organize data received by the input device 710, for example from the test administrator via a GUI displayed by the input device 710. As mentioned previously, data received by the input device 710 from inputs provided by the test administrator indicative of the patient's visual performance under various sets of conditions can be communicated to the test conductor circuit 714. However, given that the system 700 may be used to administer automated subjective refraction tests on multiple patients and may be operated by multiple test administrators (albeit, not at the same time), the input output circuit 712 may be configured to identify data corresponding to automated subjective refraction tests administered by specific test administrators or administered to specific patients. For example, the input output circuit 712 may be configured to identify all data corresponding to automated subjective refraction tests administered by specific test administrators so as to evaluate performance of given test administrators based on the data collected.

The test conductor is shown to include multiple test modules referred to as "testers" configured to administer the sub-tests of the automated subjective refraction test. Each of the "testers" as shown in the exemplary embodiment of FIG. 7 correspond to a specific sub-test of the automated subjective refraction test that can be administered by the system 700. In some embodiments, the sub-tests of the automated subjective refraction test may be repeated, for example for a test that is conducted on a single eye at a time. Additionally, the sub-tests may be conducted in various sequences depending on the patient and the feedback provided by the patient and received by the test conductor circuit 714 and the various testers thereof.

The test conductor circuit 714 and the testers thereof are shown to be in communication with the input output circuit 712, where the input output circuit 712 may communicate data received from the test administrator. For example, the test administrator may provide an input to the input device 710, with the data corresponding to that input communicated to the input output circuit 712, and then ultimately to the test conductor circuit 714. The test conductor circuit 714 is configured to receive data corresponding the automated subjective refraction test being administered to the patient. For example, the data received by the test conductor circuit 714 may include data indicating that the patient is properly positioned before the phoropter 748 and that the first sub-test may begin. Upon receipt of said data, the test conductor circuit 714 may be configured to communicate to a given tester corresponding to the first sub-test of the automated subjective refraction test that the first sub-test may begin. In another example, the data received by the test conductor circuit 714 may be indicative of a patient's vision given a set of conditions of a specific sub-test. Accordingly, the test conductor circuit 714 may communicate said data to the tester corresponding to the given sub-test, allowing the given tester to determine the next steps for the given sub-test relative to the data received.

The automated subjective refraction test may be administered by the controller 702 using various components of the system 700. Accordingly, the test conductor circuit 714 includes a tester corresponding to each of the sub-tests of the automated subjective refraction test. It should be noted, however, that some automated subjective refraction tests may not incorporate all possible sub-tests, and thus may not incorporate all testers of the test conductor circuit 714. For example, a patient may have a condition for which looking at the visual reference through a specific set of subjective lenses required for a specific sub-test may cause distress (e.g., strain the eyes and associated muscles). Accordingly, such a sub-test may be skipped and the tester corresponding to the given sub-test would not be incorporated in the administration of the automated subjective refraction test.

As described previously, refraction tests include multiple sub-tests to assess various aspects of a patient's vision. The sub-tests, which correspond to the sub-tests that may be administered by the system 700 in order to administer the automated subjective refraction test, can include the following sub-tests: initial VA test, initial sphere refinement test, axis test, red-green test, cylinder power test, secondary sphere refinement test, secondary VA test, binocular balance test, phoria test, near VA test, and glare test. Accordingly, the test conductor circuit 714 is shown to include an initial VA tester 724, an initial sphere refinement tester 726, an axis tester 728, a red-green tester 729 a cylinder power tester 730, a secondary sphere refinement tester 732, a secondary VA tester 734, a binocular balance tester 736, a phoria tester 740, a near VA tester 742, and a glare tester 744. Each of the listed testers can be configured to conduct the corresponding sub-test via the system 700.

The controller 702 is shown to include a communications interface 746, as shown in FIG. 7. The communications interface 746 can be configured to facilitate communication between the input device 710 and other components of the system 700. For example, the communications interface 746 is shown to be in communication with a control box 756, which is shown to be in communication with the phoropter 748 (including the auxiliary lenses 750 and the subjective lenses 752 thereof). The communications interface 746 is also shown to be in communication with a display device 754. The test conductor circuit 714 may be configured to communicate data or other signals to the communications interface 746, where the communications interface 746 then communicates said data and/or signals to the control box 756 (and subsequently the phoropter 748) as well as the display device 754. The communications interface 746 may be configured communicate signals or data received from various components, for example the test conductor circuit 714, to components of the system. Similar to the system 100 as shown and described with reference to FIG. 1, the control box 756 may be configured to adjust and otherwise manipulate the phoropter 748 so as to place and replace the various subjective lenses 752 as well as the various auxiliary lenses 750. In administering an automated subjective refraction test, the control box 756 may be configured to, upon receiving a signal from the communications interface 746, actuate one or more components of the phoropter 748 (e.g., the subjective lenses 752) such that the patient and the test administrator are masked from the actuation (e.g., the patient and test administrator can't tell if power is being added or taken away by the lenses).

The test conductor circuit 714 is shown to be in communication with the communications interface 746, which is shown to be in communication with various components of the system 700. For example, while the input output circuit 712 and the control box 756 are not shown to be in direct communication, the communications interface 746 may facilitate communication between the two components. Further to the previous example, the test conductor circuit 714 (or a component thereof) may communicate data to the communications interface 746 to be subsequently communicated to the control box 756. The communications interface 746 may communicate the data received from the test conductor circuit 714 such that it may be received by the control box 756. Additionally, the communications interface 746 may be configured to facilitate communication between the components of the system 700 through a variety of means, for example wired connections or wireless connections such as Bluetooth or Wi-Fi to a LAN and/or WAN. The communications interface 746 may also be configured to communicate with alternative or additional components not shown in the system 700 as shown in FIG. 7, according to some embodiments.

Each of the testers of the test conductor circuit 714 is configured to conduct the corresponding sub-tests of the automated subjective refraction test. Accordingly, each of the testers, via the test conductor circuit 714, may communicate various data to the communications interface 746, which is in turn communicated to components such as the control box 756 and/or the display device 754. The data communicated by each of the testers of the test conductor circuit 714 to the display device 754 and the control box 756 via the communications interface 746 may be configured to adjust the settings of and/or otherwise actuate the display device 754 and/or the phoropter 748 via the control box 756.

For example, the initial VA tester 724 may receive data via the test conductor circuit 714 and the input output circuit 712 indicating that a test administrator has positioned a patient properly before the phoropter 748 and that the test administrator and the patient are ready to being the automated subjective refraction test. Upon receiving such data, the initial VA tester 724 may be configured to communicate data corresponding to the first step of the initial VA test to the communications interface 746 via the test conductor circuit 714. For example, the data communicated by the initial VA tester 724 may include data communicated to the control box 756, causing the control box 756 to adjust the subjective lenses 752 and/or the auxiliary lenses 750 of the phoropter 748 to affect the vision of the patient in accordance with the first portion of the initial VA sub-tests. Additionally, the data communicated by the initial VA tester 724 may include data communicated to the display device 754 causing the display device 754 to display a specific visual reference (e.g., specific sized graphic, alphanumerical characters, etc.) such that said visual reference may be viewed by the patient through the openings of the phoropter 748. The data communicated by the initial VA tester 724 may also include a GUI configured to be displayed to the test administrator via the input device 710, with the GUI corresponding to the current set of conditions provided by the phoropter 748 and the display device 754. For example, the GUI may include instructions to be read by the test administrator to the patient as well as options to be selected by the test administrator so that the test administrator may provide an input to the input device 710 indicating feedback received from the patient relating to the patient's vision. The instructions presented on the GUI may correspond to the set of conditions presented to the patient as part of the subtest, for example if the display device 754 has been adjusted to display three lines of text of different sizes, the instructions to be read to the patient may include "Please recite the top line of text displayed."

The GUI presented to the test administrator may also include buttons (e.g., icons, etc.) that the test administrator may click, with the buttons corresponding to the instructions also presented on the GUI. Further to the previous example, the test administrator may be presented with a first button labeled "Patient read text correctly" and a second button labeled "Patient did not read text correctly". The GUI may instruct the test administrator to select the button on the GUI displayed by the input device 710 (which may include a touch screen), with the input device 710 configured to communicate the data received from the input provided by the test administrator to the input output circuit 712, with the data ultimately being communicated to the initial VA tester 724 of the test conductor circuit 714. Based on the data, the initial VA tester 724 may determine additional steps to be taken in the administration of the initial VA test. For example, the initial VA tester 724 may communicate data to the communications interface 746 to ultimately be communicated to the control box 756 and the display device 754. The data communicated by the initial VA tester 724 may cause the control box 756 to adjust the phoropter 748 and the display device 754 to adjust the visual reference to as to create a new set of conditions based on the patient's response to the previous set of conditions. The data may also cause the input device 710 to display an updated GUI with updated instructions to be read to the patient by the test administrator, with the instructions corresponding to the new set of conditions produced by the phoropter 748 and/or the display device 754. The updated GUI may also include new buttons corresponding to the new instructions, with the buttons configured to receive an input from the test administrator indicative of the patient's response to the new set of conditions in the sub-test.

Some of the sub-tests mentioned may be administered to a single eye at a time, while some of the sub-tests mentioned are administered to both eyes at once. To accommodate the sub-tests that may be conducted to a single eye of the patient at a time, the test conductor circuit 714 is shown to include an eye selector 722. The eye selector 722 may be configured to receive data from the input output circuit 712 via the test conductor circuit 714 indicating that the patient has been properly positioned in front of the phoropter 748, for example. The eye selector 722 may be configured to select an eye of the patient for which the sub-tests that are administered to a single eye at a time may be administered to first. The eye selector 722 may also be configured to ensure, based on data received from the input output circuit 712 via the test conductor circuit 714, that all such sub-tests have been administered to both the right eye and the left eye of the patient. Once the eye selector 722 receives sufficient data to determine that the necessary sub-tests have been conducted for both the right eye and the left eye of the patient, the eye selector may be configured to determine that all such sub-tests are complete. The eye selector 722 may then generate and communicate a message (e.g., part of a GUI displayed to the test administrator via the input device 710) indicating that all single-eye sub-tests have been completed.

The test conductor circuit 714 is also shown to include a subjective comparison tool 738. The subjective comparison tool 738 can be correspond to a step of the automated subjective refraction test other than a specific sub-test assessing one or more aspects of a patient's vision. For example, during the administration of the automated subjective refraction test, the system 700 may be configured to administer a subjective comparison to the patient conducted by the subjective comparison tool 738. The subjective comparison conducted by the subjective comparison tool 738 may be administered to the patient near the end of the overall automated subjective refraction test. Generally, the subjective comparison tool 738 is configured to present to the patient a comparison between the patient's current prescription (or, if the patient hasn't had a prescription before, plain eyesight) and corrective lenses that the sub-tests of the automated subjective refraction test indicate may improve the vision of the user.

For example, the subjective comparison tool 738 may be configured to function similarly to the initial VA tester 724 (which is the same as or similar to the function of all of the testers of the test conductor circuit 714). The subjective comparison tool 738 may be configured to receive data based on inputs provided to the input device 710 (and/or a GUI displayed by the input device 710) by the test administrator which are communicated to the test conductor circuit 714 (and subsequently subjective comparison tool 738) via the input output circuit 712. Based on the data received, the subjective comparison tool 738 may communicate data via the communications interface 746 to the control box 756 (and the phoropter 748) as well as the display device 754. The data communicated may cause the lenses of the phoropter 748 to be adjusted and the display device 754 to display a specific visual reference. Additionally, the subjective comparison tool may generate an updated GUI to be displayed by the input device 710 to the test administrator. The phoropter 748 may be adjusted by the control box 756 such that the patient is shown the previous lenses that a patient wore (or lack thereof, in some cases) as well as lenses that correspond to a potential new prescription for the patient. The display device 754 may display a single digital reference such that the patient may compare the different lenses (or lack thereof) of the phoropter 748. The input device 710 may display the updated GUI to the test administrator including instructions indicating the comparison being shown to the patient. The GUI may also include buttons allowing the test administrator to provide an input to the input device 710, for example with the buttons labeled "Patient has better vision with proposed lenses" and "Patient does not have better vison with proposed lenses". The feedback provided by the test administrator via the buttons of the GUI may then be communicated to the subjective comparison tool 738 via the test conductor circuit 714 and the input output circuit 712. The subjective comparison tool 738 may then determine, based on the feedback received, if other sub-tests of the automated subjective refraction test need to be conducted again, or if the patient's vision as indicated by the input from the test administrator is consistent with the recommended lenses as determined by the system 700.

The processing circuit 704 is also shown to include a test diagnostic circuit 716, as shown in the exemplary embodiment of FIG. 7. The test diagnostic circuit 716 is shown to be in communication with the input output circuit 712 such that the test diagnostic circuit 716 may receive data from the input output circuit 712, for example an input from the test administrator received the input device 710. The test diagnostic circuit 716 can be configured to manage inputs received by the input device 710, for example determine if the inputs provided by the test administrator to the input device align with a sub-test being conducted. For example, if a test administrator repeatedly provides inputs to the input device 710 indicative of the patient not noticing a difference between two different visual references displayed by the display device 754 and/or combinations of lenses of the phoropter 748, the test diagnostic circuit 716 may provide an indication to the specific tester corresponding to the associated sub-test. Such an indication may include data indicative of the patient not noticing or failing to identify a difference between various sets of conditions. The specific sub-tester corresponding to the sub-test being administered may then repeat steps of the sub-test or modify the sub-test to accommodate the patient's responses as indicated by the feedback provided to the input device 710 and subsequently communicated to the test diagnostic circuit 716.

Additionally, the test diagnostic circuit 716 may indicate if the inputs provided to the input device 710 by the test administrator suggest that the sub-tests may not be performed correctly. For example, if the test administrator were to provide inputs to the input device 710 in successively such that a sub-test may not be administered properly, the test diagnostic circuit 716 may communicate to the corresponding tester administering the sub-test that the sub-test may not be administered correctly. The tester may then be configured to adjust the conditions of the sub-test presented to the patient. For example, the tester may communicate signals to the control box 756 and the display device 754 causing conditions previously presented to the patient to be presented again. The tester may also be configured to generate a GUI for display to the test administrator repeating instructions or asking the test administrator if additional instruction is needed.

The processing circuit 704 is also shown to include an endpoint analyzer circuit 718, as seen in FIG. 7. The endpoint analyzer circuit 718 is shown to be in communication with both the test diagnostic circuit 716 as well as the test conductor circuit 714. The endpoint analyzer circuit 718 is shown to be in communication with the input output circuit 712 and the test diagnostic circuit 716 such that data input to the input device 710 by the test administrator may be communicated to the endpoint analyzer circuit 718. Additionally, the endpoint analyzer circuit 718 may communicate with any one of the testers of the test conductor circuit 714 that are configured to administer the various sub-tests of the automated subjective refraction test. For example, the endpoint analyzer circuit 718 may be configured to communicate with the binocular balance tester 736 regarding data received by the input device 710 relative to a binocular balance sub-test administered to the patient.

The endpoint analyzer circuit 718 is configured to determine one or more endpoints for each of the sub-tests administered by the various testers of the test conductor circuit 714 based on input provided by the test administrator indicative of the patient's vision under different sets of conditions as well as logic paths that can be unique for each of the sub-tests of the subjective automated refraction test. The endpoint analyzer circuit may be configured to determine an endpoint for each sub-test of the automated subjective refraction test from a set of pre-determined endpoints for each sub-test of the automated subjective refraction test based on one or more responses given by the patient in response to conditions presented to the patient by the system 700. The one or more responses (or in the case of two or more responses, the sequence of said responses) given by the patient corresponding to the various conditions of each sub-test determine a pre-determined endpoint of each of the sub-tests as shown and described in the process flow diagrams of FIGS. 10-21 indicating logic applied in the determination of said endpoints. In some embodiments, the determination of a pre-determined endpoint by the endpoint analyzer circuit 718 for a given sub-test may include the application of one or more look-up tables, algorithms, logic charts or the like corresponding to the pre-determined endpoints for each of the sub-tests. For some sub-tests, the corresponding logic path may include multiple endpoints. For example, one endpoint may include a combination of subjective lenses 752 and, in some cases, auxiliary lenses 750 that allow the patient to achieve a visual acuity (VA) of 20/20 for a given sub-test, which as mentioned previously is desirable. Such an endpoint may be referred to as an optimum endpoint (e.g., a best-case endpoint) in which either an ideal VA has been determined (e.g., a VA of 20) or another evaluation of the patient's vision has been completed. However, for some sub-tests and some patients, the endpoint analyzer circuit 718 may determine a pre-determined endpoint indicating that the input provided by the test administrator has reached an endpoint other than a VA of 20/20 for the patient. Such an endpoint may be referred to as a non-optimum endpoint (e.g., a non-best-case endpoint), which can include reaching a point in a given sub-test in which sufficient progress is determined to have been made by the controller 702 and/or the endpoint analyzer circuit 718, and the sub-test is concluded with either a non-ideal VA (e.g., not a VA of 20) or a non-ideal/non-complete evaluation of the patient's vision being completed. Additionally, one or more endpoints of some sub-tests may not correspond to a VA measurement. For example, with reference to the binocular balance test as shown and described in FIG. 18, one endpoint may correspond to the patient having a VA of 20/20 in both eyes, being between ages of 10-55, and having had eye surgery. For example, a sub-test may include combinations of subjective lenses 752 (and possibly auxiliary lenses 750) that does not allow the patient to achieve a VA of 20/20, with the best VA achieved for the patient being a VA of 20/30. While the VA of 20/30 may not be optimum, it may be the best VA that may be produced for the patient by the automated subjective refraction test and the components thereof. Another example can be shown by the red-green sub-test as shown and described in the process of FIG. 12. In said sub-test, an optimum endpoint (e.g., best-case endpoint) may include determining red and green to be equal (e.g., the same), while a non-optimum endpoint (e.g., non-best-case endpoint) may include concluding the test after the patient made the same selection four times within the red-green sub-test. Accordingly, the endpoint analyzer circuit 718 may determine that sufficient data has been collected for the patient for the given sub-test, and accordingly a determination (and a corresponding pre-determined endpoint) may be made that the sub-test cannot progress further (e.g., continuing to administer the sub-test will not yield patient data different from that already collected).

Thus, the endpoint analyzer circuit 718 may determine an endpoint for a sub-test based on receiving a predefined number of responses for a sub-test from a patient, reaching a predefined VA which corresponds to the endpoint for the sub-test, and/or some combination thereof in accordance with the aspects of the present disclosure. The controller 702 may determine the VA of the patient in this exemplary way in order to determine an endpoint corresponding to a preset VA being reached. A VA of 20/20 (or another value) may be determined by the controller based on the combination of subjective lenses used and the patient's ability to read the visual reference presented while the patient is reading the visual reference with those subjective lenses. For example, the VA may be determined to be 20/20 when the patient can read all of the letters or symbols on a specifically sized line that is presented (e.g., on the display device 754) while using the specific combination of subjective lenses. The patient's ability to read the visual reference (e.g., letters, etc.) is determined based on the feedback inputted by, e.g., the technician into the input device (e.g., "yes," "no," "better," "worse", etc. which is received via the buttons on the GUI of the input device). If not, the subjective lenses may be changed via the controller 702 and the patient will be asked to again read the letters or symbols on a specifically sized line in an attempt to get a more accurate lens combination. In this way, determining a VA for a patient may be determined for certain sub-tests that use a predefined VA as an endpoint for the sub-test.

If the endpoint analyzer circuit 718 determines that an endpoint has been reached for a given sub-test, the endpoint analyzer circuit 718 can communicate a signal to the test conductor circuit 714 and/or the corresponding tester of the test conductor circuit 714 indicating that and endpoint has been determined to have been reach for the corresponding sub-test. The test conductor circuit 714 can be in communication with the corresponding tester for the sub-test having reached the end point. The test conductor circuit 714 can also be configured to end the corresponding tester for which the sub-test has reached an endpoint, and subsequently communicate a signal to another tester of the test conductor circuit 714 causing said tester to initiate the next sub-test of the automated subjective refraction test. In initiating the next sub-test, the tester corresponding to the next sub-test may perform various functions such as communicating signals to the communications interface 746. These signals may then be communicated to the phoropter 748 causing the subjective lenses 752 and/or the auxiliary lenses 750 to be adjusted, and may also cause the projector to display a visual reference consistent with the next sub-test. The adjustment of the lenses of the phoropter 748 and/or the display of a new visual reference by the display device 754 can create a new set of conditions for the patient, with the new set of conditions corresponding to the sub-test now being administered. The tester corresponding to the next sub-test now being administered can also generate a GUI that is to be displayed to the test administrator by the input device 710. The GUI may include updated instructions to the test administrator as well as updated instructions to be read by the test administrator to the patient. Additionally, the GUI may include one or more buttons corresponding to one or more inputs that may be provided by the test administrator to the input device indicating the vision of the patient given the set of conditions of the sub-test as provided by the phoropter 748 and the display device 754. This process may be repeated as this sub-test is administered, with the corresponding tester producing updated GUIs and adjusting the phoropter 748 and the display device 754 adjusted to produce new conditions based on feedback provided by the test administrator indicating the patient's vision. Once the endpoint analyzer circuit 718 determines that this sub-test has reached an endpoint, this may be repeated for each sub-test of the automated subjective refraction test until all sub-tests have been administered and completed thus indicating the completion of the automated subjective refraction test.

The memory 708 is shown to include a test result storage database 720, as shown in the exemplary embodiment of FIG. 7. The test result storage database 720 may store data using various methods and means. For example, in some embodiments that test result storage database 720 may include one or more hard drives or other local storage devices. The test result storage database 720 may also implement one or more solid state drives. In some embodiments, the test result storage database 720 can include cloud storage. The test result storage database 720 can also be configured to include various information and data security features in order to protect sensitive data, such as patient test records and other patient-related information. The test result storage database 720 is shown to be in communication with the test conductor circuit 714 such that data may be communicated between the test conductor circuit 714 and any testers thereof and the test result storage database 720. For example, the initial VA tester 724 may communicate data to the test result storage database 720 for storage. The data communicated may include settings of the phoropter 748 and/or the display device 754 to create various sets of conditions for the patient as part of the sub-test. The test result storage database 720 is also shown to be in communication with the input output circuit 712 such that the test result storage database 720 may receive and store data corresponding to inputs provided to the input device 710 by the test administrator. For example, data corresponding to inputs provided by the test administrator can include indications of a patient's vision under various sets of conditions. The test result storage database 720 is also shown to be in communication, either directly or indirectly, with the input output circuit 712, the test diagnostic circuit 716, and the endpoint analyzer circuit 718, and may accordingly receive data for storage. For example, the test result storage database 720 may receive data from the endpoint analyzed indicating what sets of conditions were provided to the patient for a various sub-test, the order in which those sets of conditions were produced, and the details of the endpoint that was reached for the sub-test (e.g., the subjective lenses 752 and/or the auxiliary lenses 750, the visual reference provided by the display device 754, a result of the sub-test corresponding to the endpoint such as a VA, etc.).

The test result storage database 720 is also shown to be in indirect communication with the communications interface 746, as shown in the exemplary embodiment of FIG. 7. For example, as shown in FIG. 7, the test result storage database 720 may be in communication with a medical professional 758 via the communications interface 746. The medical professional 758 may be an O.D., or other medical professional, as discussed previously. The test result storage database 720 may be configured to communicate results of automated subjective refraction tests and/or the various sub-tests administered to a patient by the system 700 to the medical professional 758. For example, upon completion of an automated subjective refraction test by the system 700, the test result storage database 720 may be configured to generate a file including various sets of conditions presented to the patient and the results of each of the sub-tests of the automated subjective refraction test, as well as general patient information (e.g., name, age, previous corrective lens prescription, etc.). The file generated by the test result storage database 720 may then be communicated to the communications interface 746 and disseminated to the medical professional 758. In some embodiments, the medical professional 758 may be in the same location (e.g., the same healthcare facility/building) or may be remote (e.g., at a central healthcare facility with network connections to the facility where the automated subjective refraction test is performed). The data may be communicated by the test result storage database 720 to the medical professional 758 via the communications interface 746 through a variety of means and networks such as Bluetooth and/or Wi-Fi, as well as other possible means. Upon receipt of the data from the test result storage database 720, the medical professional 758 may view, manipulate, and modify the data using one or more devices such as a tablet, personal computer, or other devices. The medical professional 758 may update the data of the test result storage database 720 upon review, manipulation, and modification thereof. Additionally, the test result storage database 720 can also include data supplied by the medical professional 758, for example a diagnosis of a medical condition or a prescription for corrective lenses.

Figure 8:
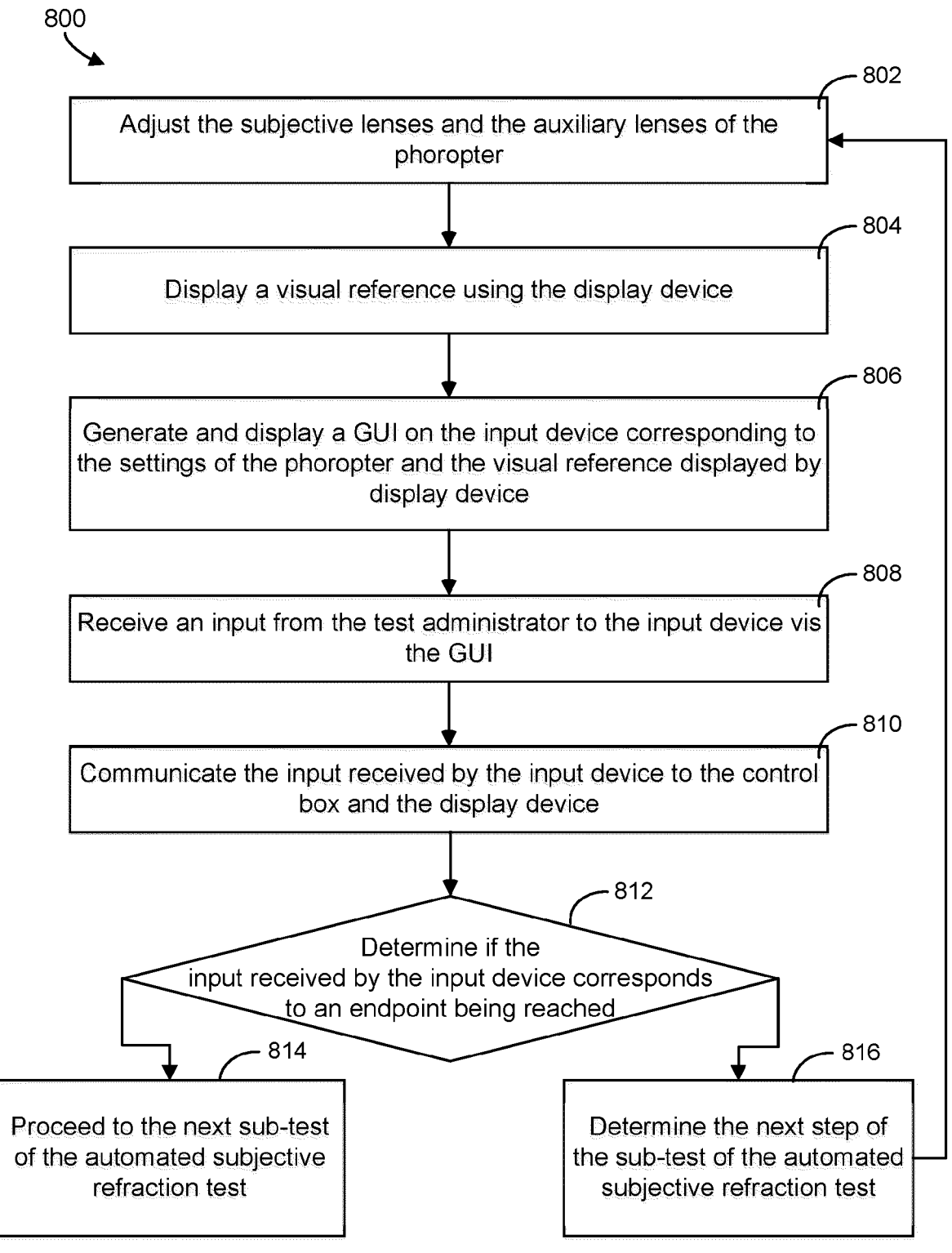
FIG. 8 is a flowchart of a process that can be implemented by the system of FIG. 7 for performing at least a portion of an automated subjective refraction test, according to an exemplary embodiment

Referring now to FIG. 8, a flowchart of a process 800 for administering a portion of a sub-test to a patient. The process 800 may be performed by the components of the system 700, or may be performed by one or more alternative or additional components. The process 800 may be performed for one or more of the sub-tests of an automated subjective refraction test administered to a patient, such as that described with reference to the components of the system 700. For example, the process 800 may be performed as part of an initial sphere refinement test included in an automated subjective refraction test, and may be performed by components of the system 700 such as the initial sphere refinement tester 726, the control box 756, the phoropter 748, the display device 754, and the input device 710. The process 800 may also require a test administrator reading instructions to the patient as provided to the test administrator by the appropriate tester of the test conductor circuit 714 via the input device 710 (e.g., as displayed by the input device 710 on a GUI generated by the appropriate tester). Although not shown, the process 800 may also include a medical professional, with results of the sub-tests and the overall results of the automated subjective refraction test communicated to the medical professional once an endpoint has been determined for each of the various sub-tests and the automated subjective refraction test has been concluded. As the process 800 may be performed by the aforementioned components of the system 700, the steps of the process 800 may include references to such components and/or other similar components.

The process 800 is shown to include adjusting the subjective lenses and the auxiliary lenses of the phoropter (step 802), according to an exemplary embodiment. The phoropter as well as the subjective lenses and/or the auxiliary lenses thereof may be coupled to the control box, where the control box may be configured to receive a signal from one or more components via the communications interface. In step 802, upon receiving a signal indicating that the settings of the phoropter should be adjusted, the control box may manipulate the subjective lenses of the phoropter so as to place subjective lenses in the openings of the phoropter or replace subjective lenses previously positioned in the openings of the phoropter. In some embodiments, the control box may also be coupled to the auxiliary lenses of the phoropter, and may be configured to adjust the auxiliary lenses similar to the subjective lenses.

The process 800 is shown to include displaying a visual reference using the display device (step 804), according to an exemplary embodiment. The display device may be configured to receive a signal from various components of the system via the communications interface and, in response to receiving a signal, may be configured to display or update and already displayed visual reference. In step 804, upon receipt of such a signal, the display device may, for example, display a Snellen chart. Or, in another example in which the display device was already displaying a Snellen chart, update the Snellen chart with new characters and/or characters of different sizes than the previous Snellen chart. The display device may display the visual reference such that a patient may view the visual reference through the openings of the phoropter. Additionally, the display device may be configured to operate in conjunction with the control box as mentioned in step 802. For example, in step 804 the display device may display a visual reference corresponding to subjective lenses and/or auxiliary lenses positioned on and/or in the phoropter so as to complete a step of one of the sub-tests of the automated subjective refraction test.

The process 800 is shown to include generating and displaying a GUI on the input device corresponding to the settings of the phoropter and the visual reference displayed by the display device (step 806), according to an exemplary embodiment. The GUI of step 806 may be generated by the tester of the system corresponding to the sub-test being conducted. For example, with reference to the system 700 of FIG. 7, the initial VA tester 724 may be configured to generate a GUI for the initial VA check of the automated subjective refraction test. Also in step 806, the input device may display the GUI to the test administrator. In some embodiments, the GUI generated in step 806 may be done so in response to one or more inputs provided to the system via GUIs previously presented to the test administrator. Step 806 may also be performed such that the GUI generated in step 806 corresponds to the phoropter settings of step 802 and the visual reference displayed by the display device of step 804. For example, if the visual reference displayed in step 804 is a line of text, the GUI of step 806 may include instructions for the test administrator to ask the patient to read the line of text. Further to the previous example, the GUI of step 806 may also include buttons allowing for the test administrator to input to the GUI if the patient was able to correctly read the text of the visual reference or not.

The process 800 is shown to include receiving an input from the test administrator to the GUI via the input device (step 808), according to an exemplary embodiment. As mentioned previously in step 806, the GUI displayed by the input device operated by the test administrator may include one or more options for the test administrator to provide an input to the system via the GUI. In step 808, the input device receives an input from the test administrator via the GUI generated and displayed in step 806. Further to the previous example of step 806, the input provided to the system via the GUI may include that a patient can or cannot read a line of text given a specific set of subjective lenses positioned in the openings of the phoropter. Or, step 808 may include the test administrator providing an input via the GUI indicating that the patient has clearer vision given a first set of conditions or a second set of conditions.

The process 800 is shown to include communicating the input received by the GUI to the control box and the display device, according to an exemplary embodiment. Step 810 may also include a communications interface configured to be in communication with the control box and the display device. For example, the input device may communicate the input received via the GUI to the control box and the display device via the communications interface. For example, the communications interface may communicate lens settings to the control box and visual reference settings to the display device.

The process 800 is shown to include determining if the input received by the GUI corresponds to an endpoint being reached (step 812), according to an exemplary embodiment. In step 812, the input of the GUI may be analyzed by one or more components, such as the test conductor and the testers thereof, to determine if an endpoint for the sub-test being conducted has been reached. Additionally, the test conductor and/or the communications interface may be in communication with an endpoint analyzer configured to determine based on the input provided via the GUI for the given sub-test if an endpoint has been reached for the sub-test. In step 812, a determination may be made that an endpoint has been reached, in which case data corresponding to the endpoint may be saved, for example by the test result storage database 720 of the system 700.

The process 800 is shown to include proceeding to the next sub-test of the automated subjective refraction test if an endpoint has been determined (step 814), according to an exemplary embodiment. In step 814, one or more inputs that have been received from the test administrator via the GUI may have been analyzed and a determination may have made that an endpoint has been reached for the given sub-test. The determination of such an endpoint may correspond to sufficient data being collected from the patient. For example, in some embodiments an endpoint may correspond to a combination of subjective and/or auxiliary lenses that allow the patient to achieve a corrected 20/20 vision. However, in some other embodiments and endpoint may correspond to a determination that as much data as possible has been collected from the patient. For example, it may be determined that a patient may not be able to achieve corrected 20/20 vision through a combination of the subjective lenses and/or the auxiliary lenses, and the determination may further include a maximum corrected vision for the patient of 20/30. Upon the determination of an endpoint having been reached in step 814, a subsequent sub-test of the automated subjective refraction test may begin. Or, if the sub-test for which the endpoint has been determined is the final sub-test of the automated subjective refraction test, then the automated subjective refraction test may be concluded.

The process 800 is shown to include determining the next step of the sub-test of the automated subjective refraction test if an endpoint has not been determined (step 816), according to an exemplary embodiment. In step 816, a determination is made that an endpoint for the given sub-test of the automated subjective refraction test has not been reached. For example, this may include a patient being presented a line of text via the projector and being unable to read the line of text. As the patient's vision may not have been adequately assessed for the sub-test, the system may then determine that subjective lenses and/or auxiliary lenses of the phoropter should be adjusted and the line of text be presented to the patient again. If the process 800 reached step 816 rather than step 814, the process 800 may be restarted as shown in FIG. 8. Step 816 may be repeated several times for a given sub-test of the automated subjective refraction test the process 800 reaches step 814 and an endpoint is determined to have been reached, at which case another sub-test of the automated subjective refraction test may begin.

Figure 9:
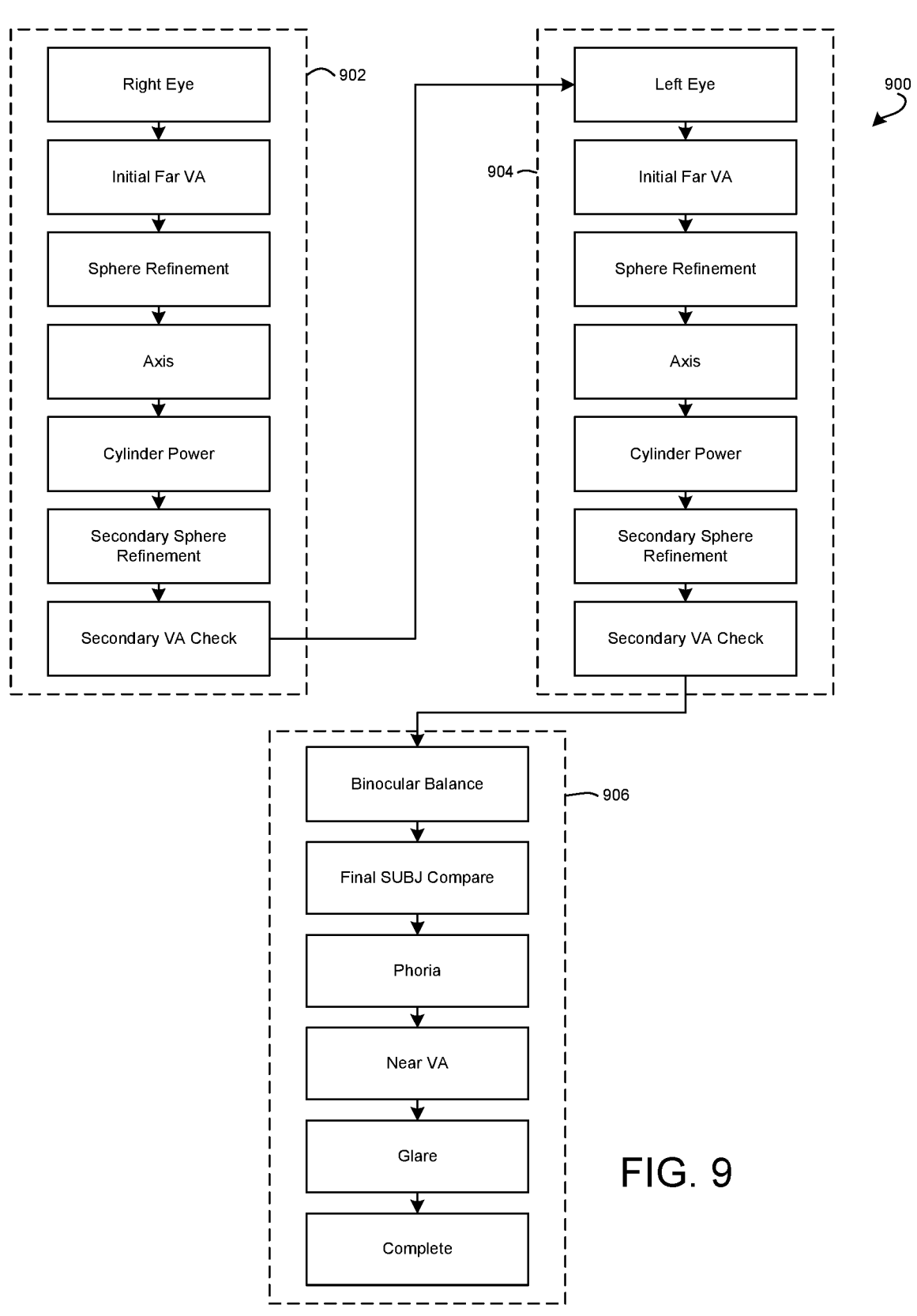
FIG. 9 is a flowchart of a process that can be implemented by the system of FIG. 7 for performing at least a portion of an automated subjective refraction test, according to an exemplary embodiment.
Figure 10A:
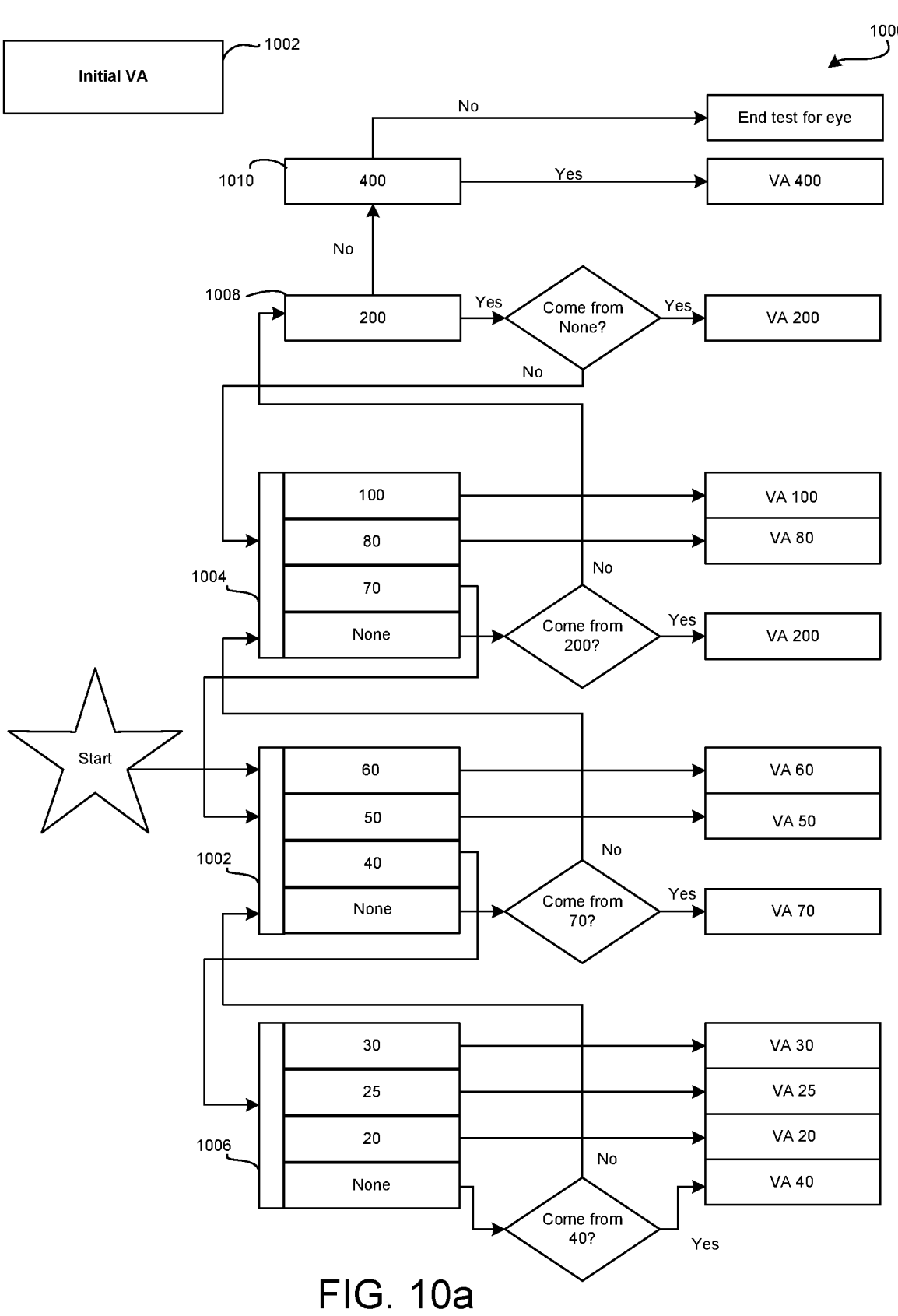
FIG. 10a is a flowchart of a process that can be implemented by the system of FIG. 7 for performing an initial visual acuity check, according to an exemplary embodiment.

Referring now to FIG. 9, a flowchart of a process 900 that can be implemented for administering an automated subjective refraction test is shown. The process 900 may also involve a test administrator, who may be an individual without expertise in optometry ophthalmology. The process 900 may be implemented by a system such as the system 700, with the various sub-tests as shown in the process 900 corresponding to the testers of the test conductor circuit 714 of the system 700. For example, the initial VA test as shown in FIG. 10a may be administered by the initial VA tester 724 in conjunction with the other components of the system 700 as shown and described in FIG. 7. In some embodiments, the process 900 and the corresponding automated refraction test may not be appropriate for some patients based on the vision of said patients. For example, if a patient has a binocular VA of worse than 400, the process 900 may not be applicable in some or all forms.

The process 900 may also include steps other than the various sub-tests (e.g., a right eye testing process 902, a left eye testing process 904, and a binocular balance process 906) of an automated subjective refraction test. For example, some of the sub-tests of the process 900 may be conducted for a single eye at a time. Accordingly, such steps may be conducted by the eye selector 722 of the test conductor circuit 714 as shown in the system 700. Additionally, the process 900 may also include additional steps not shown in FIG. 900. For example, prior to beginning the process 900 the test administrator may collect basic information from a patient (e.g., name, date of birth, current prescription for corrective lenses, etc.). Additionally, the test administrator may aid the patient in assuming the proper position for the automated subjective refraction test. For example, the test administrator may adjust a seat for the patient, or may adjust the phoropter (102 or 748) as shown and described previously such that the patient may view visual references properly.

The process 900 may also include repeating various steps according to some embodiments. For example, the system 700 and components thereof may determine that data is not being collected correctly for a given sub-test of the automated subjective refraction test. Accordingly, said sub-test may be repeated, or skipped and then repeated later in the process 900. The sub-tests and other steps of the process 900 may also be skipped depending on various factors including, for example, the patient. For example, if the patient were to be blind in one eye or otherwise have lost sight in one eye (e.g., lost an eye, injury to an eye, etc.), the process 900 may be modified by the system 700 so as to skip the single-eye tests for the eye of the patient that has lost sight. In some embodiments, the process 900 may also include additional steps and/or sub-tests. For example, if a patient were to have a diagnosed optical condition that requires additional or modified testing, the system 700 may adjust or otherwise modify the process 900 so as to accommodate the conditions and/or concerns of any patients.

Referring now to FIGS. 10-20, flowcharts of processes for implementing sub-tests of automated subjective refraction tests are shown. The sub-tests corresponding to the processes shown in FIGS. 10-20 may be administered by the system 700 of FIG. 7, and more specifically may be administered by the corresponding testers of the test conductor circuit 714. The processes for sub-tests may include one or more endpoints that, when reached, indicate the completion of the respective sub-test. The determination of the endpoint or endpoints of the sub-tests shown in the processes of FIGS. 10-20 may be determined by the endpoint analyzer circuit 718 as shown in the system 700. The determination of the endpoint or endpoints for a sub-test can indicate that the next sub-test or step in the process 900 of FIG. 9 may to be performed. Upon the determination of an endpoint or endpoints for the final sub-test of the process 900, the automated subjective refraction test may be concluded.

Referring now to FIG. 10a, a flowchart of a process 1000 that can be implemented for administering an initial VA check (or test) is shown. The process 1000 may correspond to the "initial far VA" as shown in the process 900 of FIG. 9, and may be performed for each eye of the patient independently. The steps of the process 1000 may be performed by the initial VA tester 724, which can be configured to operate in conjunction with one or more additional components of the system 700. Each eye tested using the process 1000 may be determined by the eye selector 722 as shown in the system 700 of FIG. 7. The initial VA check as shown in the process 1000 may involve the test administrator asking the patient to read one or more lines of text or other characters (e.g., VA chart 1002) displayed by the display device 754 as part of a visual reference. Depending on whether the patient is able to read the text of the first visual reference presented, subsequent visual references (e.g., VA chart 1004, VA chart 1006, VA Chart 1008 and VA chart 1010) may be presented to the patient. For example, if the patient correctly identifies the text of the first visual reference, the subsequent visual references may include progressively smaller text (e.g., from 100 to 80 in VA chart 1004) until a visual reference is displayed with text too small for the patient to identify. Conversely, if the patient incorrectly identifies the text of the first visual reference, the subsequent visual references may include progressively larger text until a visual reference is displayed with text large enough for the patient to correctly identify the text. The test administrator may ask the patient to read each line of text presented and provide to the input device 710 an input indicative of whether the patient correctly read the line of text or was unable to. The input device 710 may then communicate data to other components of the system 700, including the display device 754 which may then cause the projector to display the updated visual reference. The initial VA tester 724 may be configured to generate an updated GUI to be displayed by the input device 710. The updated GUI may correspond to the visual reference presented by the display device 754. This process may be repeated, as shown in the process 1000, until an endpoint is reached. The endpoints, as shown in the process 1000, correspond to a determined initial VA for the patient.

In some embodiments, such as the previous example, the process 1000 may not incorporate the subjective lenses 752 or the auxiliary lenses 750 of the phoropter 748. Additionally, the process 1000 may be repeated or have steps of the process 1000 repeated depending on the patient's ability to read the text of the visual references. For example, it may be common for a patient to be unable to read text of a certain size in his/her first attempt, but s/he may be able to read the same text in a second attempt. The results (and the various steps) of the process 1000 (the VA) may be saved by the system 700 in the test result storage database 720 upon the completion of the process 1000. Once an endpoint of the process 1000 has been reached, which may be determined by the endpoint analyzer circuit 718, the process 1000 is completed and the next step in the process 900 may begin.

Figure 10B:
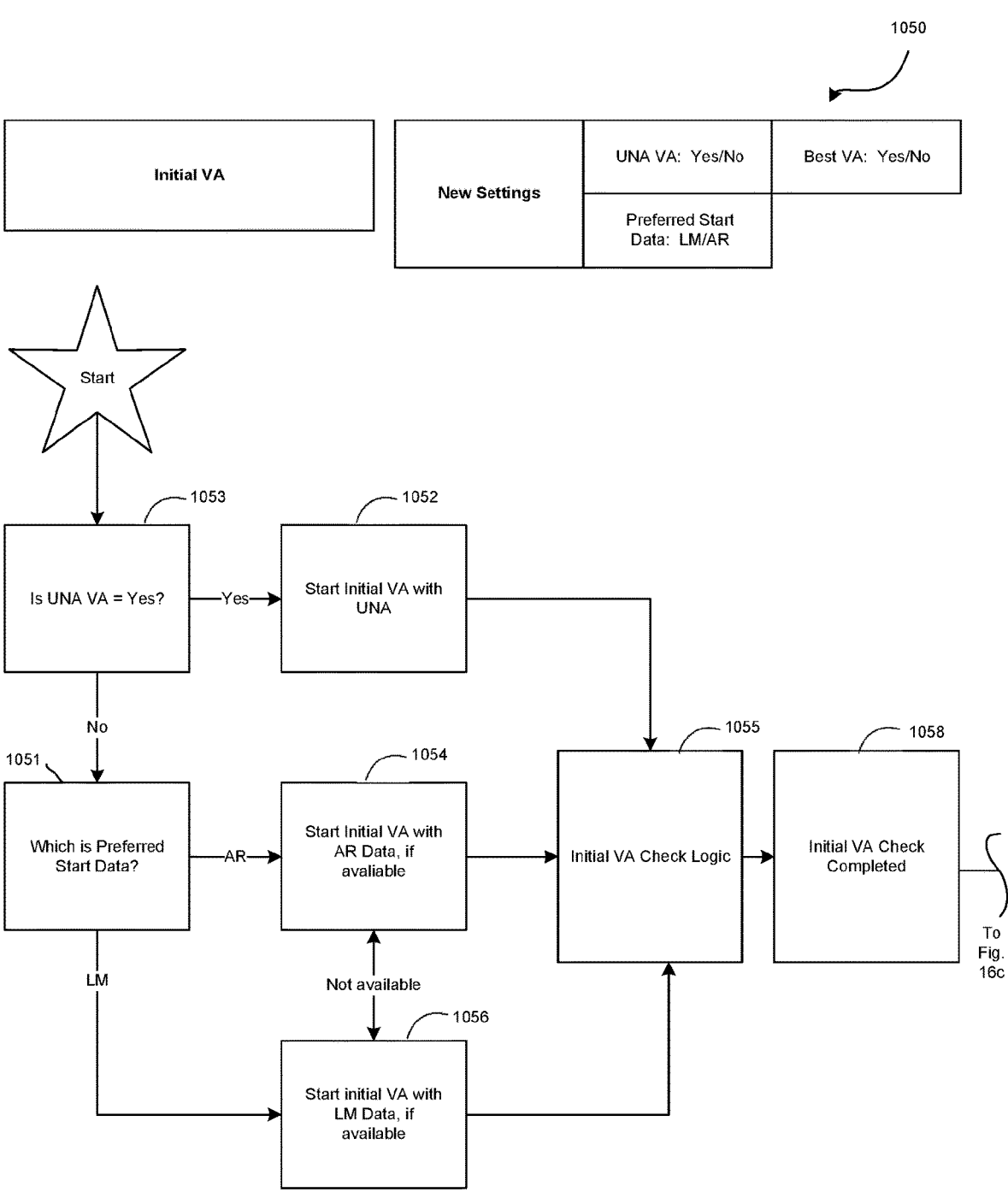
FIG. 10b is a first portion of a flowchart of another process that can be implemented by the system of FIG. 7 for performing an initial visual acuity check, according to an exemplary embodiment.

Referring now to FIG. 10*b* a first portion of a flowchart of a process 1050 that can be implemented for administering an initial VA check (or test) is shown, according to an example embodiment. The process 1050 may correspond with the "initial far VA" as shown in the process 900 of FIG. 9, and may be performed for each eye of the patient independently. The steps of the process 1050 may be performed by the initial VA tester 724, which can be configured to operate in conjunction with one or more additional components of the system 700. Each eye tested using the process 1050 may be determined by the eye selector 722 as shown in the system 700 of FIG. 7. The steps of process 1050 may be used to determine the best VA data for each eye individually as a starting point for further subjective refraction testing (e.g., the automated subjective refraction test of the process 900). Conventionally, the starting point for subjective refraction testing is determined for both eyes using data taken from either an auto-refactor (AR) measurement or the lensmeter (LM) measurement, even if the AR is more accurate for one eye and the LM is more accurate for the other eye. However, by determining the best starting point for further subjective refraction testing independently for each eye (e.g., an auto-refractor (AR) measurement may give the best initial objective VA measurement for a patient's right eye and a lensmeter (LM) measurement may give the best initial VA measurement for the patient's left eye), a more accurate starting point may be determined for each eye on an individual basis, thereby reducing the amount of subsequent subjective refraction testing needed for each eye.

The initial VA check as shown in the process 1050 may involve starting the initial VA test (process 1052) by testing the patient's unaided (UNA) VA (i.e., plano or zero) (e.g., decision 1053), which is an initial VA check with no corrective lenses. For example, process 1052 may be the same or similar to process 1000. Alternatively, the initial VA test may be started using objective refraction data taken from an auto-refractor (AR) (process 1054) or using objective refraction data taken from a lensmeter (LM) (process 1056). For example, the initial VA tester 724 may be configured to generate a GUI to be displayed by the input device 710 that asks the operator what the preferred start data/point is (as a part of decision 1051). In some embodiments, an AR measurement may be taken and a LM reading may be taken as part of the patient's routine eye examination. In this example embodiment, process 1054 and 1056 may utilize the data from these two measurement if they are available. The various initial VA data may then be checked for accuracy (process 1055) which may complete the initial VA check (process 1058).

Figure 10C:
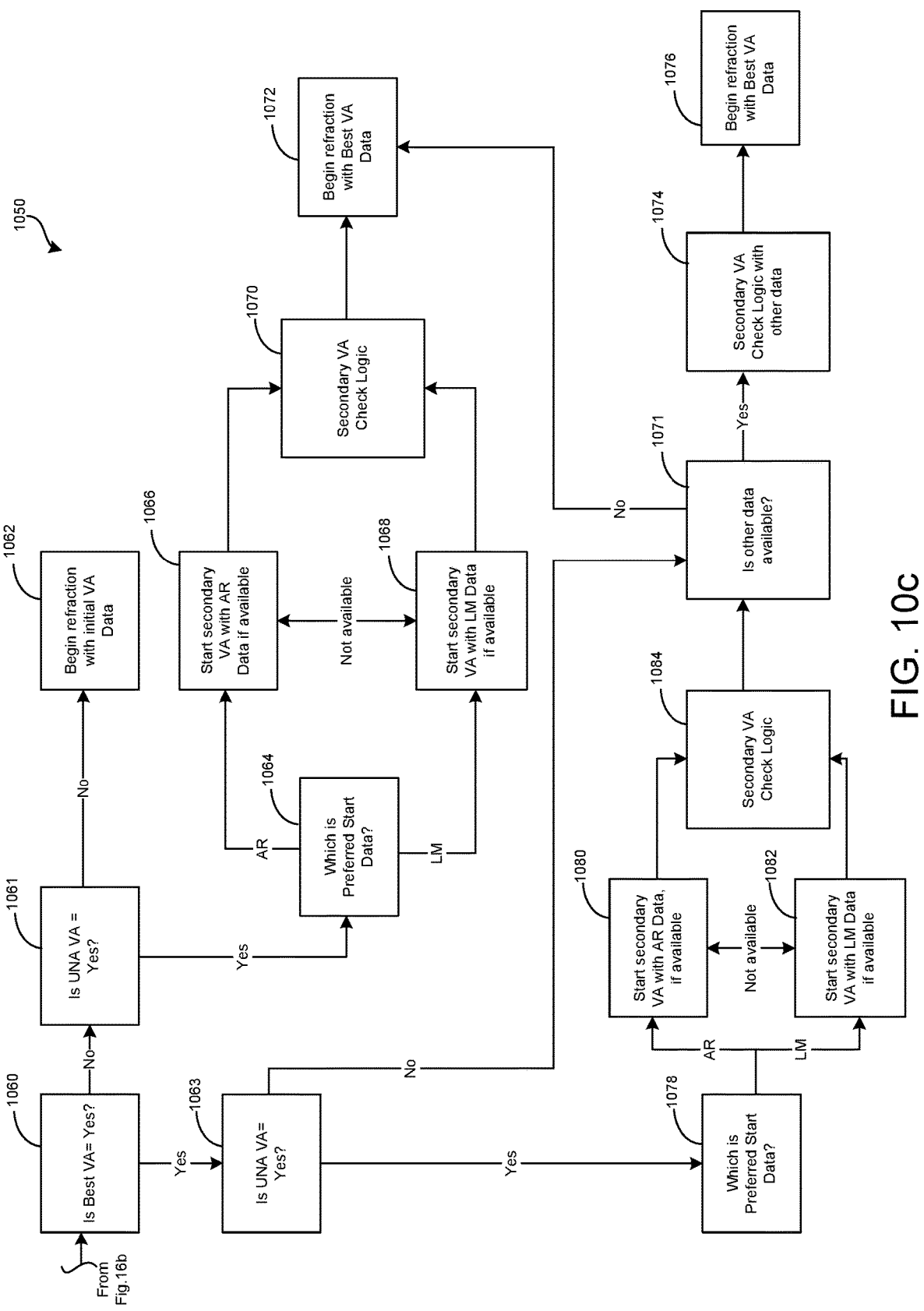
FIG. 10c is a second portion of the flowchart of the remainder of the process of FIG. 10b that can be implemented by the system of FIG. 7 for performing an initial visual acuity check, according to an exemplary embodiment.

Referring now to FIG. 10*c*, once the initial VA check is completed (process 1058), the initial VA tester 724 may be configured to generate an updated GUI to be displayed by the input device 710. The updated GUI may ask if the operator would like to determine the best VA starting point for each eye (as a part of decision 1060). If the operator indicates that he or she does not want to independently determine the best VA starting point for further subjective refraction testing (at decision 1060), and no UNA VA has been taken (decision 1061), the subjective refraction testing may be started (e.g., process 1062) using the initial VA data (e.g., the initial VA data from process 1058). If UNA VA has been measured (decision 1061), the initial VA tester 724 may be configured to generate a GUI to be displayed by the input device 710 that asks the operator what the preferred start data is (as a part of decision 1064). The operator may then indicate the preferred start data to start a secondary VA check (e.g., starting with AR measurement data at process 1066 or starting with LM measurement data at process 1068). This data may then be compared to other available data (e.g., if the AR data is used for the secondary VA test, this may be compared to the UNA VA data and/or the LM VA data as a part of process 1070) and the best available VA data may be used for the subsequent subjective refractions testing (process 1072).

If the operator indicates that he or she would like to independently determine the best VA starting point for further subjective refraction testing (e.g., at decision 1060), and UNA VA data has not been taken (e.g., as decided at decision 1063), the processing circuit 704 will determine whether other VA data is available (e.g., decision 1071). If no other data is available, the subjective refraction may begin (e.g., process 1072) using the best VA data available (e.g., from process 1058). If other data is available, a secondary VA check may be performed (e.g., process 1074) that compares the available VA data for each eye independently. The refraction testing may then begin (e.g., process 1076) using the best VA data available for each eye. Referring back to decision 1063, if UNA VA has been taken, the initial VA tester 724 may be configured to generate a GUI to be displayed by the input device 710 that asks the operator what the preferred start data is (e.g., as a part of decision 1078). The operator may then indicate the preferred start data to start a secondary VA check (e.g., starting with AR measurement at process 1080 or starting with LM measurement at process 1082). A secondary VA check may then be performed using the available data (e.g., if the AR data is used for the secondary VA test, this may be compared to the LM VA data as a part of process 1084). After the secondary VA check (e.g., process 1084, the processing circuit 704 will determine if other data is available (decision 1071). If not, subsequent subjective refractions testing may begin (process 1072). If there is other data available, a secondary VA check may be performed to determine the best VA data available independently for each eye (e.g., process 1074). The refraction testing may then begin (process 1076) using the best VA data available for each eye.

Figure 11:
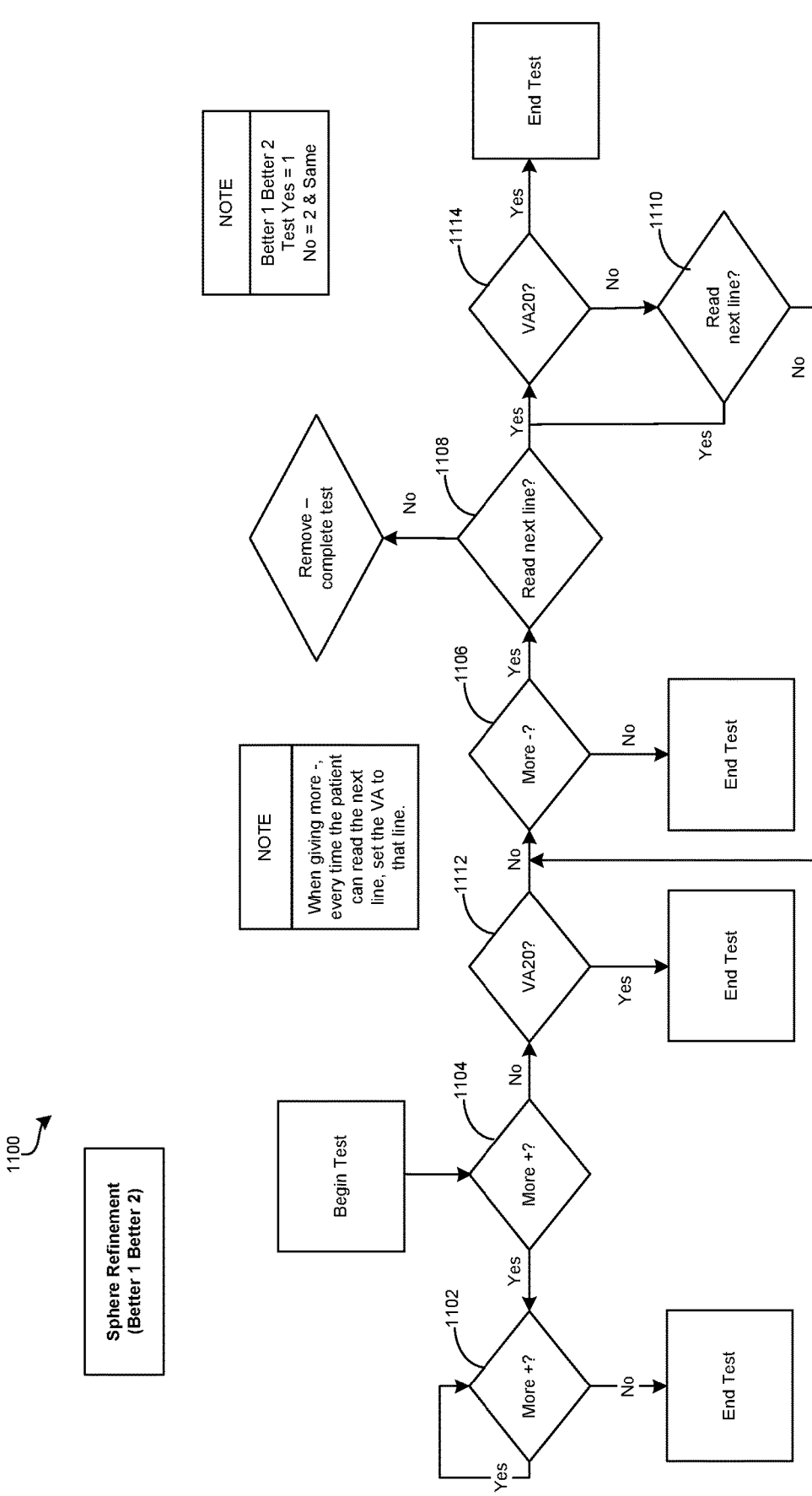
FIG. 11 is a flowchart of a process that can be implemented by the system of FIG. 7 for performing an initial sphere refinement test, according to an exemplary embodiment.

Referring now to FIG. 11, a flowchart of a process 1100 that can be implemented for administering an initial sphere refinement test is shown. Generally, the process 1100 determines what "plus" or "minus" a patient may prefer for corrective lenses (e.g., decision 1102, decision 1104, and decision 1106) and can correspond to determining a lens that may fit the eye of the patient. However, the process 1100 can include limitations. For example, the process 1100 may be configured to prevent the patient from taking "minus" if a VA has been determined to be at and may be further configured to require the patient read additional text of a visual reference (e.g., process 1108 and process 1110) in order to establish a need for "minus" if a VA has been determined to be above 20/20 (e.g., decision 1112 and decision 1114). In certain embodiments, the VA may be determined to be 20/20 during a subjective refraction test when the patient can read some or all of the letters or symbols on a specifically sized line (e.g., 20/20) that is presented (e.g., on the display device 754) while using a specific combination of subjective lenses. If the patient has done so, the subjective lenses may be changed and the patient will be asked to again read the letters or symbols on a specifically sized line in an attempt to get a more accurate lens combination. It should be appreciated that the letters or symbols displayed may be changed such that the patient cannot memorize the letters or symbols displayed. The process 1100 may correspond to the "sphere refinement" as shown in the process 900, and as shown in the process 900 may be administered to each eye of the patient separately. The eye selector 722 of the system 700 may select an eye of the patient for which the process 1100 is performed, with the process 1100 subsequently repeated for the second eye of the patient. The process 1100 may be performed by the initial sphere refinement tester 726 in conjunction with other components of the system 700. The process 1100 may include the test administrator receiving a GUI on the input device 710 having buttons allowing the test administrator to display an "option 1" and an "option 2" to the patient. The "option 1" may correspond to a first set of conditions which can include a combination of a first pair of subjective lenses 752, a first visual reference displayed by the display device 754, and/or a first pair of auxiliary lenses 750. The test administrator may operate the GUI to present "option 1" to the patient by pressing the corresponding button, and then present "option 2" to the patient by pressing the second corresponding button. Similar to "option 1", "option 2" may include one or more of a second pair of subjective lenses 752, a second visual reference displayed by the display device 754, and/or a second pair of auxiliary lenses 750. Thus, when presenting options 1 and 2, the visual presented to the patient does not change, it is only the lenses that change. For example, when presented "option 1" the patient may observe a chart 1 through lens A, and then a chart 2 through lens A. The patient may then be presented "option 2" in which the patient is presented lens B such that the patient may view chart 2 through the lens B and compare the effect of lens A to lens B on chart 2. In some embodiments, if the visual reference is changing while the patient is asked to observe it, the subjective and/or auxiliary lenses are not be changed. Similarly, if the subjective and/or auxiliary lenses are changing while the patient is observing a visual reference through them, the visual reference is not changed. The visual reference and the subjective and/or auxiliary lenses may only be changed at the same time when a system such as the system 700 is transitioning from one sub-test to the next. But even in this situation, this changing is caused from moving on to a new sub-test; the lenses and visual reference are not linked to each other. The patient may then provide an indication to the test administrator that the patient prefers, or has clearer vision when presented with "option 1", "option 2" or indicates that "option 1" and "option 2" are about the same. Accordingly, the test administrator can provide an input to the input device 710 corresponding to the feedback provided by the patient.

The input device 710 may then communicate a signal corresponding to the input received from the test administrator to other components of the system 700. For example, the input device 710 may communicate the signal to the control box 756 and the display device 754. This signal may cause the control box 756 to adjust the subjective lenses 752 and/or the auxiliary lenses 750 of the phoropter 748, and may also cause the display device 754 to display an updated visual reference. Additionally, the initial sphere refinement tester 726 may generate an updated GUI to be displayed by the input device 710 corresponding to an updated "option 1" and "option 2" to be presented to the patient. As shown in FIG. 11, the steps of process 1100 may be repeated until an endpoint is reached, where the endpoint may be determined by the endpoint analyzer circuit 718 of the system 700. Once an endpoint has been reached for the process 1100, the corresponding data from performing the process 1100 may be stored by the test result storage database 720 and the next step of the process 900 may begin.

Figure 12:
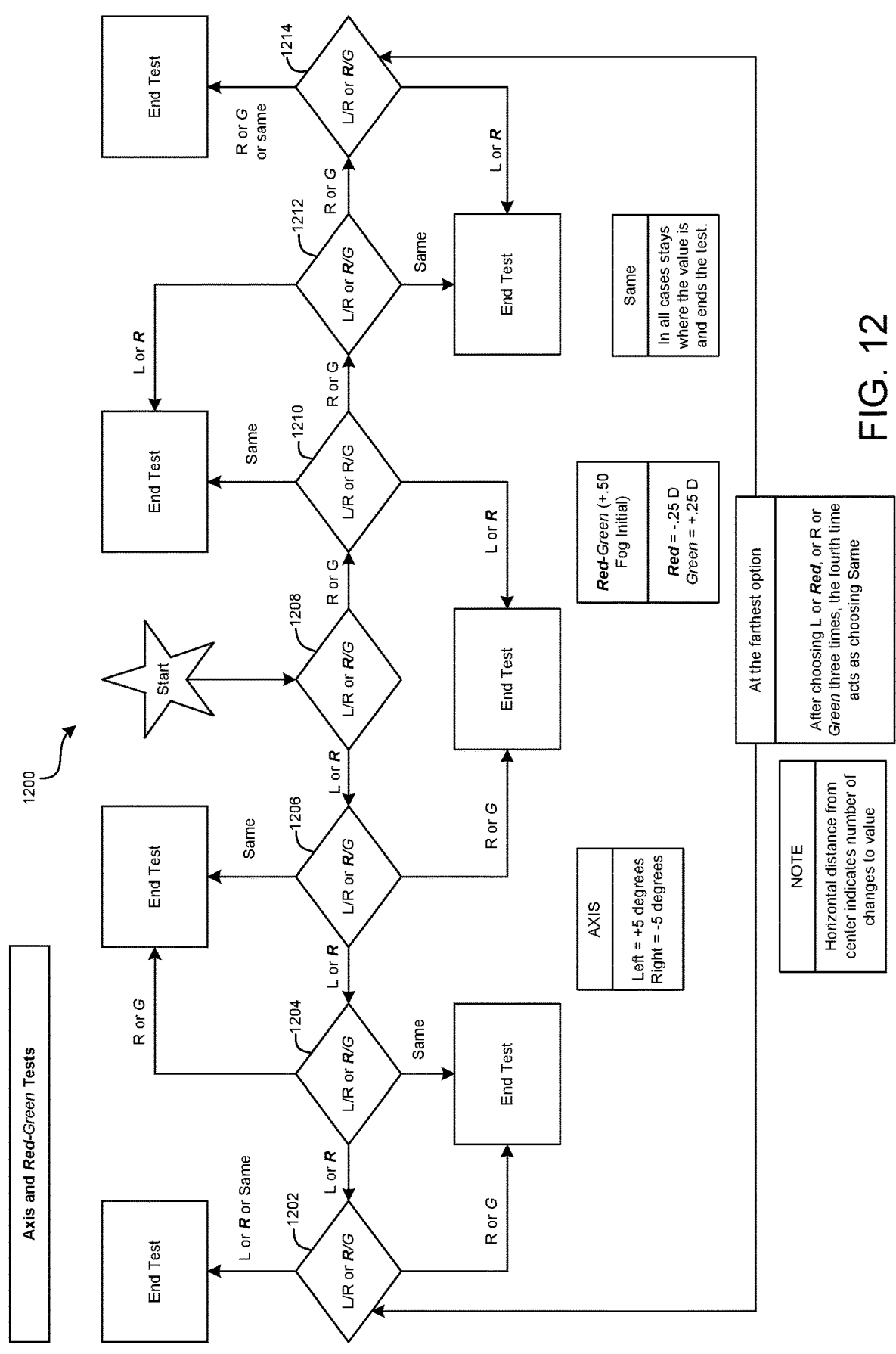
FIG. 12 is a flowchart of a process that can be implemented by the system of FIG. 7 for performing a first axis test, according to an exemplary embodiment.
Figure 13:
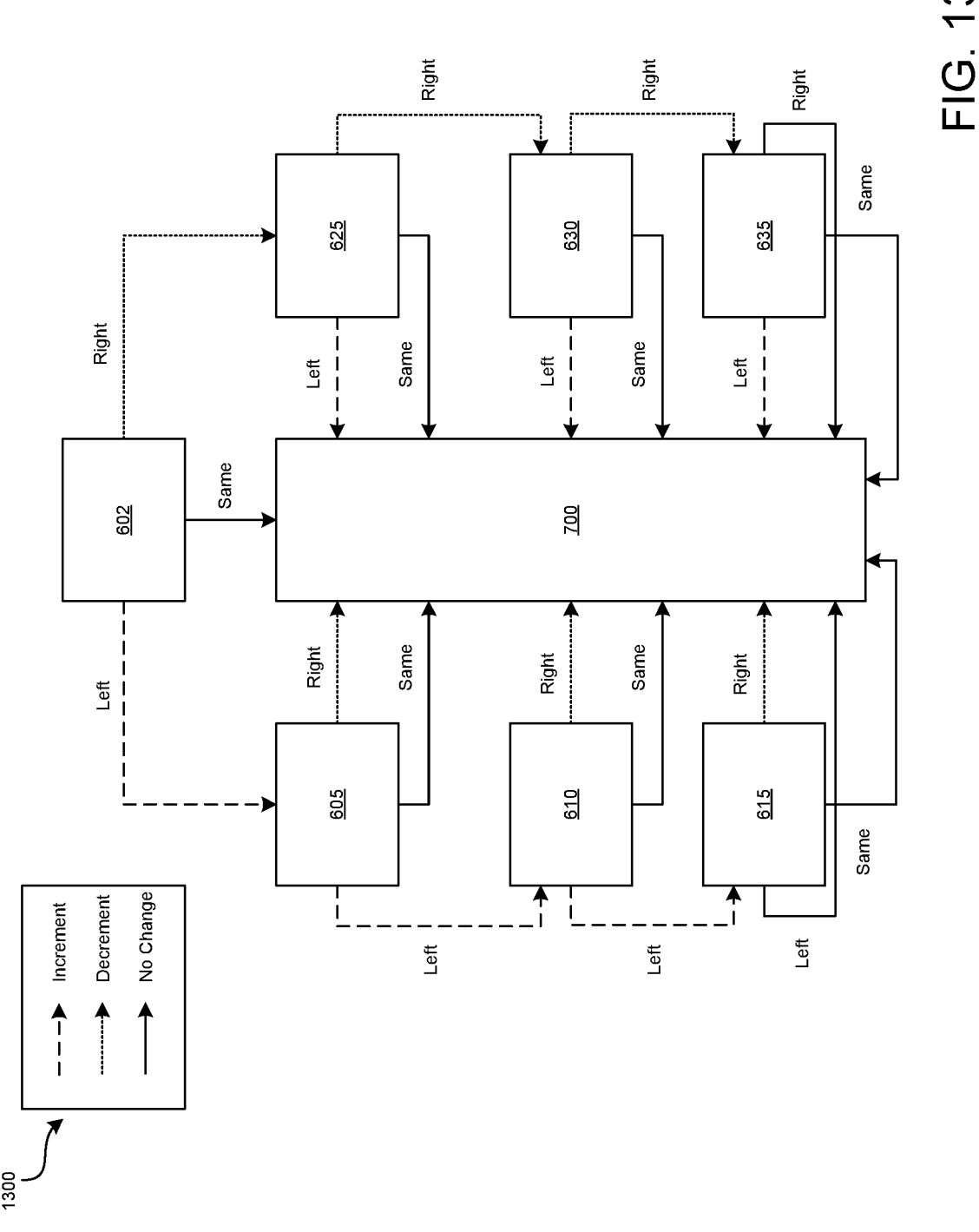
FIG. 13 is a flowchart of a process that can be implemented by the system of FIG. 7 for performing a second axis test, according to an exemplary embodiment.

Referring now to FIG. 12 and FIG. 13, flowcharts of process 1200 and 1300 that can be implemented for administering axis tests are shown. In some embodiments, the process 1200 for performing a first axis test and the process 1300 for performing second axis test may be conducted successively. The processes 1200 and 1300 may be carried out by the corresponding components of the test conductor circuit 714, the axis tester 728 and/or the red-green tester 729, and may also be conducted for a single eye of the patient at a time. As shown in FIG. 12, the process 1200 includes axis tests and red-green tests (e.g., decision 1202, decision 1204, decision 1206, decision 1208, decision 1210, decision 1212, and decision 1214) which may be conducted successively by the system 700 and more specifically, the axis tester 728 and the red-green tester 729 in conjunction with other components. The red-green test is configured to check sphere (e.g., measure and/or refine spherical endpoint) and, as shown in the process 1200, may include the display device 754 displaying one or more visual references having multiple colors, such as the visual reference 602 as shown in FIG. 6, for example. The first axis test of the process 1200 may be configured to be confined to a 15-degree range from a set starting point. In conducting the axis tests, the axis may be increased or decreased, with the general purpose of the axis tests of process 1200 and the process 1300 to determine the axis of the stigmatism of the patient, which can correspond to a misshape of the cornea of the patient. The axis tests can include further limitations such as, for example ending the test if the axis is increased after having been decreased, or if the axis is decreased after being increased. Similar to other previous processes, the processes 1200 and/or 1300 may be ended upon the determination of an endpoint by the endpoint analyzer circuit 718, which may cause the next sub-test in the process 900 to begin.

Figure 14:
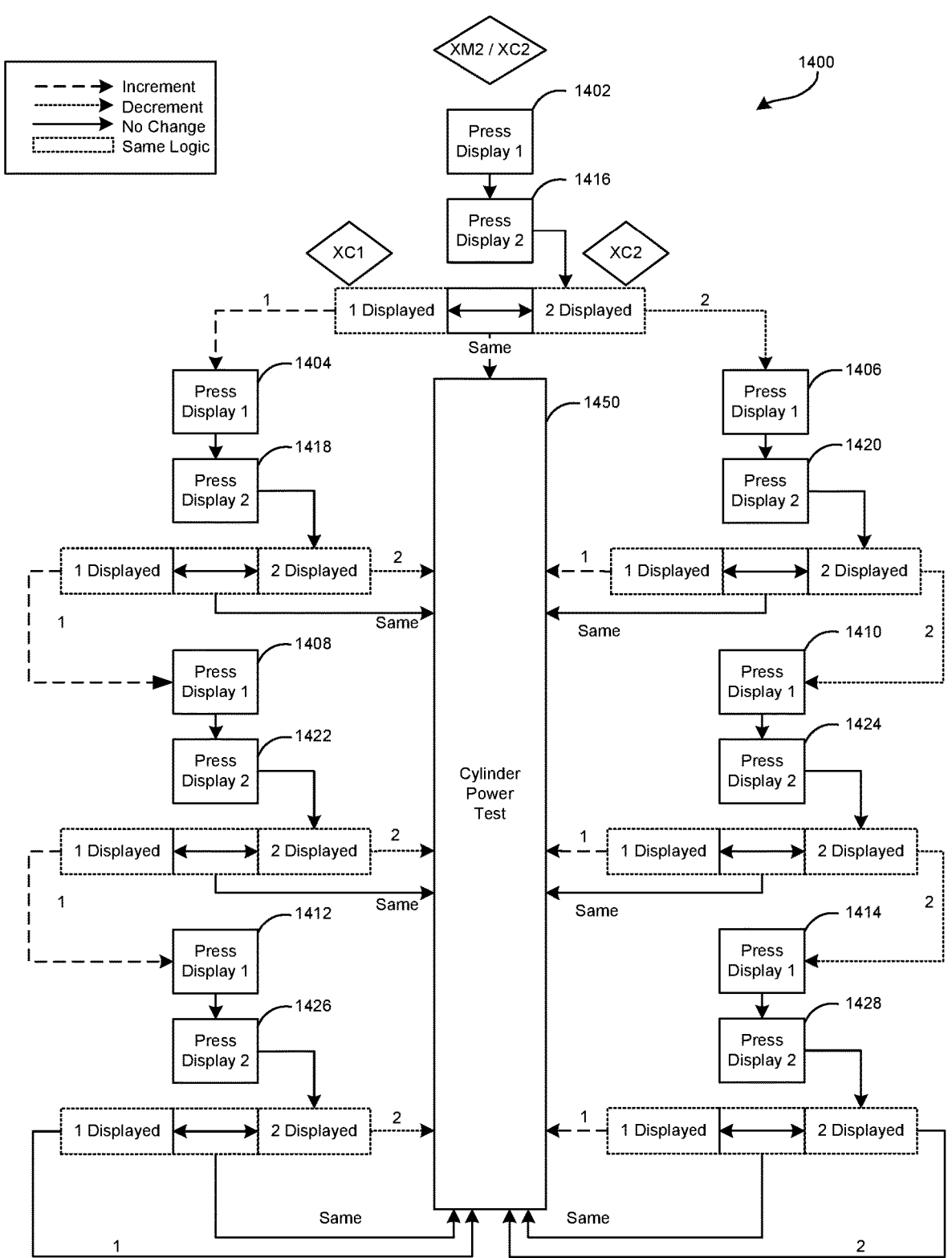
FIG. 14 is a flowchart of a process that can be implemented by the system of FIG. 7 for performing a first cylinder power test, according to an exemplary embodiment.

Referring now to FIG. 1400, a flowchart of a process 1400 that can be implemented for administering a cylinder power test is shown. The cylinder power test may be administered to the patient according to the process 1400 as shown in FIG. 14. Generally, the purpose of the cylinder power test is finding the magnitude to the astigmatism of the patient, which can correspond to the correction that the patient requires. However, the correction may only be determined after the magnitude of the astigmatism has been determined, so the astigmatism may be measured first. The process 1400 may also be conducted for a single eye of the patient at a time. In the cylinder power test 1450 of the process 1400, the system 700 and the components thereof may be configured to give up to 0.50D more cylinder, or take away up to 0.75D, or reach 0. The cylinder power tester 730 may be configured to determine whether the patient is given 0.50D, has 0.75D taken away, or reaches 0 first and records corresponding data in the test result storage database 720. In some embodiments, the process 1400 may be modified, for example to implement the Jackson Cross cylinder test. Accordingly, the patient may be displayed an "option 1" (e.g., process 1402, process 1404, process 1406, process 1408, process 1410, process 1412, and process 1414) and an "option 2" (e.g., process 1416, process 1418, process 1420, process 1422, process 1424, process 1426, and process 1428) as described previously with reference to the initial sphere refinement test of process 1100 as shown in FIG. 11. Based on the feedback provided to the test administrator by the patient indicating whether "option 1" or "option 2" appears more clear, or if they appear about the same, the test administrator may provide an input to the input device 710 that is communicated to other components of the system 700. Other variations of the process 1400 may also be implemented depending on the patient and other variables.

Figure 15:
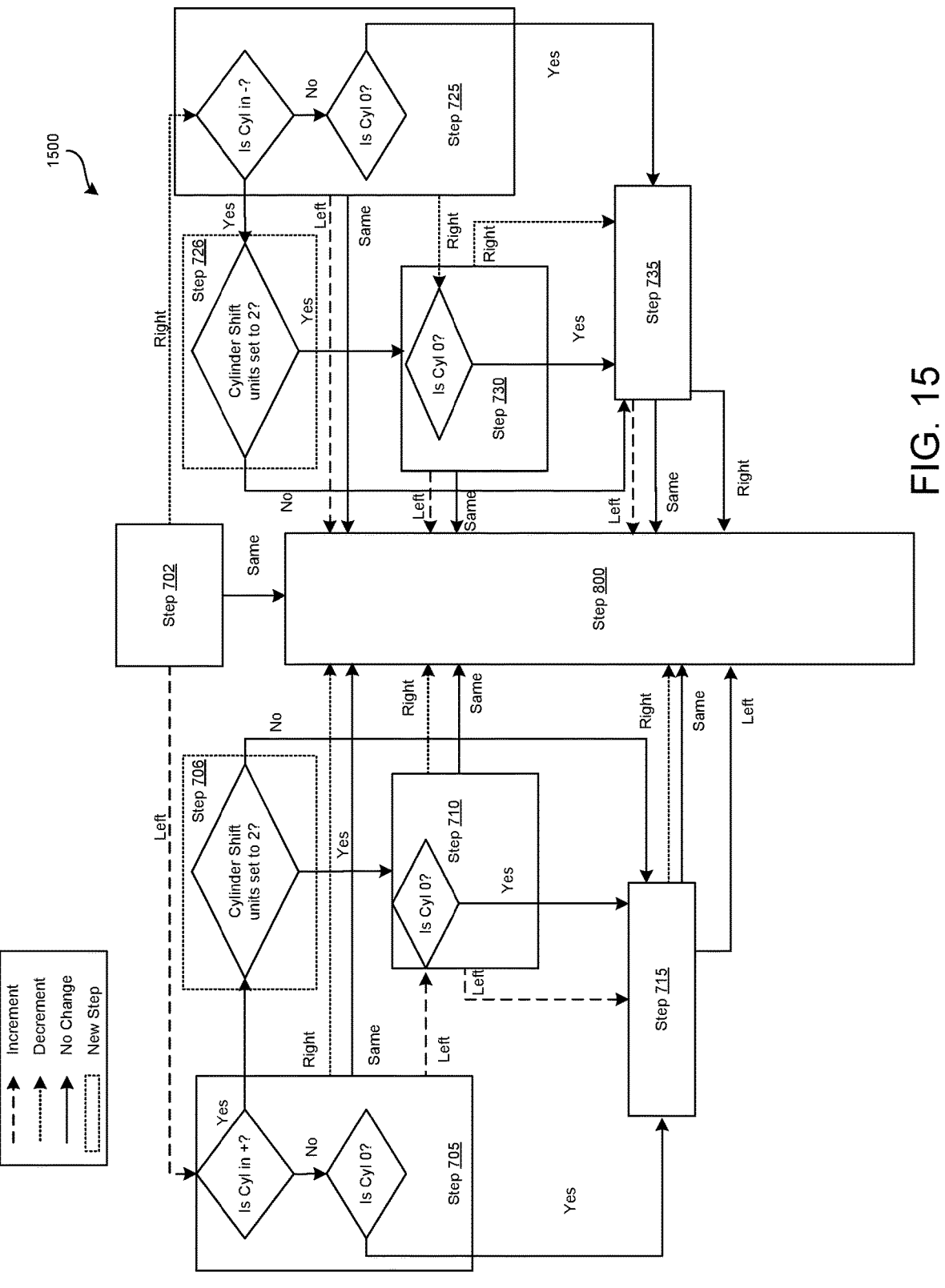
FIG. 15 is a flowchart of a process that can be implemented by the system of FIG. 7 for performing a second cylinder power test, according to an exemplary embodiment.

Referring now to FIG. 15, a flowchart of a process 1500 that can be implemented for administering an additional cylinder power test is shown. Similar to the process 1400 of FIG. 14, the process 1500 may be conducted by the cylinder power tester 730 in conjunction with other components of the system 700 and may also be conducted for a single eye at a time. The process 1500 may, in some embodiments, be performed by the system 700 and the components thereof simultaneously to the process 1400 or may be performed successively with the process 1400. Additionally, both the processes 1400 and 1500 may conclude when and endpoint has been determined by the endpoint analyzer circuit 718 of the system 700. The determination of such an endpoint may cause the next sub-test of the process 900 to begin.

Figure 16A:
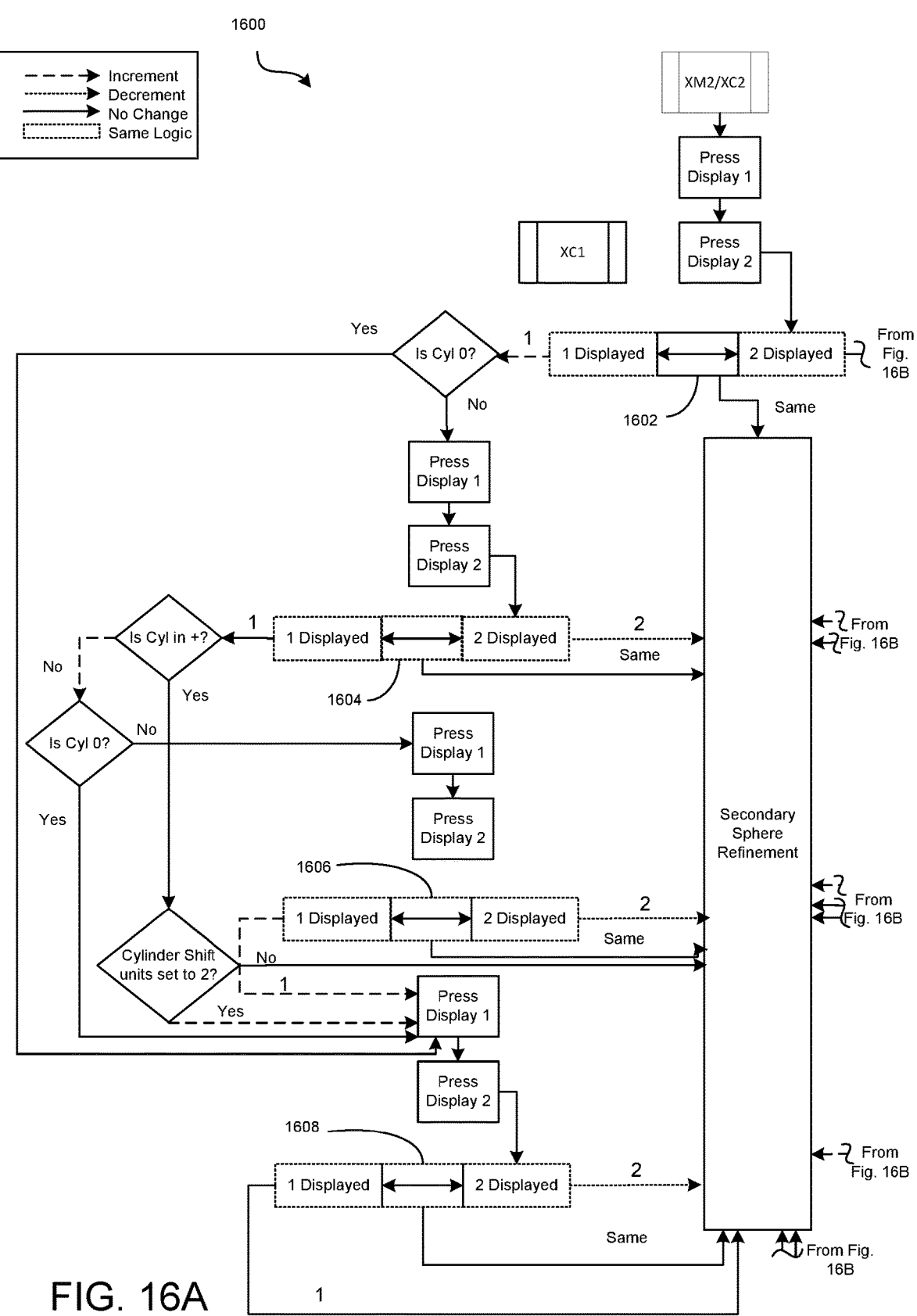
FIG. 16A is a first portion of a flowchart of a process that can be implemented by the system of FIG. 7 for performing a secondary sphere refinement test, according to an exemplary embodiment.
Figure 16B:
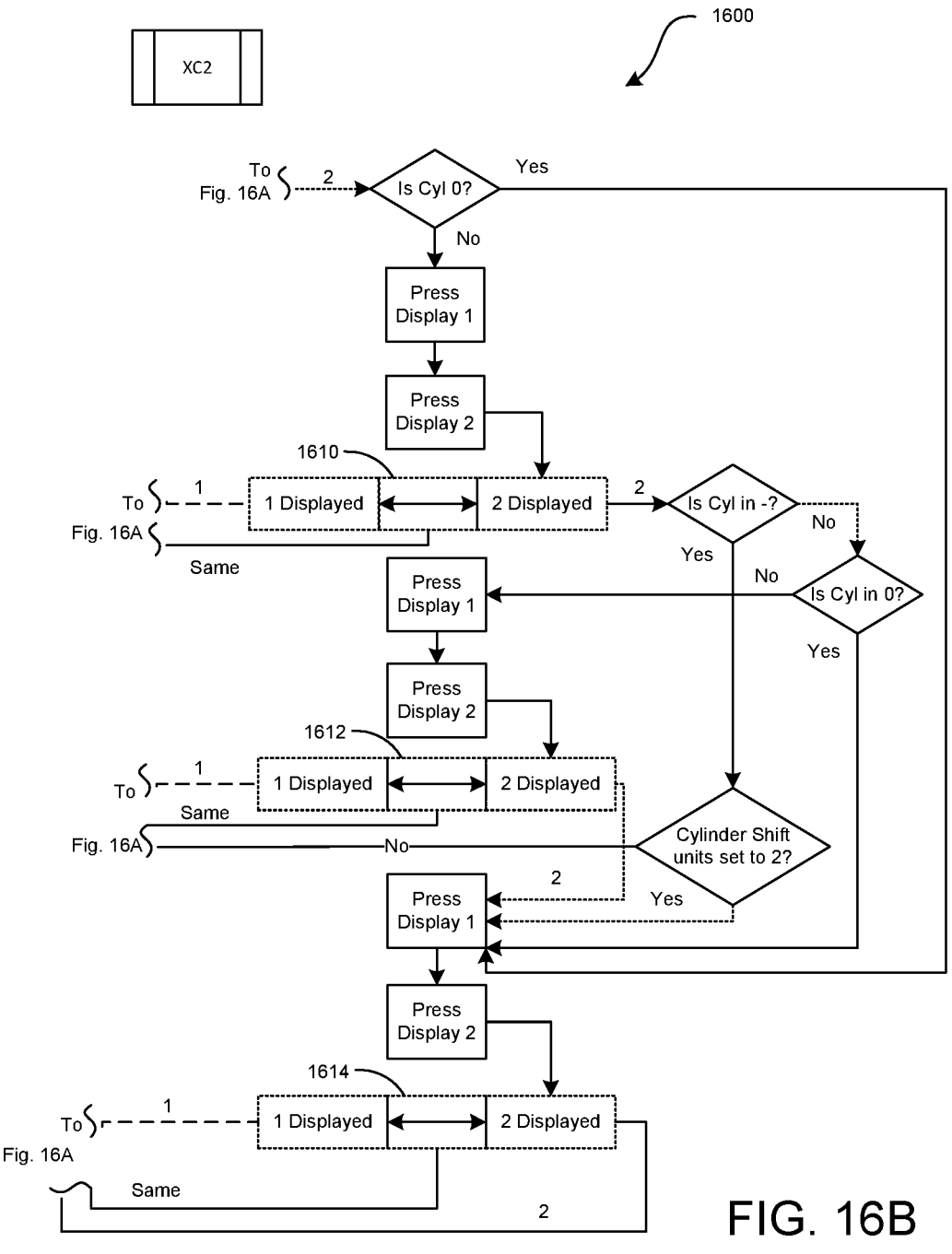
FIG. 16B is a second portion of the flowchart of FIG. 16A showing a process that can be implemented by the system of FIG. 7 for performing a secondary sphere refinement test, according to an exemplary embodiment.

Referring now to FIGS. 16A-B, a flowchart of a process 1600 that can be implemented for administering secondary sphere refinement test is shown. The process 1600 may be administered by the secondary sphere refinement tester 732 of the system 700, and may also include other components of the system 700. Additionally, the secondary sphere refinement test of the process 1600 may incorporate visual references displayed by the display device 754 that include one or more colors similar to the visual reference 602 as shown in FIG. 6. Generally, the secondary sphere refinement test of the process 1600 is conducted to correct for any changes that occurred during the first sphere and axis tests of the processes 1100 and 1200, respectively, and may also be administered to a single eye at a time. In conducting the process 1600 for the secondary sphere refinement test, the system 700 may present to the user (e.g., by pressing "Display 1" and "Display 2") characters displayed on colored backgrounds, with the backgrounds typically red and green (e.g., display 1602, display 1604, display 1606, display 1608, display 1610, display 1612, and display 1614). The patient may be asked by the test administrator which color appears clearer (e.g., 1, 2, or same), and the test administrator can provide an input (e.g., 1, 2, or same) to the input device 710 corresponding to the feedback of the patient. The input device 710 may then communicate a signal to the control box 756 so as to adjust the lenses of the phoropter 748, as well as the display device 754 to update the visual reference displayed to the patient. The secondary sphere refinement tester 732 may be configured to generate an updated GUI to the input device 710 for viewing by the test administrator. This process may be repeated until an endpoint is determined for the process 1600, with the endpoint determined by the endpoint analyzer circuit 718. The determination of such an endpoint may conclude the process 1600 with the results of the process 1600 saved by the test result storage database 720 and allow the next sub-test of the process 900 to begin. The secondary sphere refinement test of the process 1600 may also include limitations. For example, the patient may be allowed to select a color that is more clear (e.g., green or red) up to four times, but the patient may only receive a change of +/−0.75D of sphere. Additionally, the process 1600 may be configured such that the process 1600 will be ended should the patient select a first color (e.g. green) and then immediately after select a second color (e.g. red). Additionally, the process 1600 may include alternative steps not shown in FIGS. 16A-B that may be implemented should the patient be unable to identify large characters (e.g. an "8") or distinguish between colors. Such alternative steps may include those similar to the steps previously described including a patient selecting whether an "option 1" or an "option 2" appears clearer.

Figure 17:
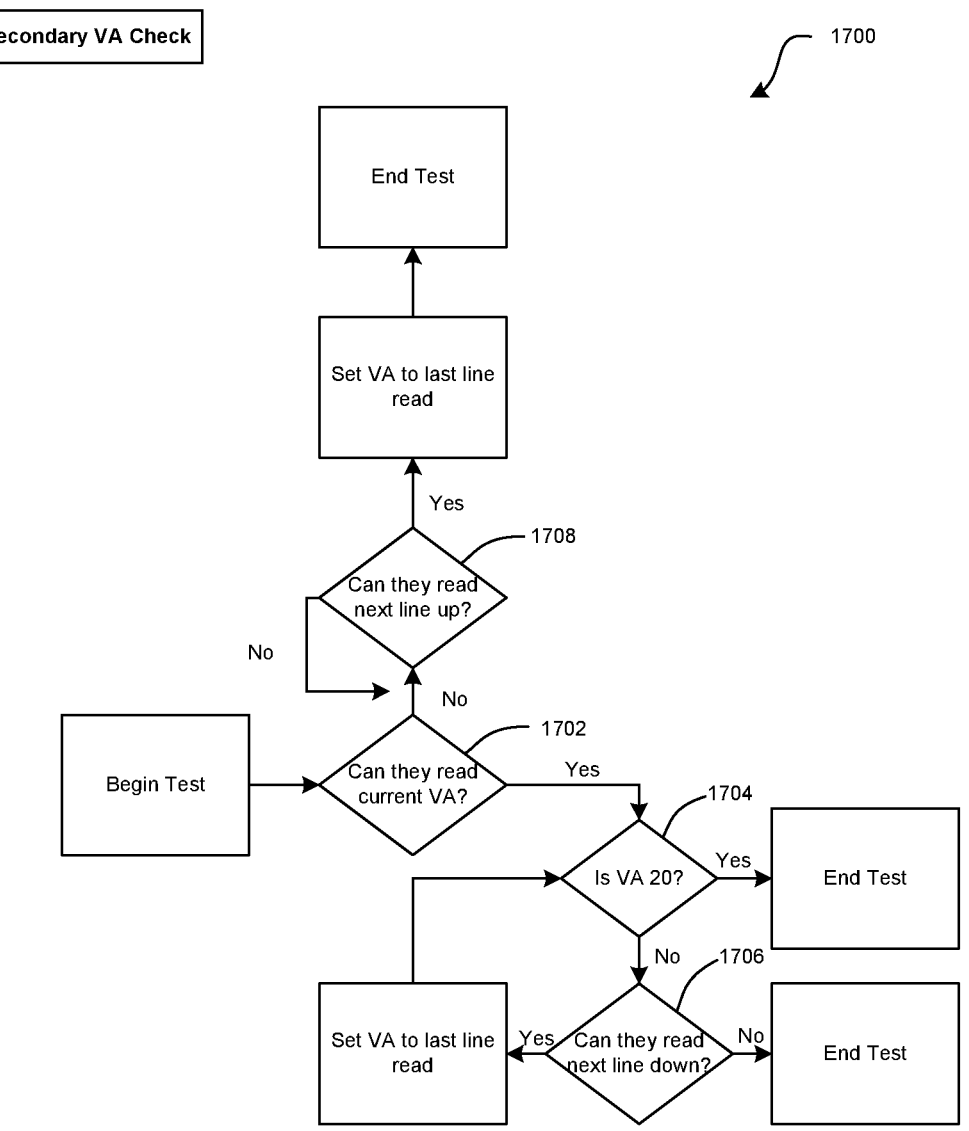
FIG. 17 is a flowchart of a process that can be implemented by the system of FIG. 7 for performing a secondary visual acuity check, according to an exemplary embodiment.

Referring now to FIG. 17, a flowchart of a process 1700 that can be implemented for administering a secondary VA check test is shown. The process 1700 of FIG. 17 may be implemented by the secondary VA tester 734 in conjunction with other components of the system 700. Additionally, the secondary VA check may be performed for a single eye of the patient at a time. The process may begin by displaying a VA chart (e.g., VA display 1002, VA display 1004, VA display 1006, and VA display 1008) and determining whether the patient can read the current VA at decision 1702. If yes, the process 1700 proceeds to decision 1704. If the VA is 20, process 1700 may be completed. If VA is not 20, it is determined if the patient can read the next line down on the VA chart at decision 1706. If not, the process 1700 may be completed. If yes, the VA may be set to the last line read by the patient, and the process 1700 may revert back to decision 1704. If, at decision 1702, the patient cannot read the current VA, it may be determined whether the patient can read the next line up at decision 1708. If yes, then the VA is set to the last line read by the patient. If not, decision 1708 is repeated until the patient can read the next line up. The process 1700 of the secondary VA check may be the same as or similar to the process 1000 of the initial VA check, and may include similar inputs and outputs. For example, process 1700 may be used in conjunction with various displays (e.g., VA display 1002, VA display 1004, VA display 1006, and VA display 1008). Additionally, the components of the system 700 may also be configured to communicate and perform functions similar to those described previously with reference to the process 1000. Similar to the secondary sphere refinement test of the process 1600, the secondary VA check of the process 1700 may be conducted to confirm results of the initial VA test of the process 1000 and identify any changes that may have occurred.

The processes as shown and described in FIGS. 10-17 may be performed for a single eye at a time in conjunction with the eye selector 722 of the system 700. Additionally, the sub-tests of the process 900 as shown and described in FIGS. 10-17 may be configured to assess the ability of the patient to see far, and may also be referred to as "far tests". In some embodiments, the processes 1000-17000 may be modified or adjusted so as to further assess the ability of a patient to see far, or may be further modified to assess the ability of a patient to see near.

Figure 18:
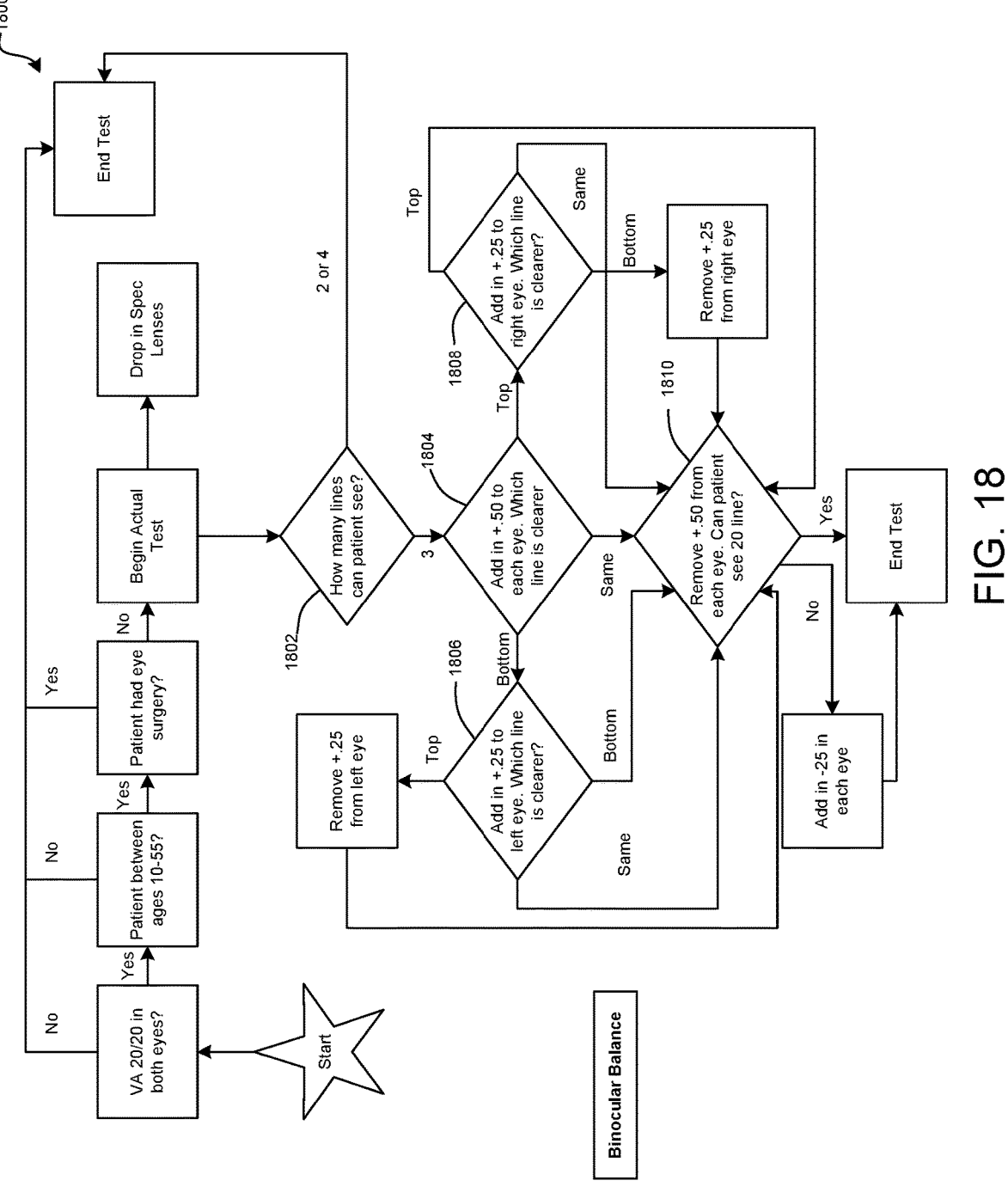
FIG. 18 is a flowchart of a process that can be implemented by the system of FIG. 7 for performing a binocular balance test, according to an exemplary embodiment.

Referring now to FIG. 18, a flowchart of a process 1800 that can be implemented for administering a binocular balance test is shown. The process 1800 may be administered by the binocular balance tester 736 of the system 700, which may function cooperatively with other components of the system 700. Additionally, the binocular balance test of the process 1800 may be conducted for both eyes of the patient simultaneously. Generally, the purpose of the binocular balance test of the process 1800 is to very that, with both eyes of the patient open, the patient can still see well. For example, many of the sub-tests corresponding to the processes 1000-1700 as shown and described previously may be administered to a single eye of the patient at a time. The process 1800 for the binocular balance test ensures that the patient may still see clearly with both eyes open following the various single-eye sub-tests conducted previously. The process 1800 may conclude similar to the processes shown and described previously, with the determination of an endpoint by the endpoint analyzer circuit 718 of the system 700. The process 1800 may include the test administrator asking the patient for feedback given a set of conditions (e.g., at decision 1802, decision 1804, decision 1806, decision 1808, and decision 1810), and then providing an input to the input device 710 indicative of the patient feedback and causing the system 700 to produce a second set of conditions for which the process may be repeated. This may further include the input device 710 communicating various signals to the control box 756 (to adjust the phoropter 748) and the display device 754 (to display an updated visual reference). The binocular balance tester 736 may be configured to prepare an updated GUI to be displayed by the input device 710. The determination of such an endpoint may correspond to a confirmation that the patient can see clearly with both eyes, or an indication that is unable to, and corresponding data may be saved by the test result storage database 720. The next step of the process 900 may then begin.

Following the binocular balance test of process 1800 as shown and described previously, the process 900 may include a subjective comparison test. The subjective comparison test may be administered by the subjective comparison tool 738 of the system 700 and similar to the previous processes as shown and described, may incorporate various additional components of the system 700. For example, the subjective comparison test may be similar to sub-tests of the processes shown and described previously in which the test administrator may ask a patient for feedback regarding the vision of the patient under a first set of conditions and/or a second set of conditions. The test administrator may then provide an input to the input device 710 indicative of the feedback provided by the patient. The input device 710 may subsequently communicate a signal to the control box 756 to adjust the lenses of the phoropter 748 and a signal to the display device 754 to update the visual reference. The subjective comparison tool 738 may be configured to generate an updated GUI to be displayed by the input device 710. Generally, the subjective comparison test may be conducted to show the patient differences between what they were able to see with their previous prescription (or lack of) and what they will be able to see with what the automated subjective refraction test of the process 900 suggests their new prescription for corrective lenses will be. However, in some embodiments, the medical professional 758 may guide the patient toward a different prescription, for example to address a specific medical condition. In some embodiments, the subjection comparison test of the process 1800 may conclude with and endpoint determined by the endpoint analyzer circuit 718 of the system 700, or may conclude with the patient providing an indication to the test administrator that the new prescription improves the vision of the patient. The conclusion of the process 1800 may begin the next step/sub-test in the process 900.

Figure 19:
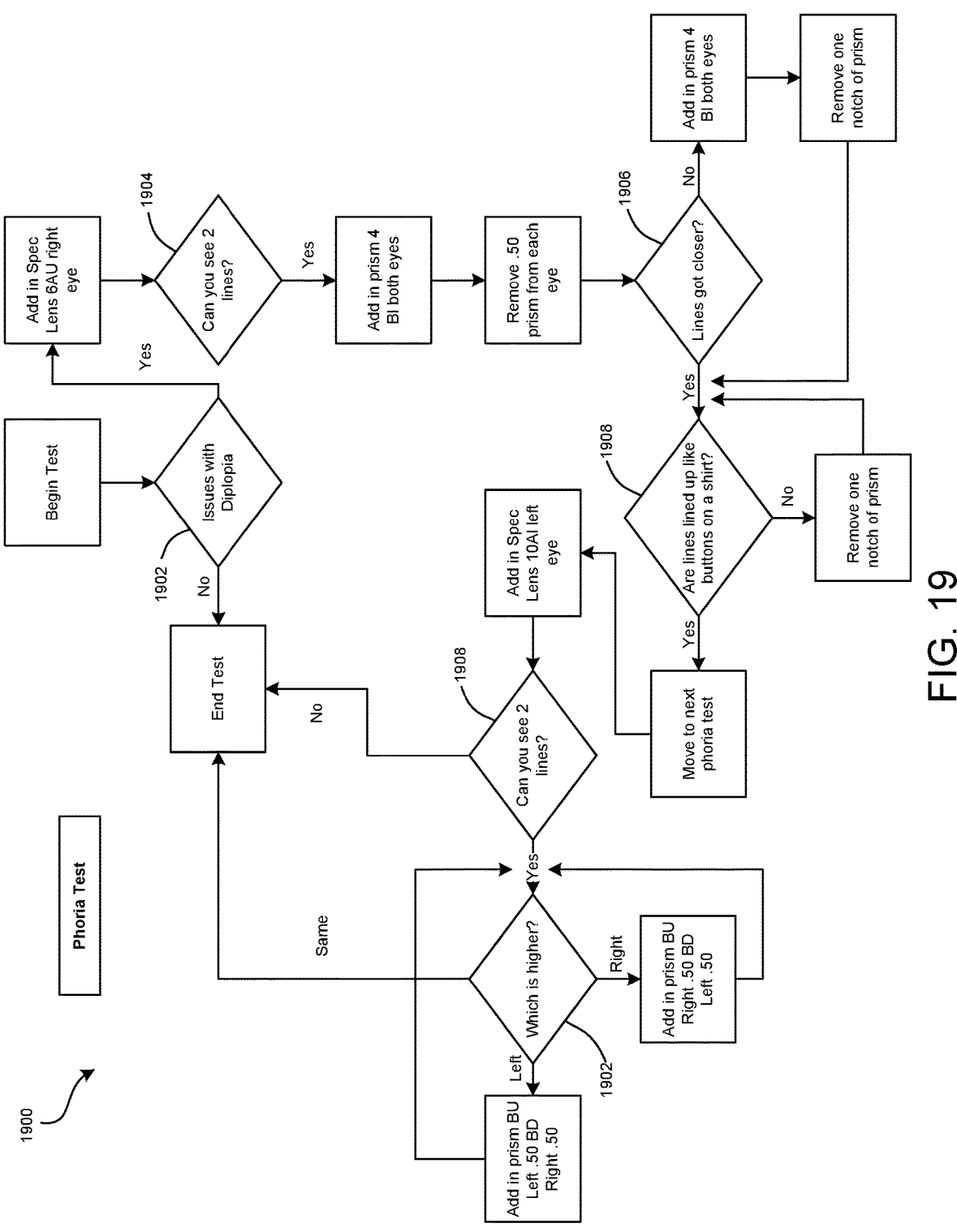
FIG. 19 is a flowchart of a process that can be implemented by the system of FIG. 7 for performing a phoria test, according to an exemplary embodiment.

Referring now to FIG. 19, a flowchart of a process 1900 that can be implemented for administering a phoria test is shown. The process 1900 for administering the phoria test may be conducted by the phoria tester 740 of the system 700 in conjunction with other components. For example, the phoria test may be similar to the binocular balance test of the process 1800 and/or other sub-tests of the processes shown and described previously in which the test administrator may ask a patient for feedback (e.g., at decision 1902, decision 1904, decision 1906, decision 1908, decision 1910, and decision 1912) regarding the vision of the patient under a first set of conditions and/or a second set of conditions. The test administrator may then provide an input to the input device 710 indicative of the feedback provided by the patient. The input device 710 may subsequently communicate a signal to the control box 756 to adjust the lenses of the phoropter 748 and signal to the display device 754 to update the visual reference. The phoria tester 740 may be configured to generate an updated GUI to be displayed by the input device 710. Generally, the phoria test is conducted to measure horizontal and vertical phoria, which can be an indication of if a second eye of the patient may not look in the same direction as a first eye of the patient. Accordingly, the phoria test of the process 1900 may be administered to both eyes of the patient at the same time. The process 1900 for administering the phoria test may conclude with the determination of an endpoint by the endpoint analyzer circuit 718 of the system 700. Such a determination of an endpoint of the process 1900 may correspond to collected data measuring the horizontal phoria and the vertical phoria of the eyes of the patient, with said data then stored in the test result storage database 720 of the system 700. Following the determination of an endpoint of the process 1900, the next sub-test of the process 900 may begin.

Figure 20:
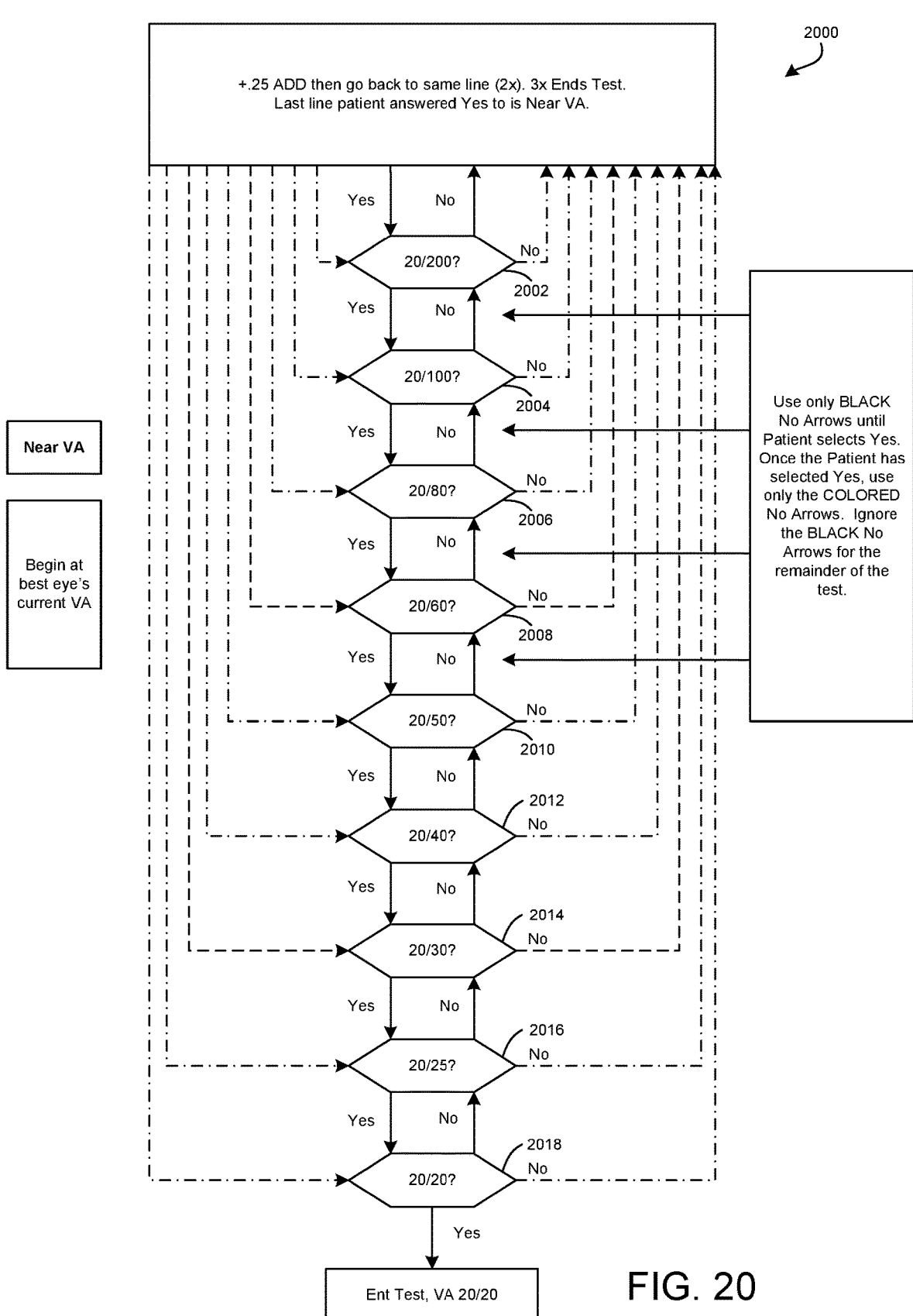
FIG. 20 is a flowchart of a process that can be implemented by the system of FIG. 7 for performing a near visual acuity check, according to an exemplary embodiment.

Referring now to FIG. 20, a flowchart of a process 2000 that can be implemented for administering a near VA test is shown. The process 2000 of the near VA test may be conducted by the near VA tester 742 of the system 700 in conjunction with other components. In administering the near VA test, the test administrator may receive a prompt on the input device 710 including instructions to lower a Near Rod and Card, which may be required for the process 2000. The near VA tester 742 may be configured to generate various GUIs to be displayed by the input device 710 instructing the test administrator to input various information, for example the age of the patient. In response to the test administrator's input of the patient's age, the near VA tester 742 may produce a GUI showing the test administrator various locations on the Near Rod and Card that the test administrator must point at. This GUI may also include instructions for the test administrator to ask the patient to read or identify the portion of the Near Rod and Card being pointed to by the test administrator. The test administrator may then provide an input to the input device 710 indicating if the patient correctly read the corresponding portion of the Near Rod and Card (e.g., as a part of decision 2002, decision 2004, decision 2006, decision 2008, decision 2010, decision 2012, decision 2014, decision 2016, and decision 2018), with the input device 710 communicating data corresponding to the system 700 indicative of the input. The components of the system 700 receiving the data from the input device 710 may include the control box 756 (which may adjust the phoropter 748) as well as the display device 754. The near VA tester 742 may be configured to automatically add an appropriate amount of ADD relative to the age of the patient as provided by the test administrator. Additionally, the near VA tester 742 may be configured to give up to +0.50D prior to ending the test. As mentioned previously with other processes and sub-tests, the near VA test and corresponding process 2000 may conclude upon the determination of an endpoint by the endpoint analyzer of the system 700. Such a determination may include saving an outputted result of the process 2000 to the test result storage database 720, and may also allow for the next sub-test of the process 900 to begin.

Figure 21:
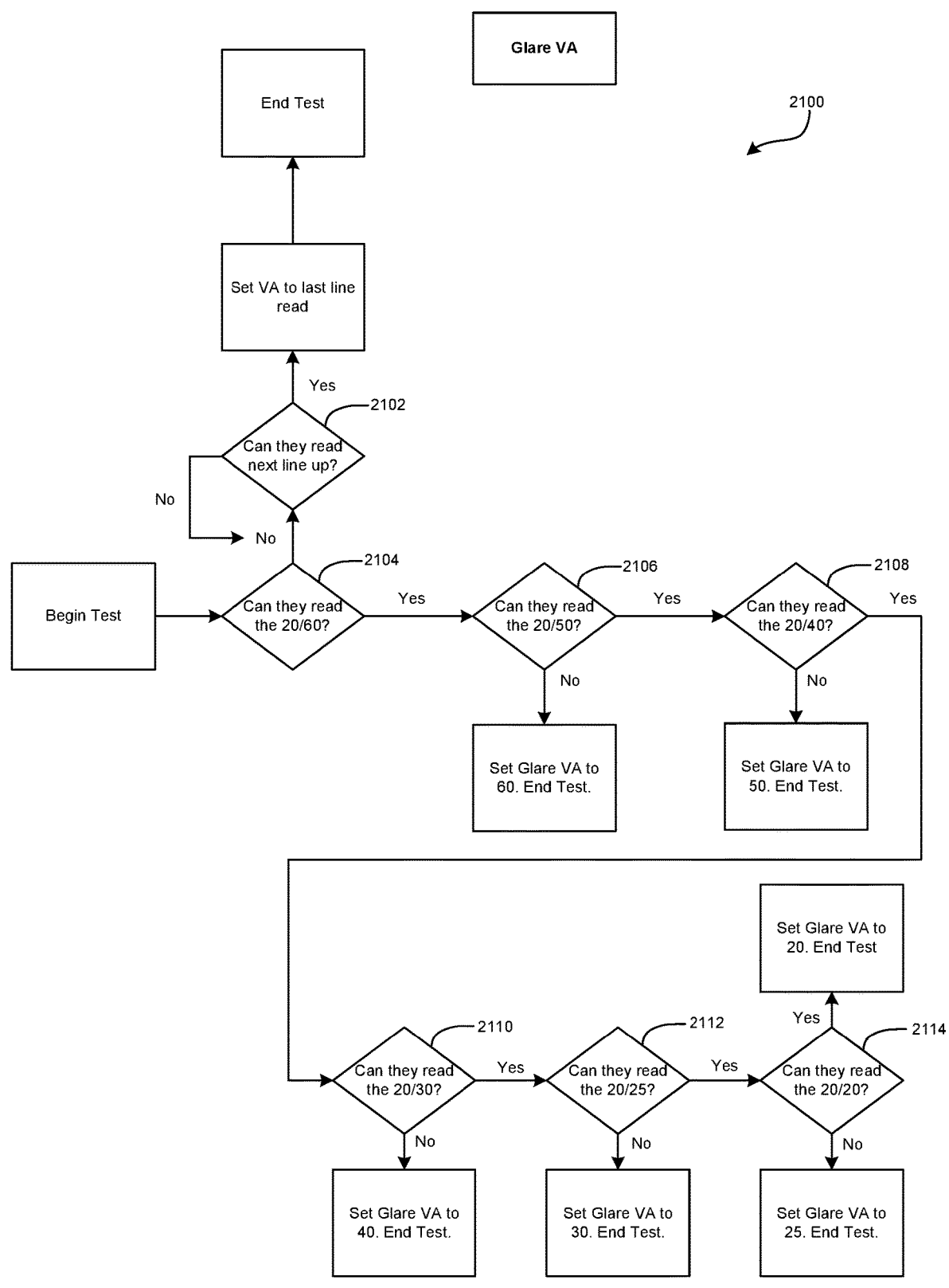
FIG. 21 is a flowchart of a process that can be implemented by the system of FIG. 7 for performing a glare test, according to an exemplary embodiment.

Referring now to FIG. 21, a flowchart of a process 2100 that can be implemented for administering a glare test is shown. The process 2100 of the glare test may be conducted by the glare tester 744 of the system 700 in conjunction with other components of the system. Generally, the glare test may be conducted to measure how well the patient may see at night when looking at a bright light. The process 2100 may include the patient viewing a visual reference displayed by the display device 754 through the phoropter 748 (and/or the subjective lenses 752 or the auxiliary lenses 750) and providing feedback to the test administrator indicating if the patient can read a line of text of the visual reference (e.g., as a part of decision 2102, decision 2104, decision 2106, decision 2108, decision 2110, decision 2112, and decision 2114). The test administrator may then provide an input to the input device 710 indicating if the patient correctly read the text or was unable to, and the input device may then communicate a signal correspond to the input of the test administrator to other components of the system 700. The control box 756 may receive a signal causing it to adjust the phoropter 748 and components thereof, the display device 754 may receive a signal causing it to update the visual reference displayed to the patient, and the glare tester 744 may receive a signal causing it to produce an updated GUI to be viewed by the test administrator on the input device 710. The updated GUI may correspond to the updated visual reference and/or settings of the phoropter 748, and may include instructions for the test administrator to repeat the process. For example, the display device may display a first visual reference including text of a size that corresponds to a VA of 20/60. If the patient correctly reads the text, the visual reference may be updated with the size of the text decreasing until the patient is unable to read the text. However, if the patient is unable to read the text, the visual reference may be updated with the size of the text increasing until the patient is able to read the text. The process 2100 may conclude upon the determination of an endpoint by the endpoint analyzer circuit 718 of the system 700, and may correspond to an input provided by the test administrator to the input device 710 indicating that the patient either correctly identified the text of the visual reference after being unable to do so, or was unable to correctly identify the text of the visual reference after being able to do so. Accordingly, data corresponding with the endpoint of the process 2100 may be stored in the test result storage database 720.

With reference to the process 900 of FIG. 9, the glare test of the process 2100 of the FIG. 21 was the final sub-test (e.g., step) in the process 900. Accordingly, the process 900 may conclude with the conclusion of the process 2100. Upon the conclusion of the process 900, the automated subjective refraction test may be complete. The results of the automated subjective refraction test may then be communicated to the medical professional 758 of the system 700 for further review. The medical professional 758 may contact the patient to discuss the results of the automated subjective refraction test and/or may guide the patient in the direction of the proper corrective lenses based on the results.

Referring now to FIGS. 22-29, GUIs that can be displayed to the test administrator are shown. The GUIs of the FIGS. 22-29 may be generated by the various testers of the test conductor circuit 714 of the system 700, and may further be communicated to the communications interface 746 by the various testers and the communicated to the input device 710. The test administrator may then view the GUIs and provide the inputs requested by the GUIs. Additionally, the GUIs may include instructions for the test administrator to perform various functions (e.g., adjust the Near Rod and Card of the process 2000 for the Near VA test) or include text to be read by the test administrator to the patient. For example, a GUI displayed to the test administrator by the input device 710 may include text instructing the test administrator to ask the patient if "option 1" or "option 2" appears clearer and, upon receiving the feedback from the patient, select a button on the GUI corresponding to the feedback received from the patient.

Figure 22:
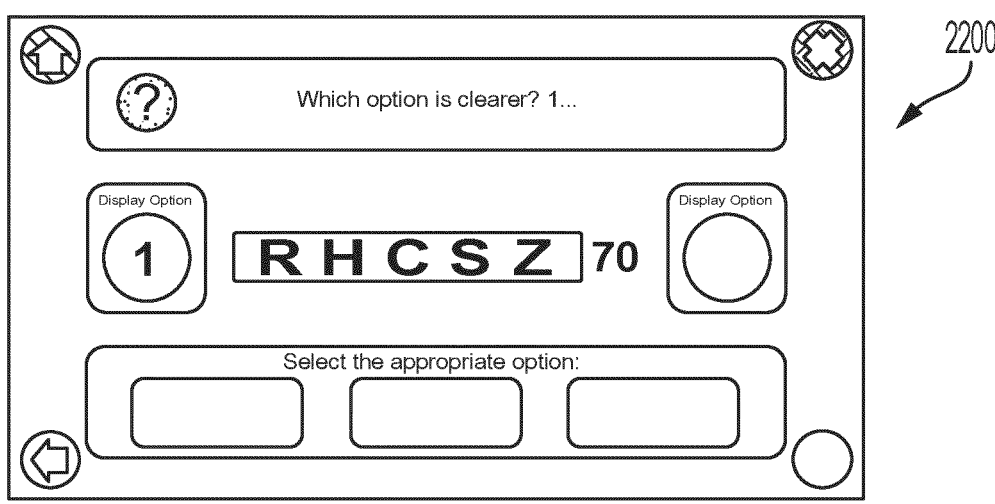
FIG. 22 is an illustration of a graphical user interface (GUI) that can be generated by the system of FIG. 7, according to an exemplary embodiment.
Figure 23:
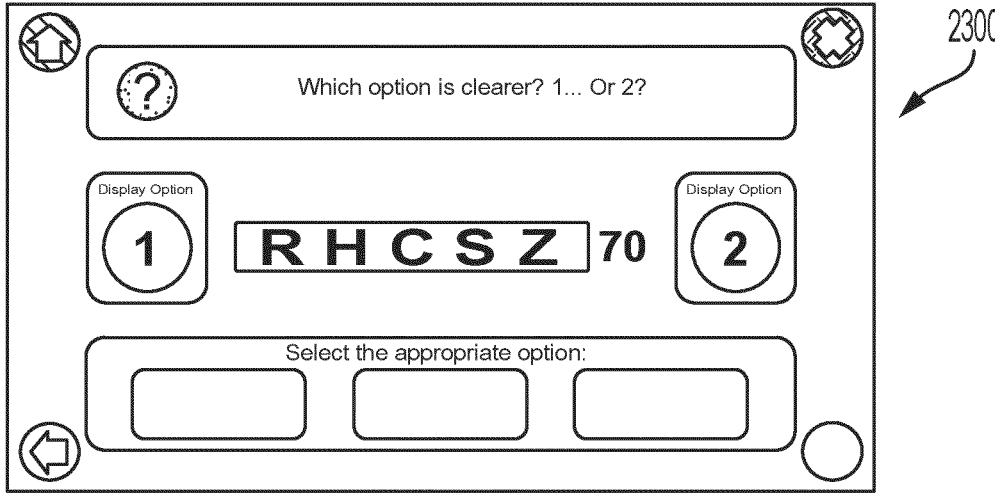
FIG. 23 is another illustration of a GUI that can be generated by the system of FIG. 7, according to an exemplary embodiment.
Figure 24:
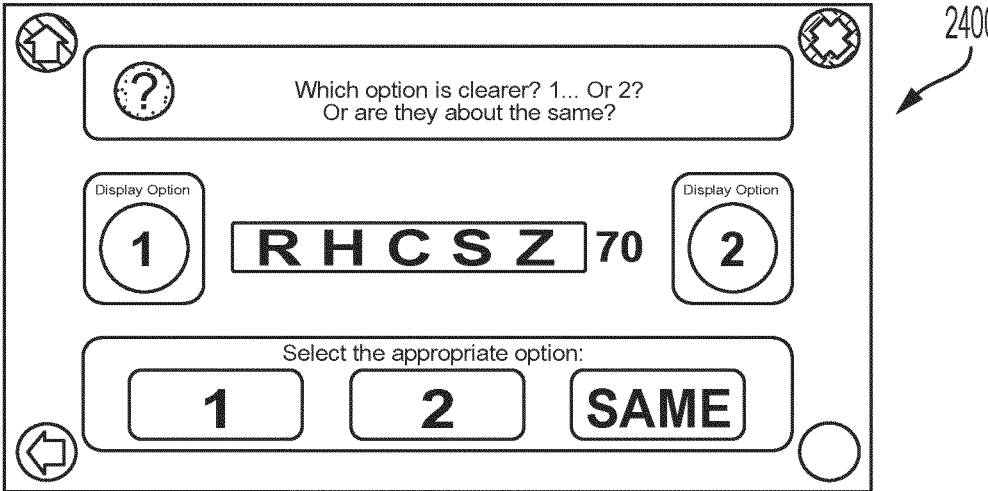
FIG. 24 is still another additional illustration of a GUI that can be generated by the system of FIG. 7, according to an exemplary embodiment.

Referring now to FIGS. 22-24, a series of GUIs is shown. The GUIs shown may be communicated to the GUI from the communications interface 746 to the input device 710 of the system 700. Additionally, the GUIs 2200, 2300, and 2400 of FIGS. 22-24 may correspond to an initial sphere refinement test such as that of the process 1100 as shown and described in FIG. 11 and may be generated by the initial sphere refinement tester 726. The process 1100 may include the test administrator displaying an "option 1" and an "option 2 to the patient, with both "option 1" and "option 2" corresponding to a set of conditions. Similar to previous examples, when presented "option 1" the patient may observe a chart 1 through lens A, and then a chart 2 through lens A. The patient may then be presented "option 2" in which the patient is presented lens B such that the patient may view chart 2 through the lens B and compare the effect of lens A to lens B on chart 2. The sets of conditions corresponding to both "option 1" and "option 2" may include various combinations of the subjective lenses 752 and/or the auxiliary lenses 750 of the phoropter 748, and may be manipulated by the control box 756. Additionally, "option 1" and "option 2" may also include a visual reference, where the visual reference may be updated from "option 1" to "option 2". In some embodiments, if the visual reference is changing (e.g., updated from "option 1" to "option 2") while the patient is asked to observe it, the subjective and/or auxiliary lenses are not be changed. Similarly, if the subjective and/or auxiliary lenses are changing (e.g., adjusted from "option 1" to "option 2") while the patient is observing a visual reference through them, the visual reference may not be changed. The visual reference and the subjective and/or auxiliary lenses may only be changed at the same time when a system such as the system 700 is transitioning from one sub-test to the next.

The GUI 2200 as shown in FIG. 22 is shown to include "option 1" displayed on the left portion of the GUI. The test administrator may be instructed to select the button labeled "option 1" in order to present the first set of conditions corresponding to "option 1" to the patient while verbally informing the patient that the set of conditions presented is to be referred to as "option 1". The GUI may not include the button corresponding to "option 2" to ensure that the test administrator waits a sufficient amount of time between presenting "option 1" and "option 2" to the patient so as to avoid confusion. For example, only once the test administrator presses the button to display "option 1" to the patient will the test administrator be presented an updated GUI replacing the GUI 2200 to the input device 710 that includes the button corresponding to "option 2".

The GUI 2300 as shown in FIG. 23 is shown to include "option 1" displayed on the left portion of the GUI as well as "option 2". The test administrator may be instructed to select the button labeled "option 2" in order to present the second set of conditions corresponding to "option 2" to the patient while verbally informing the patient that the set of conditions presented is to be referred to as "option 2". In some embodiments, the GUI 2300 may be configured such that the test administrator must have pressed the button shown to include "option 1" thus presenting "option 1" to the patient before the button shown to include "option 2" will enable (e.g., be presented to the test administrator on the GUI 2300). The GUI may not include the buttons allowing for the test administrator to input the patient's response so as to ensure that the patient has sufficient time to view both "option 1" and "option 2" and the test administrator doesn't provide an input prematurely. For example, only once the test administrator presses the button to display "option 2" to the patient will the test administrator be presented an updated GUI including buttons having patient answer selections enabled allowing the test administrator to provide an input corresponding to the feedback provided by the patient.

The GUI 2400 as shown in FIG. 24 is shown to include buttons corresponding to the feedback that may be provided to the test administrator by the patient regarding "option 1" and "option 2" as presented to the patient. The GUI 2200 may include instructions for the test administrator to be read to the patient indicating that both "option 1" and "option 2" will be presented to the patient and that the patient needs to indicate to the test administrator if "option 1" or "option 2" appeared clearer, or if they appeared substantially the same. The buttons of the GUI 2400 correspond to the possible answers of the patient, and upon receiving feedback from the patient, the test administrator may be instructed to press the button corresponding to the feedback from the patient. The GUI 2400 and the input provided by the test administrator may then be communicated by the input device 710 to the other components of the system 700.

Figures 25, 26:
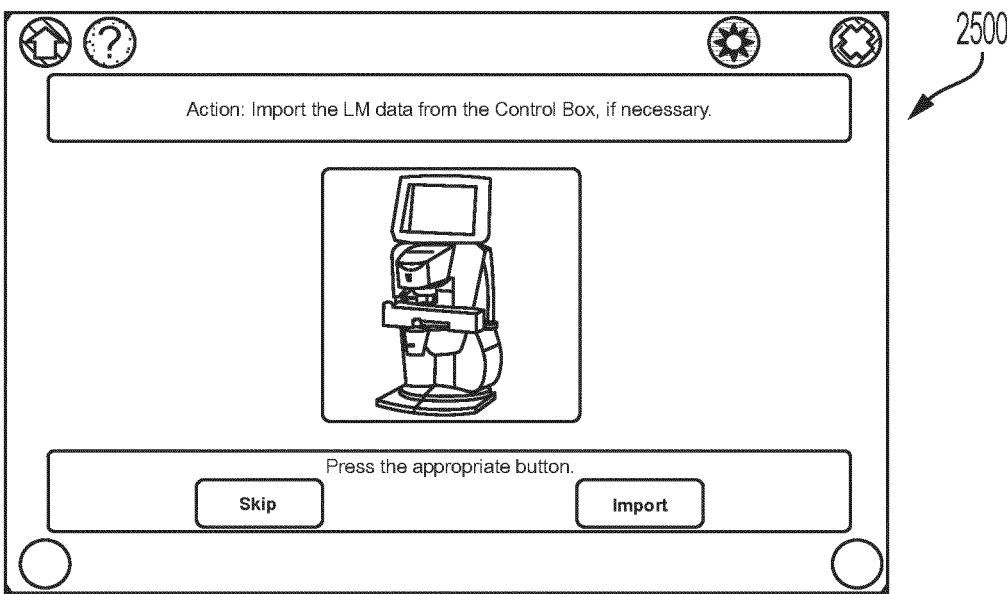
FIG. 25 is yet another additional illustration of a GUI that can be generated by the system of FIG. 7, according to an exemplary embodiment.
FIG. 26 is still a further additional illustration of a GUI that can be generated by the system of FIG. 7, according to an exemplary embodiment.

Referring now to FIG. 25, a GUI 2500 is shown providing instructions to the test administrator for preparing a system such as the system 700 for an automated refraction test. As shown in FIG. 25, the GUI 2500 includes instructions that the test administrator is to take an action, with the action being "import the LM data from the control box, if necessary." The control box of the GUI 2500 may correspond to the control box 756 of the system 700. Additionally, the GUI 2500 includes an image which may show the control box 756 and/or other components of the system 700. The test administrator may complete the action by selecting the button of the GUI 2500 marked "import" or may elect to bypass the instructions of the GUI 2500 by selecting the button marked "skip". Once the test administrator selects one of the buttons of the GUI 2500, the corresponding input may be communicated to other components of the system 700 and the GUI 2500 may be replaced by a new GUI providing further instructions to the test administrator.

Referring now to FIG. 26, a GUI 2600 is shown that may correspond to the initial VA check of the process 1000. The GUI 2600 may be produced by the initial VA tester 724, and may have been communicated to the input device 710 via the communications interface 746 of the system 700. The GUI 2600 can include instructions to be read by the test administrator to the patient including that the patient should "Read the smallest line you can see clearly on the chart". The GUI 2600 may also include a chart corresponding to a chart displayed by the display device 754 as a visual reference to the patient. The GUI 2600 further includes buttons corresponding to each line of the chart displayed to the patient as the visual reference, as well as a button marked "none". The test administrator may be instructed to select the button corresponding to the smallest line of text that the patient indicates s/he is able to see clearly on the chart, or select "none" if the patient is unable to see any of the lines of text on the chart clearly. Once the test administrator selects one of the buttons of the GUI 2600, the corresponding input may be communicated to other components of the system 700 and the GUI 2600 may be replaced by a new GUI providing further instructions to the test administrator.

Figure 27:
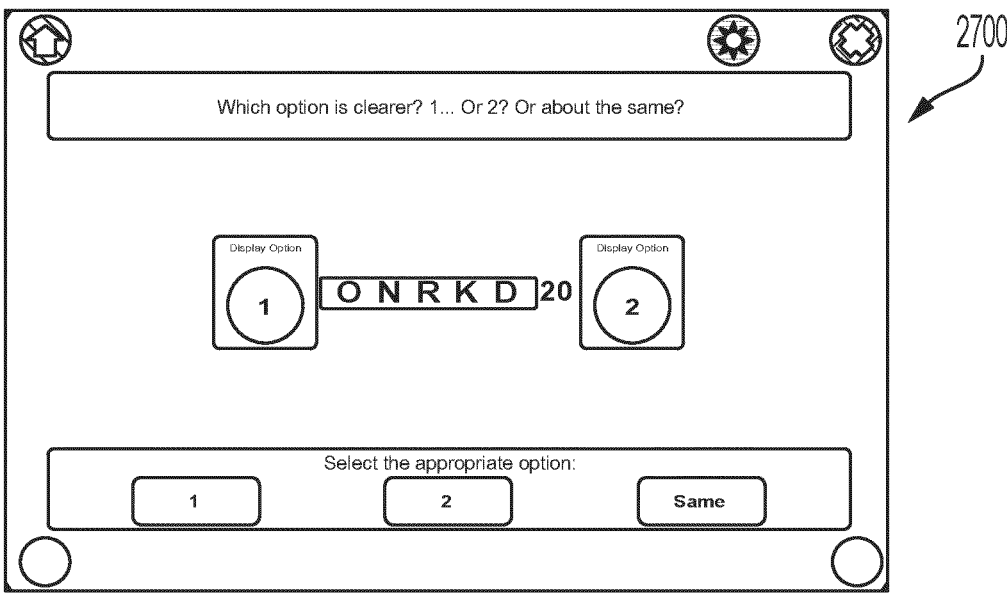
FIG. 27 is yet a further additional illustration of a GUI that can be generated by the system of FIG. 7, according to an exemplary embodiment.

Referring now to FIG. 27, a GUI 2700 is shown that may correspond to an initial sphere refinement test such as that of the process 1100 as shown and described in FIG. 14. The GUI 2700 is shown to include text to be read to the patient by the test administrator asking "Which option is clearer? 1 . . . Or 2? Or about the same?" The GUI 2700 may further include a display corresponding to the options 1 and 2 displayed to the patient via the visual reference of the display device 754. Upon the patient providing an indication of whether option 1 or 2 appears clearer, or if they appear substantially the same, the test administrator may be instructed to select the button configured on the bottom portion of the GUI 2700 corresponding to the feedback of the patient. Once the test administrator selects one of the buttons of the GUI 2700, the corresponding input may be communicated to other components of the system 700 and the GUI 2700 may be replaced by a new GUI providing further instructions to the test administrator.

Figure 28:
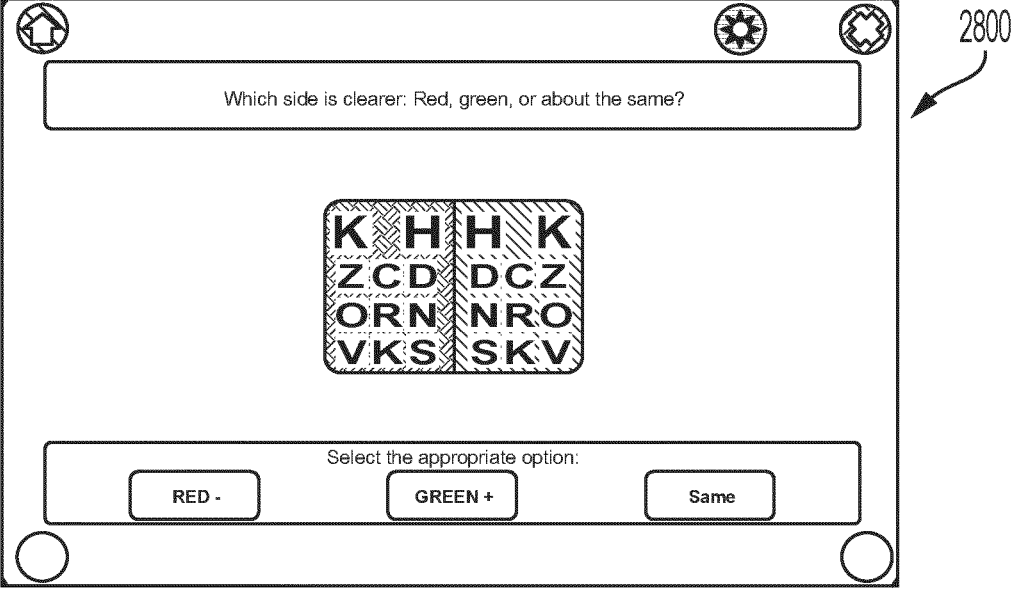
FIG. 28 is still yet a further additional illustration of a GUI that can be generated by the system of FIG. 7, according to an exemplary embodiment.

Referring now to FIG. 28, a GUI 2800 is shown that may correspond to the secondary sphere refinement test of the process 1600 as shown and described in FIGS. 16A-B. The GUI 2800 is shown to include text to be read to the patient by the test administrator stating "Which side is clearer: Red, green, or about the same?" The GUI 2800 can also include a display of a visual reference corresponding to that of the user, where similar to the visual reference 602 of FIG. 6, the visual reference displayed by the display device 754 may include one or more colors. The GUI 2800 may further include buttons corresponding to the possible answers received as feedback from the patient indicating whether one side or the other of the visual reference appears clearer, or if they appear about the same. The test administrator may be instructed to select the button corresponding to the feedback provided by the patient in response to the question asked by the test administrator, as read from the upper portion of the GUI 2800. Once the test administrator selects one of the buttons of the GUI 2800, the corresponding input may be communicated to other components of the system 700 and the GUI 2800 may be replaced by a new GUI providing further instructions to the test administrator.

Figure 29:
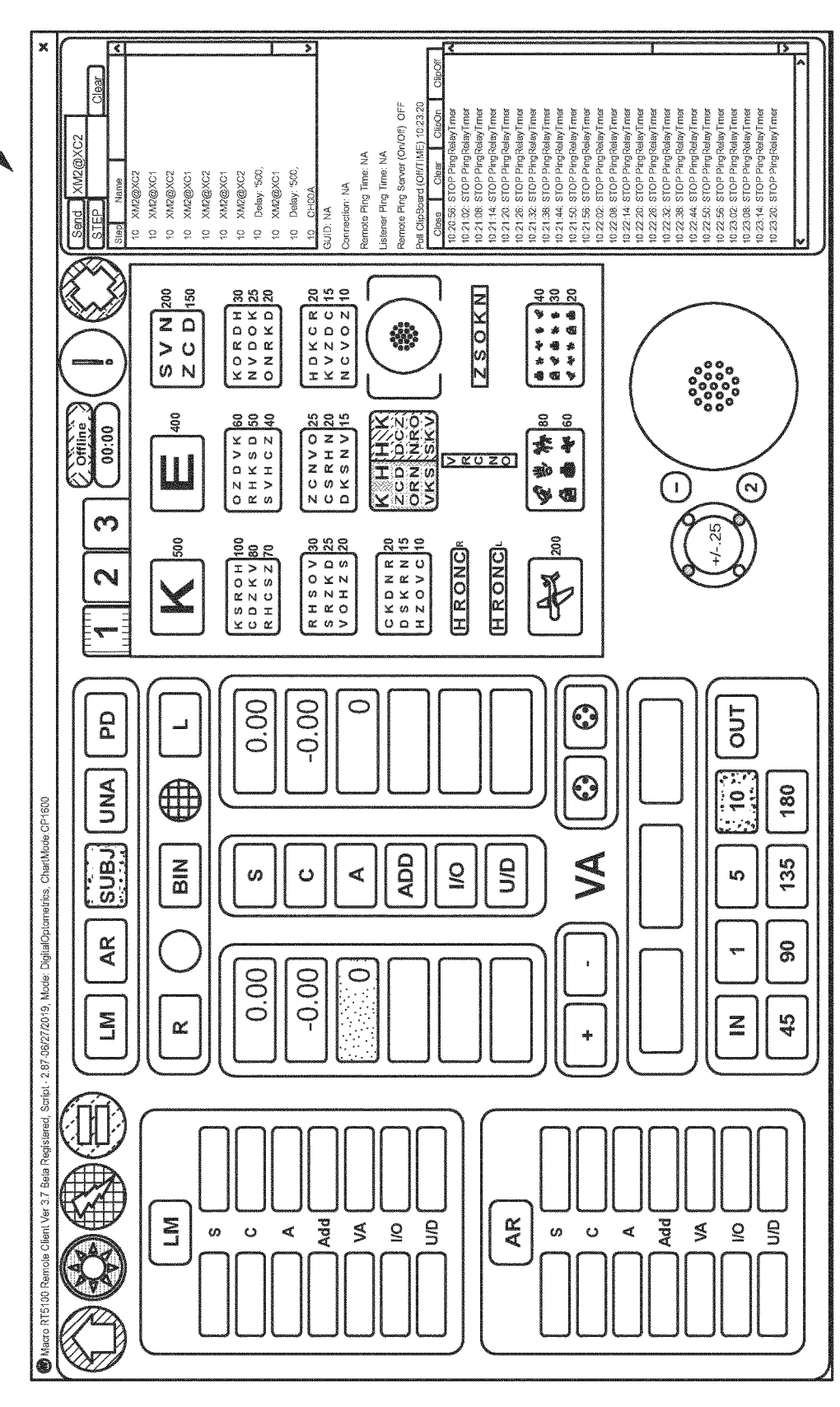
FIG. 29 is another illustration of a GUI that can be generated by the system of FIG. 7, according to an exemplary embodiment.

Referring now to FIG. 29, a GUI 2900 is shown that may be communicated by the test conductor circuit 714 to the input device 710 upon receiving a signal indicating that a test administrator with expertise in optometry, ophthalmology, or refraction testing may be administering an automated subjective refraction test to a patient. Given that the test administrator may have expertise in related fields, the test conductor circuit 714 may generate the GUI 2900 and communicated the GUI 2900 to the input device 710. The GUI 2900 is shown to include additional information regarding the automated subjective refraction test and the system 700 that may confuse a test administrator without expertise in related fields. For example, the GUIs of FIGS. 22-28 include simplified information and basic instructions for the test administrator, whereas the GUI of FIG. 2900 includes detailed and sophisticated information corresponding to the sub-tests of the process 900 for administering an automated subjective refraction test.

Referring now to FIG. 30, the input device 710 is shown. The input device 710 may be the same as and/or similar to the input device 710 as shown and described previously, for example with reference to the system 700 of FIG. 7. As shown in FIG. 30, the input device 710 may be a tablet configured to be portable such that it may be held and carried by the test administrator while performing various tasks associated with the automated subjective refraction test. For example, the test administrator may hold the input device 710 such that the test administrator may view instructions displayed on a GUI outlining steps for properly positioning the patient for the automated subjective refraction test (e.g., adjusting the forehead rest 204 of the phoropter 102 as shown and described previously. Additionally, the input device 710 may be configured to send and receive wireless signals with various other devices including, for example, components of the system 700. The input device 710 may communicate signals to and from the control box 756, the display device 754, and/or the medical professional 758. In some embodiments, the input device 710 may include devices other than that as shown and described in FIG. 30. For example, the input device 710 may be a desktop computer, a laptop computer, a smartphone, or other device configured to be implemented in conjunction with the system 700.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the disclosure as recited in the appended claims.

It should be noted that the term "exemplary" and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

The term "or," as used herein, is used in its inclusive sense (and not in its exclusive sense) so that when used to connect a list of elements, the term "or" means one, some, or all of the elements in the list. Conjunctive language such as the phrase "at least one of X, Y, and Z," unless specifically stated otherwise, is understood to convey that an element may be either X, Y, Z; X and Y; X and Z; Y and Z; or X, Y, and Z (i.e., any combination of X, Y, and Z). Thus, such conjunctive language is not generally intended to imply that certain embodiments require at least one of X, at least one of Y, and at least one of Z to each be present, unless otherwise indicated.

References herein to the positions of elements (e.g., "top," "bottom," "above," "below") are merely used to describe the orientation of various elements in the FIGURES. It should be noted that the orientation of various elements may differ according to other exemplary embodiments, and that such variations are intended to be encompassed by the present disclosure.

The hardware and data processing components used to implement the various processes, operations, illustrative logics, logical blocks, modules and circuits described in connection with the embodiments disclosed herein may be implemented or performed with a general purpose single- or multi-chip processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein. A general purpose processor may be a microprocessor, or, any conventional processor, controller, microcontroller, or state machine. A processor also may be implemented as a combination of computing devices, such as a combination of a DSP and a microprocessor, a plurality of microprocessors, one or more microprocessors in conjunction with a DSP core, or any other such configuration. In some embodiments, particular processes and methods may be performed by circuitry that is specific to a given function. The memory (e.g., memory, memory unit, storage device) may include one or more devices (e.g., RAM, ROM, Flash memory, hard disk storage) for storing data and/or computer code for completing or facilitating the various processes, layers and modules described in the present disclosure. The memory may be or include volatile memory or non-volatile memory, and may include database components, object code components, script components, or any other type of information structure for supporting the various activities and information structures described in the present disclosure. According to an exemplary embodiment, the memory is communicably connected to the processor via a processing circuit and includes computer code for executing (e.g., by the processing circuit or the processor) the one or more processes described herein.

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products including machine-readable media for carrying or having machine-executable instructions or data structures stored thereon. Such machine-readable media can be any available media that can be accessed by a general purpose or special purpose computer or other machine with a processor. By way of example, such machine-readable media can include RAM, ROM, EPROM, EEPROM, or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

Although the figures and description may illustrate a specific order of method steps, the order of such steps may differ from what is depicted and described, unless specified differently above. Also, two or more steps may be performed concurrently or with partial occurrence, unless specified differently above. Such variation may depend, for example, on the software and hardware systems chosen and on designer choice. All such variations are within the scope of the disclosure. Likewise, software implementations of the described methods could be accomplished with standard programming techniques with rule-based logic and other logic to accomplish the various connection steps, processing steps, comparison steps, and decision steps.

What is claimed:

1. A system for administering a subjective refraction test, the system comprising:

a phoropter having a plurality of lenses that are adjustable to affect the vision of a patient; a display configured to display a plurality of visual references viewable by the patient; and a computing device coupled to the phoropter and the display, the computing device configured to:

generate a first set of conditions for a first test and a first plurality of response fields, the first set of conditions corresponding to a first visual reference viewed by the patient through a first combination of the plurality of lenses and the first plurality of response fields configured to receive first feedback from the patient indicative of the patient's vision under the first set of conditions;

generate a first graphical user interface (GUI) for display on the computing device, the first GUI comprising a first script, the first visual reference, and the first plurality of response fields, the first script comprising a string of alphanumeric characters to be read and each of the first plurality of response fields comprising at least one of a numerical indicator or a string of alphanumeric characters; receive, via an interaction with at least one of the first plurality of response fields displayed on the first GUI, a first input indicative of the patient's vision under the first set of conditions;

automatically update and display, based on the first input, the first GUI to include an updated first visual reference, the updated first visual reference also viewable by the patient via the display;

iteratively update, based on the first input, a second combination of the plurality of lenses while maintaining the first GUI having the first script, the updated first visual reference, and the first plurality of response fields, and receive feedback from the patient until a predefined number of responses are received from the patient during the first test to determine an endpoint for the first test, wherein the second combination of the plurality of lenses is different than the first combination of the plurality of lenses;

automatically generate based on the determined endpoint for the first test to transition to a second test from the first test, a second set of conditions for the second test and a second plurality of response fields, the second set of conditions comprising a second visual reference viewed by the patient and a third combination of the plurality of lenses, and at least one of the second plurality of response fields configured to receive second feedback indicative of the patient's vision under the second set of conditions, wherein the third combination of the plurality of lenses is different than the first and the second combinations of the plurality of lenses;

generate a second GUI for display by the computing device, the second GUI comprising a second script, the second visual reference, and the second plurality of response fields, the second script comprising a string of alphanumeric characters to be read, the second script different than the first script, and each of the second plurality of response fields comprising at least one of a numerical indicator or a string of alphanumeric characters, wherein at least one response field in the second plurality of response fields is different than at least one response field in the first plurality of response fields;

receive, via an interaction with at least one of the second plurality of response fields displayed on the second GUI, an updated input indicative of the patient's vision under the second set of conditions; and determine an endpoint for the second test based on a determined a visual acuity during the second test matching a predefined visual acuity value such that the endpoint for the second test is different than the endpoint for the first test.

2. The system of claim 1, wherein the computing device is configured to subsequently administer a third test subsequent to determining the endpoint for the second test.

3. The system of claim 1, wherein the first set of conditions and the second set of conditions include a combination of subjective lenses and auxiliary lenses of the phoropter.

4. The system of claim 1, wherein the computing device is configured to generate the first visual reference and update the updated first visual reference to be viewable by the patient.

5. The system of claim 1, wherein the first set of conditions includes a first combination of auxiliary lenses, a first combination of subjective lenses, and the first visual reference, and the second set of conditions includes one of a second combination of auxiliary lenses different from the first combination of auxiliary lenses, a second combination of subjective lenses different from the first combination of subjective lenses, or the second visual reference different from the first visual reference.

6. The system of claim 1, further comprising a control box configured to enable wireless communication between one or more of the computing device, the display, and the phoropter.

7. The system of claim 1, wherein a determination of an endpoint for a third test corresponds to receiving a predetermined number of replies from the patient based on a set of conditions for the third test.

8. A method of administering a subjective refraction test, the method comprising:

generating a first set of conditions for a first test and a first plurality of response fields, the first set of conditions corresponding to a first visual reference viewed by a patient through a first combination of a plurality of lenses and the first plurality of response fields configured to receive first feedback from the patient indicative of the patient's vision under the first set of conditions;

generating and displaying a first graphical user interface (GUI) comprising a first script, the first visual reference, and the first plurality of response fields, the first script comprising a string of alphanumeric characters to be read and each of the first plurality of response fields comprising at least one of a numerical indicator or a string of alphanumeric characters;

receiving, via an interaction with at least one of the first plurality of response fields displayed on the first GUI, a first input indicative of the patient's vision under the first set of conditions;

automatically updating and displaying, based on the first input, the first GUI to include an updated first visual reference;

iteratively updating, based on the first input, a second combination of the plurality of lenses while maintaining the first GUI having the first script, the updated first visual reference, and the first plurality of response fields, and receive feedback from the patient until a predefined number of responses are received from the patient during the first test to determine an endpoint for the first test, wherein the second combination of the plurality of lenses is different than the first combination of the plurality of lenses;

automatically generating based on the determined endpoint for the first test to transition to a second test from the first test, a second set of conditions for the second test and a second plurality of response fields, the second set of conditions comprising a second visual reference viewed by the patient and a third combination of the plurality of lenses, and the second plurality of response fields configured to receive second feedback indicative of the patient's vision under the second set of conditions, wherein the third combination of the plurality of lenses is different than the first and the second combinations of the plurality of lenses;

generating and displaying a second GUI comprising a second script, the second visual reference, and the second plurality of response fields, the second script comprising a string of alphanumeric characters to be read, the second script different than the first script, and each of the second plurality of response fields comprising at least one of a numerical indicator or a string of alphanumeric characters, wherein at least one response field of the second plurality of response fields is different than at least one response field of the first plurality of response fields;

receiving, via an interaction with at least one of the second plurality of response fields displayed on the second GUI, an updated input indicative of the patient's vision under the second set of conditions; and determining an endpoint for the second test based on a determined a visual acuity during the second test matching a predefined visual acuity value such that the endpoint for the second test is different than the endpoint for the first test.

9. The method of claim 8, further comprising:

subsequently administering a third test subsequent to determining the endpoint for the second test.

10. The method of claim 8, wherein generating the first set of conditions and generating the second set of conditions includes generating a combination of subjective lenses and auxiliary lenses.

11. The method of claim 8, further comprising:

generating the first visual reference and updating the updated first visual reference to be viewable by the patient.

12. The method of claim 8, wherein the first set of conditions includes a first combination of auxiliary lenses, a first combination of subjective lenses, and the first visual reference, and the second set of conditions includes one of a second combination of auxiliary lenses different from the first combination of auxiliary lenses, a second combination of subjective lenses different from the first combination of subjective lenses, or the second visual reference different from the first visual reference.

13. The method of claim 8, further comprising:

determining an endpoint for a third test responsive to receiving a predetermined number of replies from the patient based on a set of conditions for the third test.

14. A system for administering an automated subjective refraction test, the system comprising:

a processing circuit coupled to a phoropter having a plurality of lenses that are adjustable and a display device configured to display a plurality of visual references, the processing circuit configured to:

generate a first set of conditions for a first test and a first plurality of response fields, the first set of conditions corresponding to a first visual reference viewed by a patient through a first combination of the plurality of lenses and the first plurality of response fields configured to receive first feedback from the patient indicative of the patient's vision under the first set of conditions;

generate a first graphical user interface (GUI) for display, the first GUI comprising a first script, the first visual reference, and the first plurality of response fields, the first script comprising a string of alphanumeric characters to be read and each of the first plurality of response fields comprising at least one of a numerical indicator or a string of alphanumeric characters;

receive, via an interaction with at least one of the first plurality of response fields displayed on the first GUI, a first input indicative of the patient's vision under the first set of conditions;

automatically update and display, based on the first input, the first GUI to include an updated first visual reference;

iteratively update, based on the first input, a second combination of the plurality of lenses while maintaining the first GUI having the first script, the updated first visual reference, and the first plurality of response fields, and receive feedback from the patient until a predefined number of responses are received from the patient during the first test to determine an endpoint for the first test, wherein the second combination of the plurality of lenses is different than the first combination of the plurality of lenses;

automatically generate based on the determined endpoint for the first test to transition to a second test from the first test, a second set of conditions for the second test and a second plurality of response fields, the second set of conditions comprising a second visual reference viewed by the patient and a third combination of the plurality of lenses, and the second plurality of response fields configured to receive second feedback indicative of the patient's vision under the second set of conditions, wherein the third combination of the plurality of lenses is different than the first and the second combinations of the plurality of lenses;

generate a second GUI for display, the second GUI comprising a second script, the second visual reference, and the second plurality of response fields, the second script comprising a string of alphanumeric characters to be read, the second script different than the first script, and each field of the second plurality of response fields comprising at least one of a numerical indicator or a string of alphanumeric characters, wherein at least one response field of the second plurality of response fields is different than at least one response field of the first plurality of response fields;

receive, via an interaction with at least one of the second plurality of response fields displayed on the second GUI, an updated input indicative of the patient's vision under the second set of conditions; and determine an endpoint for the second test based on a determined a visual acuity during the second test matching a predefined visual acuity value such that the endpoint for the second test is different than the endpoint for the first test.

15. The system of claim 14, wherein the processing circuit is configured to subsequently administer a third test subsequent to determining the endpoint for the second test.

16. The system of claim 14, wherein the first set of conditions and the second set of conditions include a combination of subjective lenses and auxiliary lenses of the phoropter.

17. The system of claim 14, wherein the processing circuit is configured to generate the first visual reference and update the updated first visual reference to be viewable by the patient.

18. The system of claim 14, wherein the first set of conditions includes a first combination of auxiliary lenses, a first combination of subjective lenses, and the first visual reference, and the second set of conditions includes one of a second combination of auxiliary lenses different from the first combination of auxiliary lenses, a second combination of subjective lenses different from the first combination of subjective lenses, or the second visual reference different from the first visual reference.

19. The system of claim 14, wherein a determination of an endpoint for a third test corresponds to receiving a predetermined number of replies from the patient based on a set of conditions for the third test.

20. The system of claim 14, wherein the predefined visual acuity value is twenty-twenty.

\* \* \* \* \*